US009884915B2

(12) United States Patent
Chamorro Pérez et al.

(10) Patent No.: US 9,884,915 B2
(45) Date of Patent: Feb. 6, 2018

(54) ANTIBODIES AGAINST CCR9 AND METHODS OF USE THEREOF

(71) Applicant: CONSEJO SUPERIOR DE INVESTIGACIONES CIENTÍFICAS, Madrid (ES)

(72) Inventors: Sonia Chamorro Pérez, Madrid (ES); Ana Franco Villanueva, Madrid (ES); José Alberto García Sanz, Madrid (ES); Leonor Kremer Barón, Madrid (ES); Carlos Martínez Alonso, Madrid (ES); Maria Vela Cuenca, Madrid (ES); Laura Carramolino Fitera, Madrid (ES)

(73) Assignee: Consejo Superior de Investigaciones Cientificas C.S.I.C., Madrid (ES)

( * ) Notice: Subject to any disclaimer, the term of this patent is extended or adjusted under 35 U.S.C. 154(b) by 0 days.

(21) Appl. No.: 15/032,475

(22) PCT Filed: Nov. 25, 2014

(86) PCT No.: PCT/EP2014/075578
§ 371 (c)(1),
(2) Date: Apr. 27, 2016

(87) PCT Pub. No.: WO2015/075269
PCT Pub. Date: May 28, 2015

(65) Prior Publication Data
US 2016/0257756 A1 Sep. 8, 2016

(30) Foreign Application Priority Data
Nov. 25, 2013 (EP) ..................... 13382469

(51) Int. Cl.
C07K 16/28 (2006.01)
A61K 39/395 (2006.01)
G01N 33/574 (2006.01)
A61K 39/00 (2006.01)

(52) U.S. Cl.
CPC .... *C07K 16/2866* (2013.01); *A61K 39/39558* (2013.01); *G01N 33/57492* (2013.01); *A61K 2039/505* (2013.01); *C07K 2317/33* (2013.01); *C07K 2317/51* (2013.01); *C07K 2317/515* (2013.01); *C07K 2317/565* (2013.01); *C07K 2317/73* (2013.01); *C07K 2317/734* (2013.01); *C07K 2317/76* (2013.01); *C07K 2317/92* (2013.01)

(58) Field of Classification Search
CPC ............ C07K 16/2866; C07K 2317/33; C07K 2317/51; C07K 2317/515; C07K 2317/565; C07K 2317/73; C07K 2317/734; C07K 2317/76; C07K 2317/92; G01N 33/57492; A61K 39/39558; A61K 2039/505
See application file for complete search history.

(56) References Cited

U.S. PATENT DOCUMENTS

| 4,522,811 | A | 6/1985 | Eppstein et al. |
| 4,873,316 | A | 10/1989 | Meade et al. |
| 4,946,778 | A | 8/1990 | Ladner et al. |
| 5,591,828 | A | 1/1997 | Bosslet et al. |
| 5,658,570 | A | 8/1997 | Newman et al. |
| 5,736,898 | A | 4/1998 | Kohl et al. |
| 5,739,277 | A | 4/1998 | Presta et al. |
| 5,869,620 | A | 2/1999 | Whitlow et al. |
| 5,910,486 | A | 6/1999 | Cruiel et al. |
| 6,113,898 | A | 9/2000 | Anderson et al. |
| 6,329,159 | B1 | 12/2001 | Andrew et al. |
| 6,936,248 | B1 | 8/2005 | Andrew et al. |
| 8,207,303 | B2 | 6/2012 | Cardarelli et al. |
| 2005/0049286 | A1 | 3/2005 | Wu et al. |

FOREIGN PATENT DOCUMENTS

| EP | 264166 | 4/1988 |
| WO | WO 00/53635 | * 9/2000 |

OTHER PUBLICATIONS

Zabel Ba, et al., The Journal of Experimental Medicine. 190(9):1241-1255. Jan. 1, 1999.*
Paul, WE. Fundamental Immunology, 3rd ed. Raven Press, NY, Chap. 9, pp. 292-295, 1993.*
Rudikoff S. et al. Proc. Natl. Acad. Sci. USA, 79:1979-1983, 1982.*
Colman, PM. Research in Immunology, Elsevier, NY, 145(1):33-36, 1994.*
Amersi et al., Clin. Cancer Res., 14:638-45 (2008).
Banerji et al., Cell, 33729-740 (1983).
Bird, Science 242: 423 (1988).
Byrne et al., Proc. Natl. Acad. Sci USA, 86:5473-5477 (1989).
Calame et al., Adv. Immunol., 43:235-275 (1988).
Caron et al., J. Exp Med. 176:1191-1195 (1992).
Carramolino et al., J. Leukocyte Biol., 66:837-44 (1999).
Carramolino et al., Blood, 97:850-7 (2001).
Carter et al., Proc. Natl. Acad. Sci. USA, 89:4285 (1992).
Chadd and Chamow, Curr. Opin. Biotechnol., 12:188-194 (2001).
Chothia and Lesk, J. Mol. Biol., 196:901-17 (1987).
Chothia et al., Nature, 342:877-83 (1989).
Davis et al., Protein Eng. Des. Sel., 23:195-202 (2010).
Eberhardson et al., Clin Immunol., 149:73-82 (2013).
Edlund et al., Science, 230:912-916 (1985).
Goldenberg, Calif. A Cancer Journal for Clinicians 44, 43 (1994).
Goya et al., 160:1975-81 (1998).
Hollinger et al., Proc. Natl. Acad. Sci. USA, 90:6444-6448 (1993).
Hu et al., Leukaemia Res., 35:1254-60 (2011).
Huston et al., Proc. Natl. Acad Sci USA 85: 5879 (1988).
International Search Report corresponding to PCT/EP2014/075578 dated Feb. 17, 2015.

(Continued)

Primary Examiner — Robert Landsman
(74) Attorney, Agent, or Firm — Jenkins, Wilson, Taylor & Hunt, P.A.

(57) ABSTRACT

The present invention relates to antibodies binding specifically to CCR9, and to antigen-binding fragments thereof. It also relates to uses thereof and diagnostic methods using said antibodies.

6 Claims, 21 Drawing Sheets

(56) References Cited

OTHER PUBLICATIONS

Jakobovits et al., Proc. Mad. Acad. Sci. USA, 90:255 1 (1993).
Jakobovits et al., Nature, 362:255-258 (1993).
Jones et al., Nature, 321:522-525 (1986).
Kremer et al., Methods in Molecular Biology, vol. 239: 243-260 (2004).
Köhler and Milstein, Nature, 256:495-7 (1975).
Letsch et al., J. Invest. Dermatol., 122:685-90 (2004).
Newman et al., Biotechnology, 10: 1458-1460 (1992).
Niwa et al., Cancer Res., 64(6):2127-33 (2004).
Niwa et al., Gene, 108: 193-9 (1991).
Pastan et al., Cell, 47, 641 (1986).
Pinkert et al., Genes Dev 1:268-277 (1987).
Presta et al., J. Immunol., 151:2623 (1993).
Reichmann et al., Nature, 332:323-327 (1988).
Richmond A, Clin., Cancer Res., 14:621-3 (2008).
Sharma et al., Int. J. Cancer, 127:2020-30 (2010).
Shopes, B., J. Immunol. 148:2918-2922 (1992).
Sims et al., J. Immunol., 151:2296 (1993).
Tamura et al., J. Immunol., 163: 1432-1441 (2000).
Verhoeyen et al., Science, 239:1534-1536 (1988).
Ward et al., Nature 334: 544 (1989).
Winoto et al., EMBO J. 8:729-733 (1989).
Wolff et al., Cancer Research 53:2560-2565 (1993).
Ye et al., Nucleic Acids Res., 41(web server issue):W34-40 (2013).
Youn et al., Blood, 94:2533-2536 (1999).
Zaballos et al., J. Immunol., 162:5671-5675 (1999).
Zabel et al., "Human G protein-coupled receptor GPR-9-6/CC chemokine receptor 9 is selectively expressed on intestinal homing T lymphocytes, mucosal lymphocytes and thymocytes and is required for thymus-expressed chemokine-mediated chemotaxis," Journal of Experimental Medicine. 190(9):1241-1255 (1999).

* cited by examiner

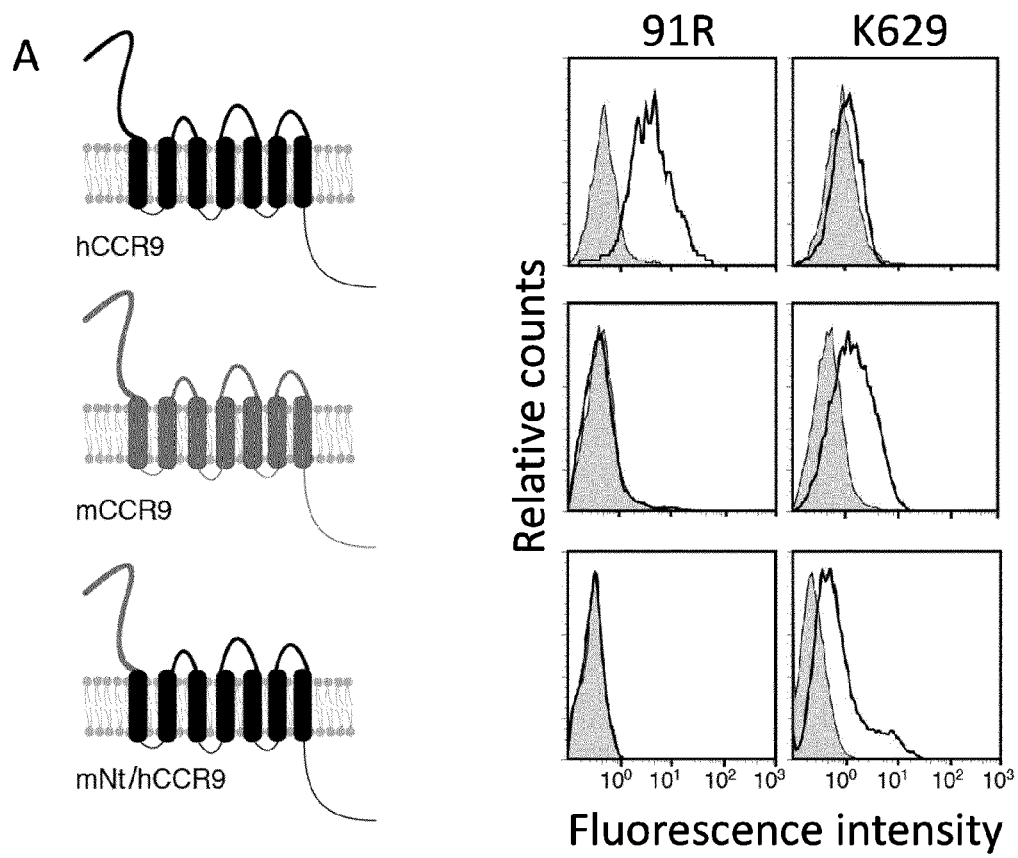
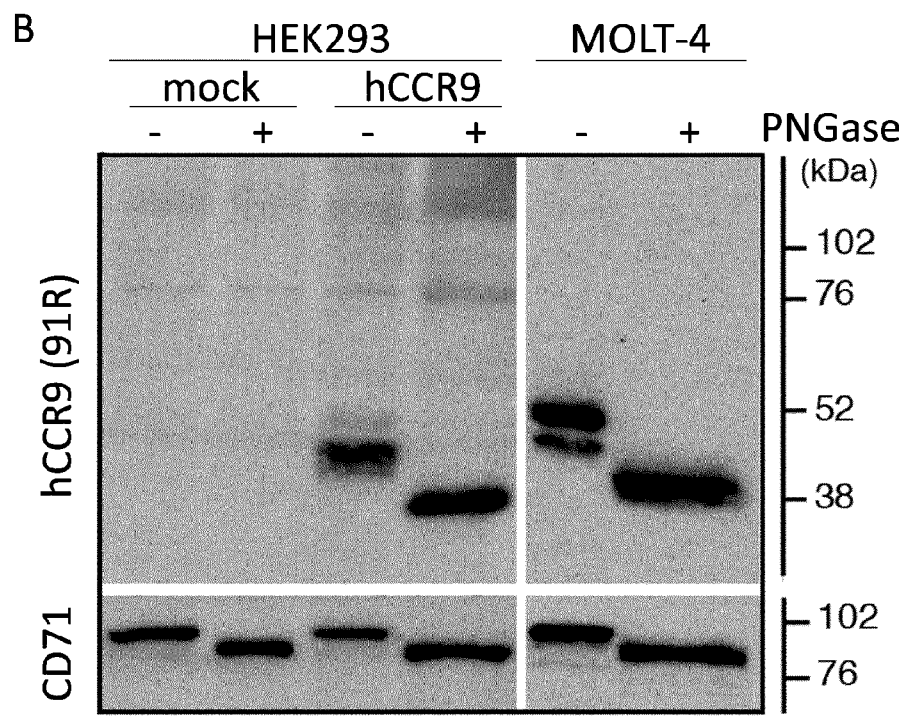
Figure 2

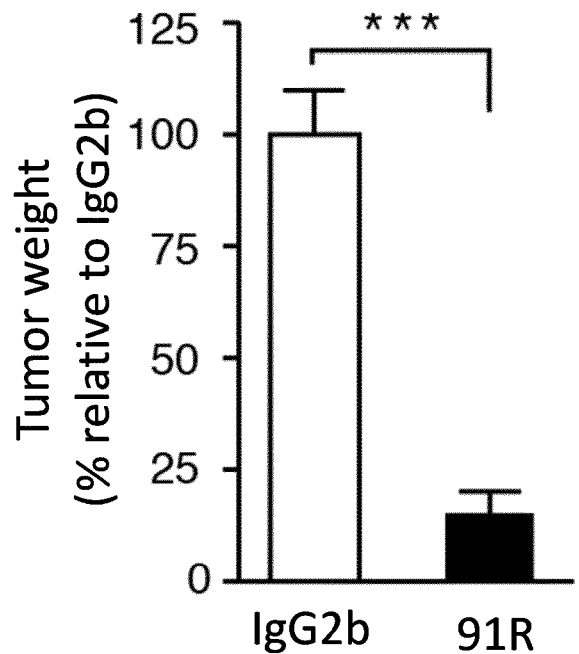
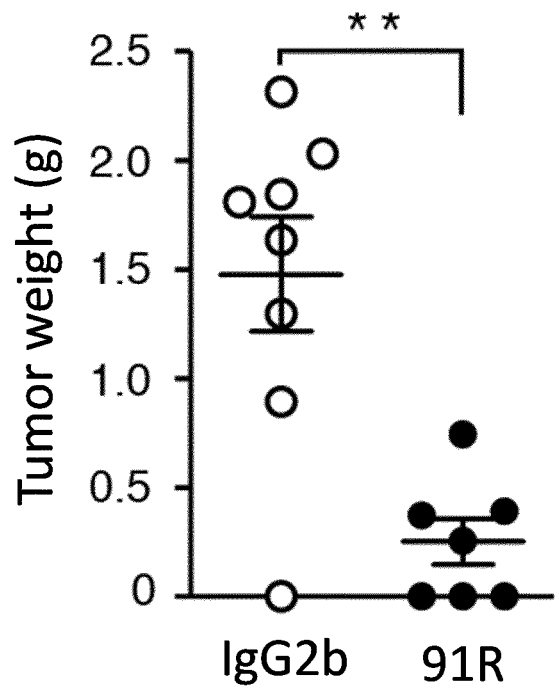
Figure 5 (cont.)

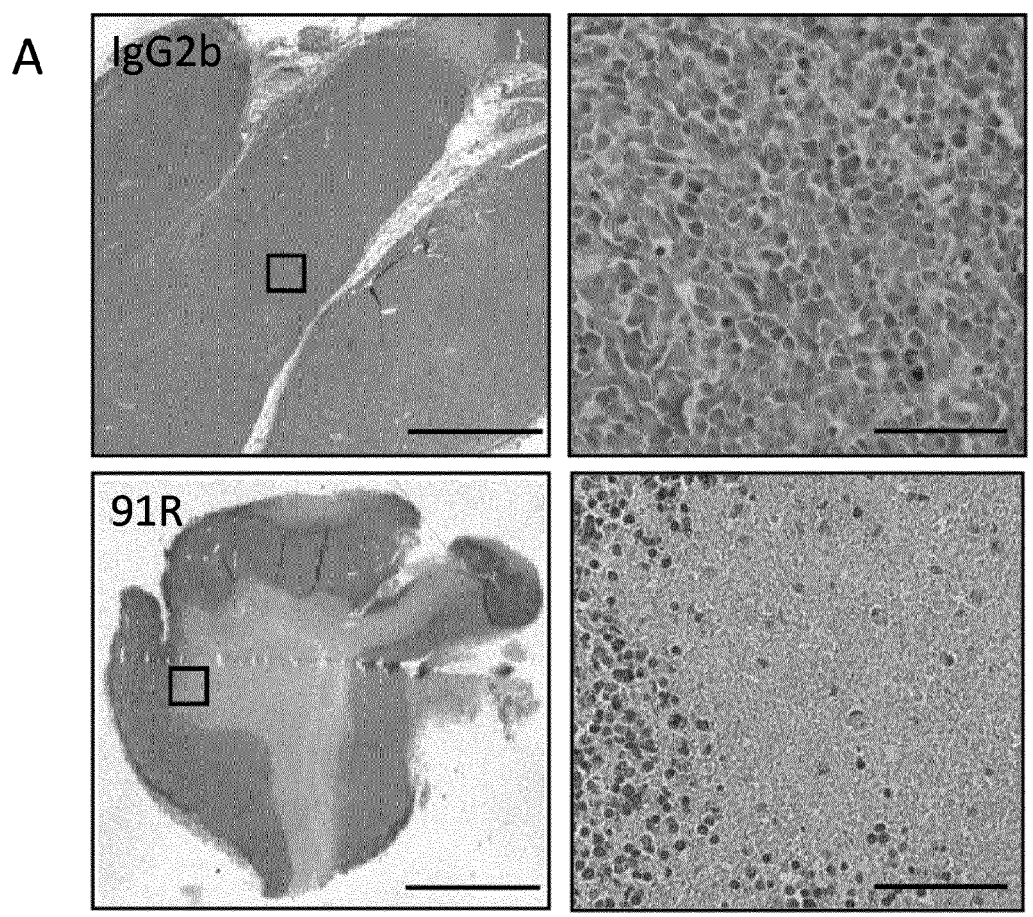
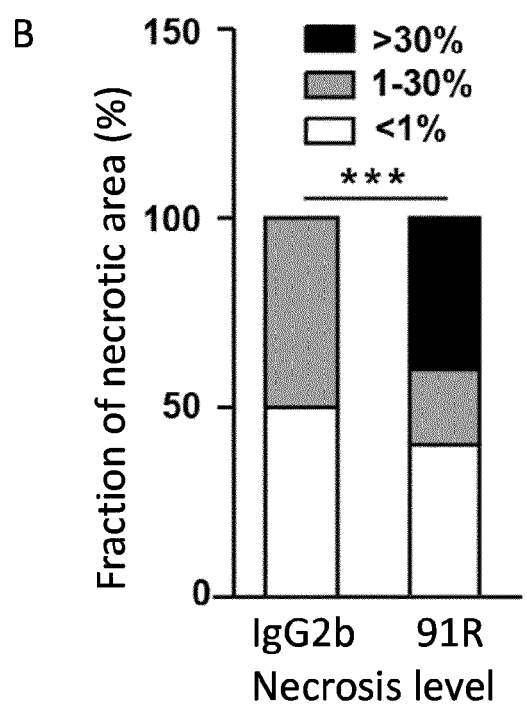
Figure 6

C

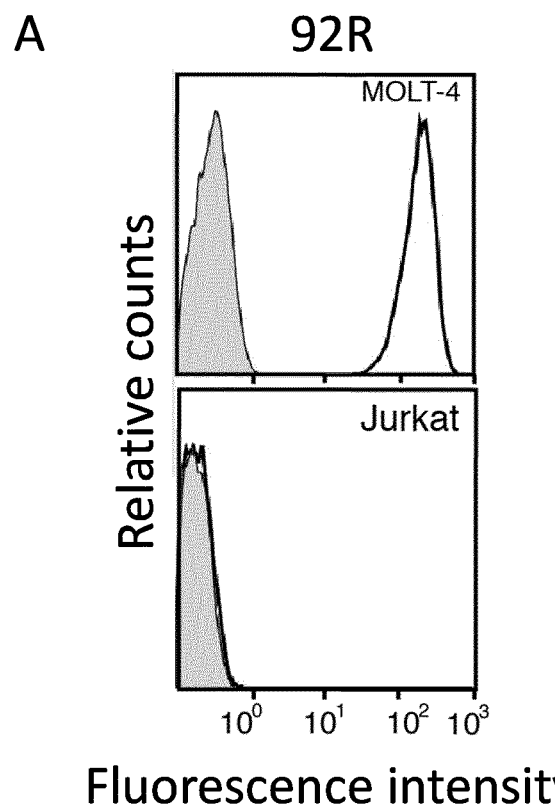
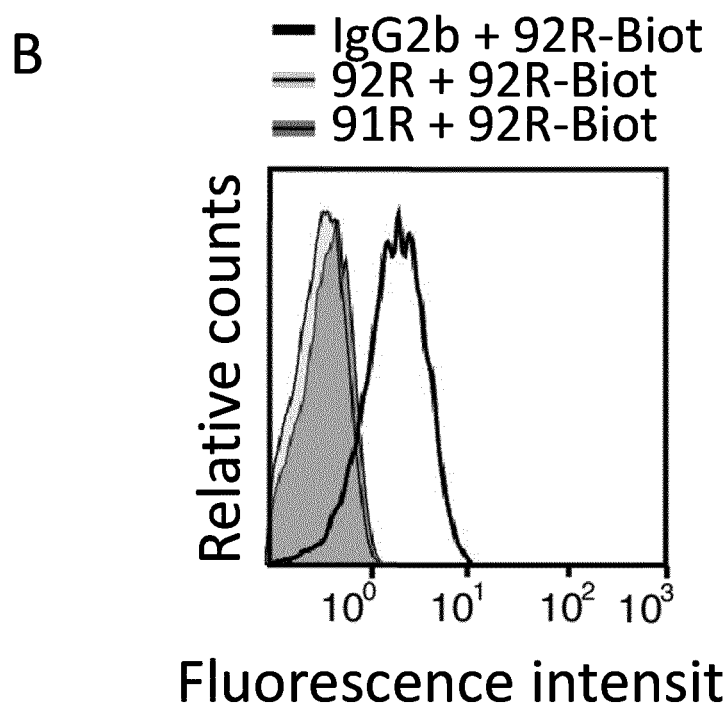
Figure 8

Alignment of 3C3, 91R and 92R Heavy Chain CDRs

```
            CDR-H1
91R         -NFWMN    (SEQ ID NO: 1)
92R         -KFWMN    (SEQ ID NO: 7)
3C3         SAYTWH    (SEQ ID NO: 13)
              :  :

CDR-H2
91R         EIRLKSNNYATHYAESVKG    (SEQ ID NO: 2)
92R         EIRLKSNNYATHYAESVKG    (SEQ ID NO: 2)
3C3         YIHYSG---RTSYNPSLKS    (SEQ ID NO: 14)
            *:  ..    * *  *:*.

CDR-H3
91R         DG--WFAY  (SEQ ID NO: 3)
92R         DG--WFAY  (SEQ ID NO: 3)
3C3         NRYYYFDV  (SEQ ID NO: 15)
              :    :*
```

Alignment of 3C3, 91R and 92R Light Chain CDRs

```
             CDR-L1
91R         RSSQSLLHSNGNTYVQ  (SEQ ID NO: 4)
92R         RSSQSLVHSNGNTYLN  (SEQ ID NO: 8)
3C3         RSSQSIVHSNGNTYLE  (SEQ ID NO: 16)
            *****::*******::

CDR-L2
91R         KVSNRFP  (SEQ ID NO: 5)
92R         KVSNRFS  (SEQ ID NO: 9)
3C3         KVSNRFS  (SEQ ID NO: 9)
            ******.

CDR-L3
91R         AQSTHVPRT  (SEQ ID NO: 6)
92R         SQSTHFPRT  (SEQ ID NO: 10)
3C3         FQGSLVPPT  (SEQ ID NO: 17)
            *.: .* *
```

Figure 9

A
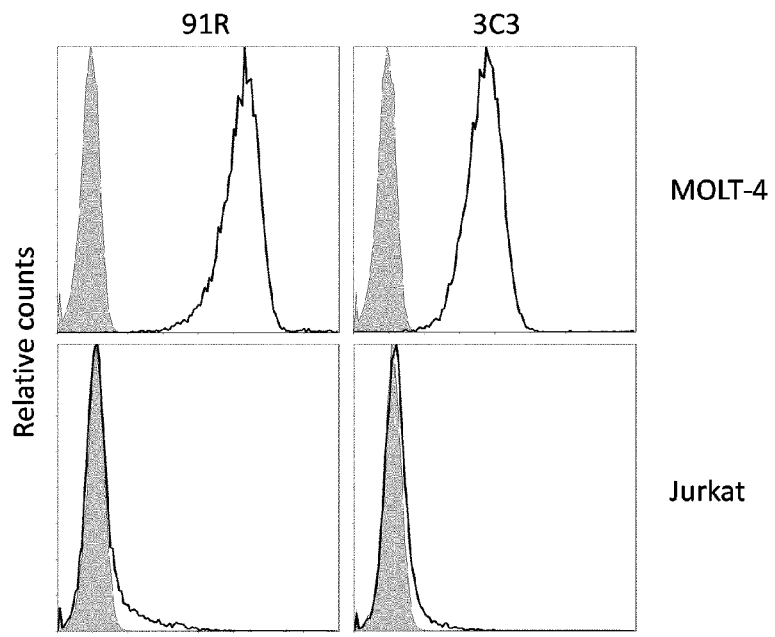
MOLT-4
Jurkat
B
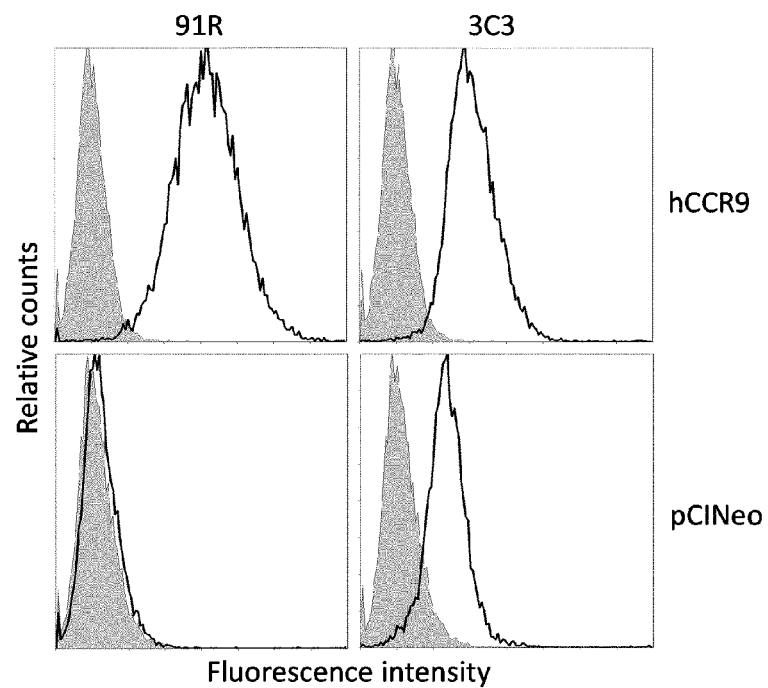
hCCR9
pClNeo
Fluorescence intensity
Figure 10

SEQUENCE LISTING

```
<160> NUMBER OF SEQ ID NOS: 17

<210> SEQ ID NO 1
<211> LENGTH: 5
<212> TYPE: PRT
<213> ORGANISM: Artificial Sequence
<220> FEATURE:
<223> OTHER INFORMATION: Artificially synthesized CDR-H1 sequence

<400> SEQUENCE: 1

Asn Phe Trp Met Asn
1               5

<210> SEQ ID NO 2
<211> LENGTH: 19
<212> TYPE: PRT
<213> ORGANISM: Artificial Sequence
<220> FEATURE:
<223> OTHER INFORMATION: Artificially synthesized CDR-H2 sequence

<400> SEQUENCE: 2

Glu Ile Arg Leu Lys Ser Asn Asn Tyr Ala Thr His Tyr Ala Glu Ser
1               5                   10                  15

Val Lys Gly

<210> SEQ ID NO 3
<211> LENGTH: 6
<212> TYPE: PRT
<213> ORGANISM: Artificial Sequence
<220> FEATURE:
<223> OTHER INFORMATION: Artificially synthesized CDR-H3 sequence

<400> SEQUENCE: 3

Asp Gly Trp Phe Ala Tyr
1               5

<210> SEQ ID NO 4
<211> LENGTH: 16
<212> TYPE: PRT
<213> ORGANISM: Artificial Sequence
<220> FEATURE:
<223> OTHER INFORMATION: Artificially synthesized CDR-L1 sequence

<400> SEQUENCE: 4

Arg Ser Ser Gln Ser Leu Leu His Ser Asn Gly Asn Thr Tyr Val Gln
1               5                   10                  15

<210> SEQ ID NO 5
<211> LENGTH: 7
<212> TYPE: PRT
<213> ORGANISM: Artificial Sequence
<220> FEATURE:
<223> OTHER INFORMATION: Artificially synthesized CDR-L2 sequence
```

```
<400> SEQUENCE: 5

Lys Val Ser Asn Arg Phe Pro
1               5

<210> SEQ ID NO 6
<211> LENGTH: 9
<212> TYPE: PRT
<213> ORGANISM: Artificial Sequence
<220> FEATURE:
<223> OTHER INFORMATION: Artificially synthesized CDR-L3 sequence

<400> SEQUENCE: 6

Ala Gln Ser Thr His Val Pro Arg Thr
1               5

<210> SEQ ID NO 7
<211> LENGTH: 5
<212> TYPE: PRT
<213> ORGANISM: Artificial Sequence
<220> FEATURE:
<223> OTHER INFORMATION: Artificially synthesized CDR-H1 sequence

<400> SEQUENCE: 7

Lys Phe Trp Met Asn
1               5

<210> SEQ ID NO 8
<211> LENGTH: 16
<212> TYPE: PRT
<213> ORGANISM: Artificial Sequence
<220> FEATURE:
<223> OTHER INFORMATION: Artificially synthesized CDR-L1 sequence

<400> SEQUENCE: 8

Arg Ser Ser Gln Ser Leu Val His Ser Asn Gly Asn Thr Tyr Leu Asn
1               5                   10                  15

<210> SEQ ID NO 9
<211> LENGTH: 7
<212> TYPE: PRT
<213> ORGANISM: Artificial Sequence
<220> FEATURE:
<223> OTHER INFORMATION: Artificially synthesized CDR-L2 sequence

<400> SEQUENCE: 9

Lys Val Ser Asn Arg Phe Ser
1               5

<210> SEQ ID NO 10
<211> LENGTH: 9
<212> TYPE: PRT
<213> ORGANISM: Artificial Sequence
<220> FEATURE:
<223> OTHER INFORMATION: Artificially synthesized CDR-L3 sequence

<400> SEQUENCE: 10

Ser Gln Ser Thr His Phe Pro Arg Thr
1               5

<210> SEQ ID NO 11
<211> LENGTH: 21
<212> TYPE: PRT
<213> ORGANISM: Artificial Sequence
<220> FEATURE:
<223> OTHER INFORMATION: Artificially synthesized amino acids 2-22 from
      the N-terminal extracellular domain of CCR9 isoform A
```

```
<400> SEQUENCE: 11

Thr Pro Thr Asp Phe Thr Ser Pro Ile Pro Asn Met Ala Asp Tyr
1               5                   10                  15

Gly Ser Glu Ser Thr
            20

<210> SEQ ID NO 12
<211> LENGTH: 18
<212> TYPE: PRT
<213> ORGANISM: Artificial Sequence
<220> FEATURE:
<223> OTHER INFORMATION: Artificially synthesized amino acids 13-30 from
      the N-terminal extracellular domain of CCR9 isoform A

<400> SEQUENCE: 12

Met Ala Asp Asp Tyr Gly Ser Glu Ser Thr Ser Ser Met Glu Asp Tyr
1               5                   10                  15

Val Asn

<210> SEQ ID NO 13
<211> LENGTH: 6
<212> TYPE: PRT
<213> ORGANISM: Artificial Sequence
<220> FEATURE:
<223> OTHER INFORMATION: Artificially synthesized CDR-H1 of 3C3 mAb

<400> SEQUENCE: 13

Ser Ala Tyr Thr Trp His
1               5

<210> SEQ ID NO 14
<211> LENGTH: 16
<212> TYPE: PRT
<213> ORGANISM: Artificial Sequence
<220> FEATURE:
<223> OTHER INFORMATION: Artificially synthesized CDR-H2 of 3C3 mAb

<400> SEQUENCE: 14

Tyr Ile His Tyr Ser Gly Arg Thr Ser Tyr Asn Pro Ser Leu Lys Ser
1               5                   10                  15

<210> SEQ ID NO 15
<211> LENGTH: 8
<212> TYPE: PRT
<213> ORGANISM: Artificial Sequence
<220> FEATURE:
<223> OTHER INFORMATION: Artificially synthesized CDR-H3 of 3C3 mAb

<400> SEQUENCE: 15

Asn Arg Tyr Tyr Tyr Phe Asp Val
1               5

<210> SEQ ID NO 16
<211> LENGTH: 16
<212> TYPE: PRT
<213> ORGANISM: Artificial Sequence
<220> FEATURE:
<223> OTHER INFORMATION: Artificially synthesized CDR-L1 of 3C3 mAb

<400> SEQUENCE: 16

Arg Ser Ser Gln Ser Ile Val His Ser Asn Gly Asn Thr Tyr Leu Glu
1               5                   10                  15

<210> SEQ ID NO 17
<211> LENGTH: 9
```

```
<212> TYPE: PRT
<213> ORGANISM: Artificial Sequence
<220> FEATURE:
<223> OTHER INFORMATION: Artificially synthesized CDR-L3 of 3C3 mAb

<400> SEQUENCE: 17

Phe Gln Gly Ser Leu Val Pro Pro Thr
 1               5
```

ANTIBODIES AGAINST CCR9 AND METHODS OF USE THEREOF

CROSS REFERENCE TO RELATED APPLICATION

This application is a United States National Stage Application of PCT International Patent Application Serial No. PCT/EP2014/075578, filed Nov. 25, 2014.

FIELD OF THE INVENTION

The present invention relates to antibodies binding specifically to CCR9, and to uses thereof and diagnostic methods using said antibodies.

BACKGROUND OF THE INVENTION

Chemokines are a family of small, structurally related proteins that bind to seven transmembrane spanning G protein-coupled receptors. Chemokines and their receptors have an essential role in organogenesis and lymphocyte trafficking, in both homeostatic and inflammatory conditions. There is a strong association between aberrant tumour cell expression of chemokine receptors such as CXCR4 or CCR7 and cancer progression, organ-selective metastasis, and poor prognosis. Human chemokine receptor CCR9 (accession number U45982 of the GENBANK® biosequence database) was identified by Zaballos et al. (1999, J Immunol 162:5671-5; EMBL database accession number AJ132337) and Youn et al. (1999, Blood 94:2533-6). Although there are not many data for CCR9, its expression on tumour cells correlates with metastasis in the small intestine (Letsch et al., 2004, J Invest Dermatol 122:685-90; Richmond A, 2008, Clin Cancer Res 14:621-3; Amersi et al., 2008, Clin Cancer Res 14:638-45).

CCR9 is expressed almost exclusively in lymphoid cells in the thymus, infiltrating cells in small bowel, a small subset of circulating memory T lymphocytes (CCR9$^+$α$_4$β$_7^{hi}$), IgA-secreting plasma cells and plasmacytoid dendritic cells. The only known CCR9 ligand is the chemokine TECK (CCL25), which is secreted by epithelial and dendritic cells from the thymus and the small intestinal crypt epithelium. The CCR9-CCL25 interaction is a key regulator of thymocyte migration in thymus and of cell homing to the intestinal tract. Aberrant CCR9 expression in ovarian carcinomas, prostate cancer, breast cancer and melanomas is correlated with in vitro invasiveness in response to CCL25. CCR9 overexpression in acute and chronic T cell lineage leukaemia is linked to disease aggressiveness. CCR9 provides competitive advantages to tumour cells; CCL25 engagement enhances cell survival and resistance to apoptosis via the phosphatidylinositide 3-kinase (PI3K)/Akt pathway in breast and ovarian carcinomas, activates the JNK1 anti-apoptotic pathway, and enhances proliferation by activating Notch1 in leukaemia cells.

Specific therapeutic tools to treat human CCR9$^+$ tumours growing in xenogenic models are limited to the use of toxin-coupled ligands (CCL25-PE38 fusion protein) (Hu et al., 2011, Leukaemia Res 35:1254-60) or ligand-specific antibodies alone or combined with the cytotoxic agent etoposide (Sharma et al., 2010, Int J Cancer 127:2020-30). In these strategies, the CCL25-CCR9 interaction is targeted to eliminate tumour cells; although the results have been limited, they provide evidence that CCR9 is a potential target for cancer immunotherapy.

Given the lack of therapies targeted to CCR9, there is still a need in the art to provide agents recognising CCR9 specifically that are suitable for the diagnosis, prognosis and/or treatment of a disease or condition concomitant with cells expressing CCR9.

SUMMARY OF THE INVENTION

In an aspect, the invention relates to an antibody binding specifically to CCR9, or an antigen-binding fragment thereof, comprising
  a) a heavy chain comprising at least one complementarity determining region (CDR) selected from:
    a CDR comprising the amino acid sequence shown in SEQ ID NO: 1 [CDR-H1] or a variant thereof;
    a CDR comprising the amino acid sequence shown in SEQ ID NO: 2 [CDR-H2] or a variant thereof; and
    a CDR comprising the amino acid sequence shown in SEQ ID NO: 3 [CDR-H3] or a variant thereof; and
  b) a light chain comprising at least one complementarity determining region (CDR) selected from:
    a CDR comprising the amino acid sequence shown in SEQ ID NO: 4 [CDR-L1] or a variant thereof;
    a CDR comprising the amino acid sequence shown in SEQ ID NO: 5 [CDR-L2] or a variant thereof; and
    a CDR comprising the amino acid sequence shown in SEQ ID NO: 6 [CDR-L3] or a variant thereof.

In another aspect, the invention relates to a nucleic acid selected from the group consisting of:
  i) a nucleic acid, DNA or RNA, coding for said antibody or antigen-binding fragment thereof, and
  ii) a complementary nucleic acid of a nucleic acid as defined in i).

In another aspect, the invention relates to a gene construct comprising said nucleic acid.

In another aspect, the invention relates to an expression cassette comprising said nucleic acid or said gene construct.

In another aspect, the invention relates to a vector comprising said nucleic acid, or said gene construct, or said expression cassette. In a particular embodiment, said vector is an expression vector.

In another aspect, the invention relates to a cell comprising said nucleic acid, or said gene construct, or said expression cassette, or said vector.

In another aspect, the invention relates to a method for producing said antibody or antigen-binding fragment thereof, which comprises growing said cell under conditions permitting the production of said antibody or antigen-binding fragment thereof.

In another aspect, the invention relates to the use of an antibody of the invention for the in vitro diagnosis and/or prognosis of a disease or condition wherein cells expressing CCR9 participate.

In another aspect, the invention relates to a method for diagnosis and/or prognosis of a disease or condition wherein cells expressing CCR9 participate in a subject, comprising:
  a) contacting said antibody or antigen-binding fragment thereof with a sample comprising cells from said subject;
  b) detecting and/or quantifying CCR9 in said sample from said subject;
  c) comparing the presence and/or amount and/or distribution of said CCR9 detected in said sample from said subject with that of CCR9 detected in a control sample; and d) correlating the result obtained with the presence of a disease or condition wherein cells expressing CCR9 participate.

In another aspect, the invention relates to the use of said antibody, or antigen-binding fragment thereof, for in vivo diagnosis and/or prognosis of a disease or condition wherein cells expressing CCR9 participate, or to the use of said antibody, or antigen-binding fragment thereof, in a method for in vivo diagnosis and/or prognosis of a disease or condition wherein cells expressing CCR9 participate; alternatively, this aspect can be expressed as the use of said antibody, or antigen-binding fragment thereof, in the manufacture of a composition for in vivo diagnosis and/or prognosis of a disease or condition wherein cells expressing CCR9 participate. In another alternative wording, this aspect can be expressed as said antibody, or antigen-binding fragment thereof, for use in an in vivo diagnosis and/or prognosis of a disease or condition wherein cells expressing CCR9 participate, or as said antibody, or antigen-binding fragment thereof, for use in a method for in vivo diagnosis and/or prognosis of a disease or condition wherein cells expressing CCR9 participate.

In another aspect, the invention relates to an in vitro method for monitoring the response to treatment of a disease or condition wherein cells expressing CCR9 participate in a subject under treatment comprising:
a) contacting the antibody of the invention with a first sample comprising cells from said subject taken at a first time-point;
b) detecting and/or quantifying CCR9 in said first sample;
c) contacting the antibody of the invention with a second sample comprising cells from said subject taken at a second time-point;
d) detecting and/or quantifying CCR9 in said second sample;
e) comparing the presence and/or amount and/or distribution of CCR9 detected in said first sample and second sample; and
f) correlating the result obtained with the response to treatment of a disease or condition wherein cells expressing CCR9 participate.

In another aspect, the invention relates to said antibody or antigen-binding fragment thereof for use as a medicament.

In another aspect, the invention relates to said antibody or antigen-binding fragment thereof for use in the treatment of a disease or condition wherein cells expressing CCR9 participate.

In another aspect, the invention relates to the use of said antibody or antigen-binding fragment thereof in the preparation of a medicament for treatment of a disease or condition wherein cells expressing CCR9 participate.

In another aspect, the invention relates to said antibody or antigen-binding fragment thereof for use in a method of treatment of a disease, wherein said method of treatment comprises killing the target cells, i.e., cells expressing CCR9 (CCR9$^+$); or, alternatively, to the use of antibody or antigen-binding fragment thereof in the manufacture of a medicament for the treatment of a disease, wherein said treatment comprises killing the target cells.

In another aspect, the invention relates to said antibody or antigen-binding fragment thereof for use in tumour diagnosis by using imaging techniques wherein said tumour comprises cells expressing CCR9 (CCR9$^+$), or, alternatively, to the use of said antibody or antigen-binding fragment thereof in the manufacture of a composition for in vivo tumour diagnosis by using imaging techniques wherein said tumour comprises cells expressing CCR9 (CCR9$^+$).

In another aspect, the invention relates to said antibody or antigen-binding fragment thereof for use in targeting a drug to a tumour wherein said tumour comprises cells expressing CCR9 (CCR9$^+$), or, alternatively, to the use of said antibody or antigen-binding fragment thereof in the manufacture of a composition for in vivo targeting a drug to a tumour wherein said tumour comprises cells expressing CCR9 (CCR9$^+$).

In another aspect, the invention relates to said antibody or antigen-binding fragment thereof for use in the treatment of an inflammatory disease by depleting cells expressing CCR9 in said inflammatory disease, or, alternatively to the use of said antibody or antigen-binding fragment thereof in the manufacture of a pharmaceutical composition for treating an inflammatory disease by depleting cells expressing CCR9.

In another aspect, the invention relates to the use of said antibody or antigen-binding fragment thereof as a tool in biotechnology techniques for detection, localization and/or quantification of CCR-9 protein in a sample.

In another aspect, the invention relates to the use of said antibody or antigen-binding fragment thereof in the detection and/or quantification of CCR9, or cells expressing CCR9, present in a sample.

In another aspect, the invention relates to a method for the detection and/or quantification of CCR9, or cells expressing CCR9, present in a sample, by using said antibody or antigen-binding fragment thereof.

In another aspect, the invention relates to a kit comprising at least one of said antibody or antigen-binding fragment thereof; in a particular embodiment, said kit comprises, in addition to said antibody or antigen-binding fragment thereof, a further therapeutic agent.

In another aspect, the invention relates to the use of said kit for diagnosing a disease or condition wherein cells expressing CCR9 participate, or for monitoring the response to treatment of a disease or condition wherein cells expressing CCR9 participate in a subject under treatment, or for treatment a disease or condition wherein cells expressing CCR9 participate, or for targeting a drug to a tumour wherein said tumour comprises CCR9$^+$ cells, or as a tool in biotechnology techniques for detection, localization and/or quantification of CCR9 protein in a sample, or for detecting and/or quantifying CCR9, or cells expressing CCR9, present in a sample.

In another aspect, the invention relates to a pharmaceutical composition comprising a therapeutically effective amount of at least said antibody or antigen-binding fragment thereof, together with a pharmaceutically acceptable excipient or carrier.

BRIEF DESCRIPTION OF THE DRAWINGS

(FIG. 1A) HEK293 cells stably transfected with hCCR9, mCCR9, hCCR4, hCCR5, hCCR6, hCCR8 (open histograms) or the empty pClneo vector (filled histograms) were stained with 91R mAb and analyzed by flow cytometry. (FIG. 1B) Human leukemia MOLT-4 and Jurkat cells were stained with anti-human CCR9 mAb 91R and 112509 (open histograms) or isotype-matched control mAb (filled histograms) and analyzed by flow cytometry. (FIG. 1C) Representative flow cytometry analysis of MOLT-4 staining with different doses (0.12-10 µg/ml) of 91R (filled histograms), 112509 (open histograms), or isotype-matched mAb (grey lines) (n=5). (FIG. 1D) Flow cytometry analysis of human thymocytes using anti-CD4, -CD8 and 91R antibodies. Percentages of positive cells in gates of the CD4/CD8 plot are indicated; hCCR9 expression is shown for each subpopulation. (FIG. 1E) Flow cytometry showing human peripheral blood cells stained with 91R and anti-CD3, with the total cell population and CD3 vs 91R staining in the lymphocyte gate. (FIG. 1F) Representative western blot of membrane-enriched fractions of hCCR9- or pClneo-transfected HEK293 cells, MOLT-4, and Jurkat cells incubated with 91R; the same membrane was probed with anti-CD71 Ab as loading control (n=3).

FIGS. 2A and 2B. 91R mAb recognizes the human CCR9 N-terminal domain. (FIG. 2A) Diagram of human and mouse CCR9 and the chimeric CCR9 bearing the human CCR9 sequence with the N-terminal domain (Nt) replaced by the murine sequence (mNt/hCCR9); flow cytometry analyses with 91R mAb (anti-hCCR9; open histograms), rabbit polyclonal K629 (anti-mCCR9; open histograms) and rabbit control Ab (filled histograms). (FIG. 2B) Membrane-enriched lysates from pClneo-, hCCR9-HEK and MOLT-4 cells were used for Western blot with 91R and anti-CD71 Ab as loading control. Where indicated, cell lysates were PNGase-treated to remove N-glycosylated residues. A representative experiment is shown (n=2).

(FIG. 4A) Antibody administration schedule on days 1, 7, 14 and 21 for mice bearing tumor cells injected in each flank. (FIG. 4B) Tumor growth kinetics. Tumor volume was measured at times indicated and calculated as V=[axial diameter length, mm]×[(rotational diameter, mm)$^2$/2] (6 mice/group). (FIG. 4C) Tumor weight (%) relative to IgG2b treatment on d56. Mean±SEM (n=6 mice/group). (FIG. 4D) Images of tumors from IgG2b- and 91R-treated mice at the time of sacrifice (day 56). Bar=1 cm. (FIG. 4E) Antibody administration schedule on days 7, 14, 21, and 28 in mice injected only in one flank. (FIG. 4F) Tumor volume was calculated as in C (10 mice/group). (FIG. 4G) Percentage of tumor weight relative to IgG2b treatment on d72. Results show mean±SEM (n=10 mice/group). (FIG. 4H) Images of tumors from IgG2b- and 91R-treated mice at the time of sacrifice (day 72). Bar=1 cm. Student's t-test, *p<0.001, p<0.01, *p<0.05.

(FIG. 5A) Treatment schedule using luminescent MOLT-4 cells (MOLT-4-luc) inoculated s.c. into each flank of Rag2$^{-/-}$ mice on d0. Experimental groups received i.p. inoculations of 91R or control IgG2b mAb on d1 (4 mg/kg) and d6 (2 mg/kg). Luminescence imaging was analyzed from days 1 to 28; mice were sacrificed on d62 and tumors removed. (FIG. 5B) Images of a representative mouse from each group at indicated times post-cell inoculation. (FIG. 5C) Tumor growth kinetics after tumor implant. Relative bioluminescence units are shown as mean±SEM. (FIG. 5D) Percentage of tumor burden relative to IgG2b treatment at d62. Results show mean±SEM. (FIG. 5E) Tumor weights per mouse; data show mean±SEM. C-E, n=7 mice/group. Student's t-test, *p<0.001, p<0.01, *p<0.05.

(FIGS. 6A-6D) Histological analysis of xenografted MOLT-4 tumors (n=5 mice/group). (FIG. 6A) Hematoxylin/eosin-stained sections from xenografted MOLT-4 tumors treated with 91R or control IgG2b mAb; bar=2 mm. Right, images at higher magnification; bar=25 μm. (FIG. 6B) Graph shows tumor classification by necrotic stage, expressed as percentage of necrotic area per tumor (<1%, 1-30% and >30%). Chi-square test, *p<0.0001. (FIG. 6C) Apoptosis level in tumors was analyzed by TUNEL assays. Proliferation levels were determined by PCNA immunostaining. Blood vessels were detected by CD31 staining. Tissue sections were DAPI-counterstained. Bar=50 μm. (FIG. 6D) Quantitative analyses of TUNEL- and PCNA-positive nuclei and vessels per optical field. Mann-Whitney test, *p<0.001, **p<0.01, *p<0.05.

(FIG. 7A) Specific complement lysis in the absence of antibody or with 91R, 112509 mAb, or isotype-matched mAb (IgG2a or IgG2b). Each condition was analyzed in triplicate. Data show mean±SEM for four independent experiments. (FIG. 7B) Dose-response curve for specific complement lysis using 91R and a control IgG2b mAb at indicated concentrations. Data show mean±SEM for one representative experiment of four. (FIG. 7C) Effect of time exposure to BRC. Data show mean±SEM for triplicates from one representative experiment of two. (FIG. 7D) Specific complement lysis in a dose response curve for BRC. Data show percent mean±SEM for triplicates from one representative experiment of two. Student's t-test, *p<0.001, p<0.01, *p<0.05.

(FIG. 8A) Human T cell leukemia MOLT-4 and Jurkat cells were stained with anti-human CCR9 mAb 92R (open histograms) or isotype-matched control mAb (filled histograms) and analyzed by flow cytometry. (FIG. 8B) 91R mAb competes with 92R mAb for binding to MOLT-4 cells. Representative flow cytometry analysis of MOLT-4 cells, preincubated with 10 μg/ml mAb (control IgG2b, 92R or 91R) and stained with biotin-labeled 92R mAb (92R-Biot) followed by FITC conjugated avidin. (FIG. 8C) The mAbs 91R and 92R compete with each other for binding to a synthetic peptide comprising hCCR9 amino acids 2-22. ELISA plates were coated with a synthetic peptide corresponding to amino acids 2-22 of hCCR9. After incubation with PBS, control IgG2b, 92R or 91R, 91R-Biot or 92R-Biot mAb were added. Plates were developed with horseradish peroxidase conjugated avidin. Data show mean±SEM for one representative experiment. Student's t-test, *p<0.001, p<0.01, *p<0.05.

FIG. 9. Sequence alignment of the six CDRs of 91R, 92R and 3C3 mAbs. The amino acid sequences of the six CDRs (CDR-H1, CDR-H2, CDR-H3, CDR-L1, CDR-L2, CDR-L3) of 91R, 92R and 3C3 mAbs were aligned. Key: "*" denotes identical residues; ":" denotes conserved substitutions; "." denotes semi-conserved substitution.

FIGS. 10A and 10B. 91R and 3C3 mAbs specifically recognize human T cells expressing the endogenous chemokine receptor CCR9 and hCCR9-transfected HEK-293 cells. (FIG. 10A) 91R and 3C3 mAbs bind specifically to MOLT4 cells, a CCR9+ human acute lymphoblastic leukemia T cell line. Human leukemia MOLT-4 (hCCR9+) and Jurkat (hCCR9-) cells (2×10$^5$ cells/well) were stained with isotype-matched control mAbs (10 µg/ml, filled histograms) or anti-human CCR9 mAbs 91R or 3C3 (10 µg/ml, open histograms). After washing, cells were incubated with a PE-labelled goat anti mouse immunoglobulins antibody and analysed by flow cytometry. One representative experiment is shown (n=3). (FIG. 10B) 91R and 3C3 mAbs have different recognition patterns of hCCR9-transfected HEK-293. In particular, 3C3 mAb has higher non-specific binding to mock-transfected cells than 91R mAb. Human HEK-293 cells (2×10$^5$ cells/well), stably transfected with hCCR9 or the empty pCIneo vector, were stained with isotype-matched control mAbs (10 µg/ml, filled histograms) or anti-human CCR9 mAbs 91R or 3C3 (10 µg/ml, open histograms). After washing, cells were incubated with a PE-labelled goat anti mouse immunoglobulins antibody and analysed by flow cytometry. One representative experiment is shown (n=2).

DETAILED DESCRIPTION OF THE INVENTION

Antibody of the Invention

Figure 1:
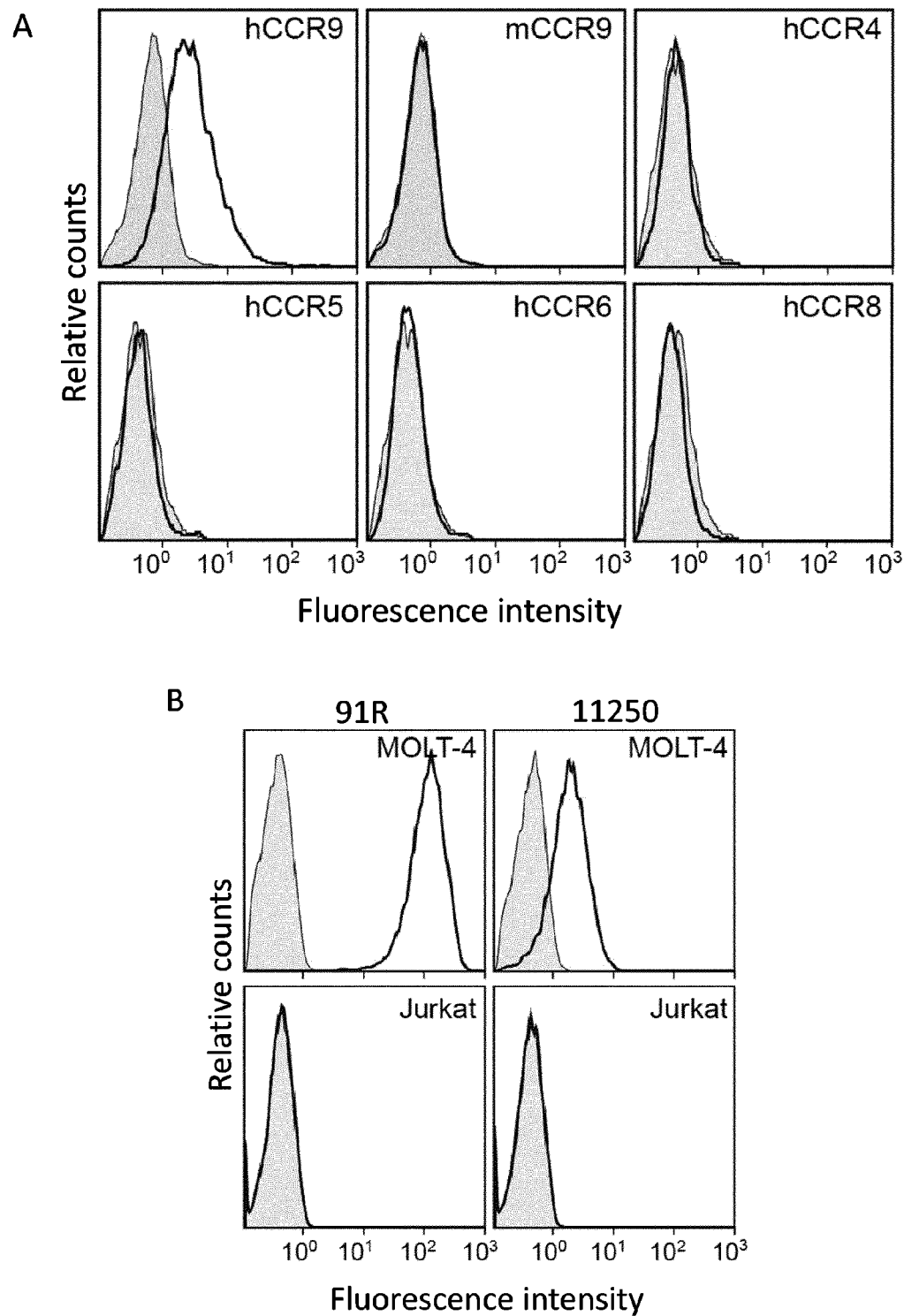
FIGS. 1A-1F. 91R mAb is specific for human chemokine receptor CCR9.
Figure 1:
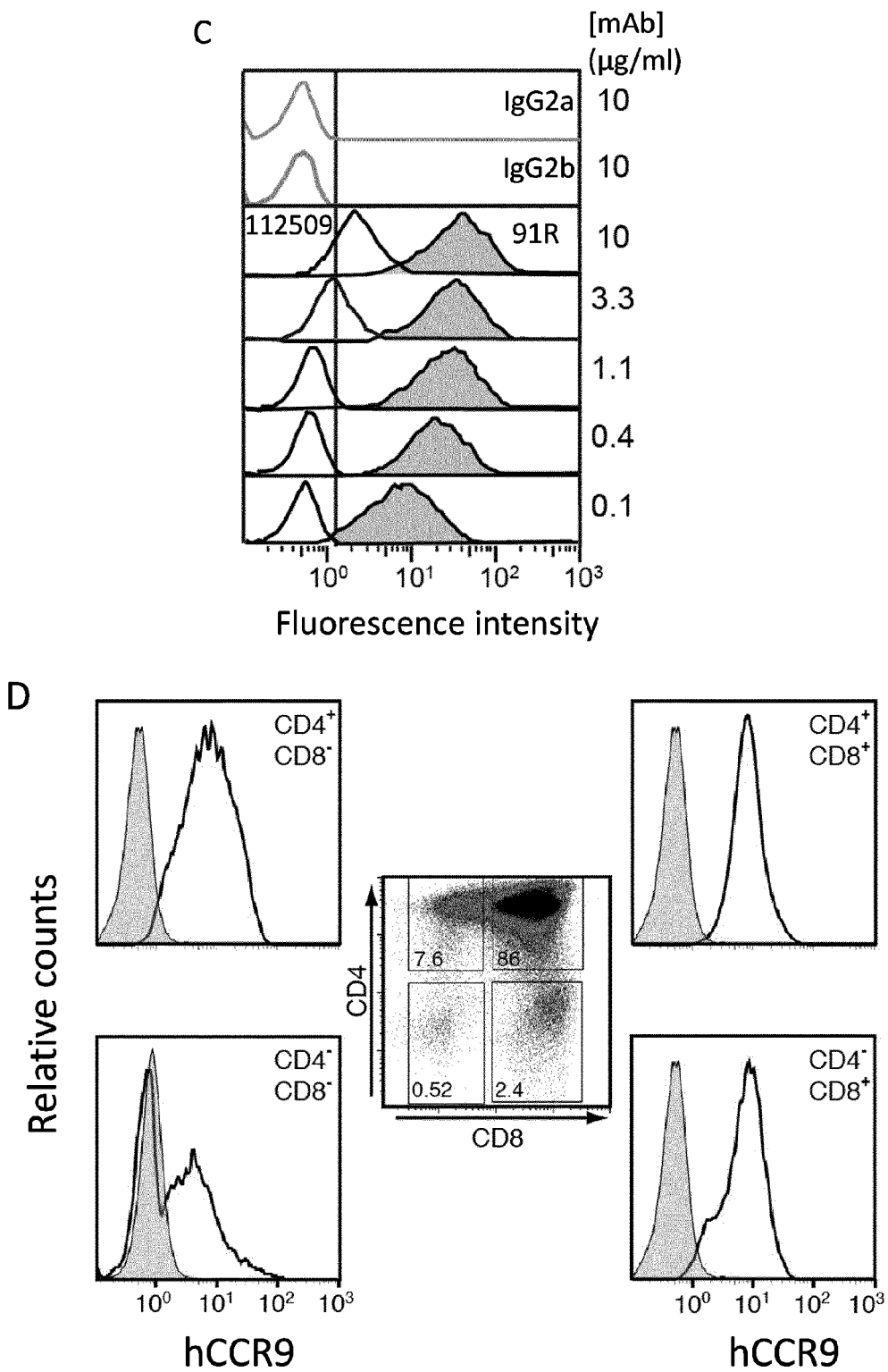
Figure 1:
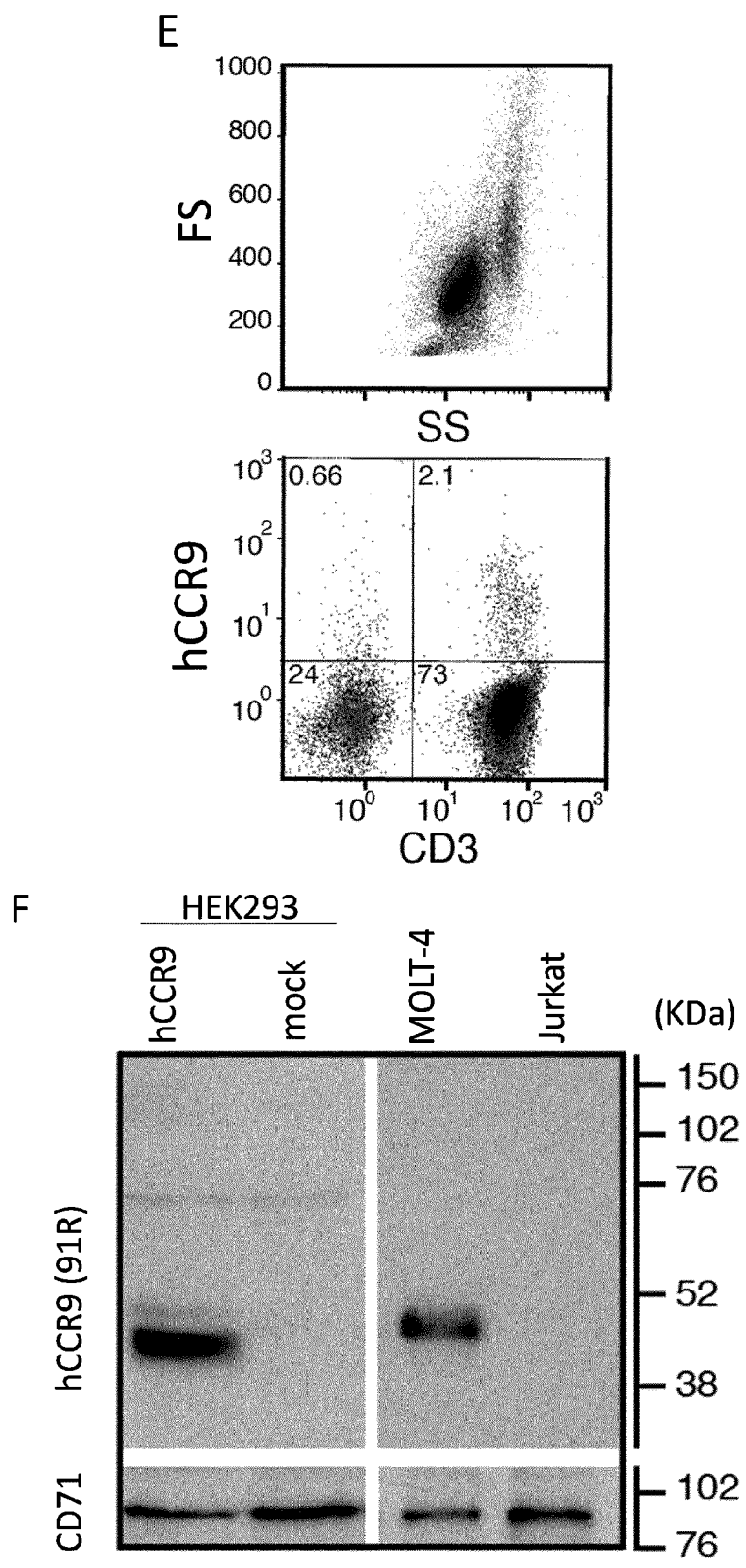

The invention provides an antibody binding specifically to CCR9, or an antigen-binding fragment thereof, hereinafter "antibody of the invention", comprising
i) a heavy chain comprising at least one complementarity determining region (CDR) selected from:
a CDR comprising the amino acid sequence shown in SEQ ID NO: 1 (NFWMN) [CDR-H1] or a variant thereof;
a CDR comprising the amino acid sequence shown in SEQ ID NO: 2 (EIRLKSNNYATHYAESVKG) [CDR-H2] or a variant thereof; and
a CDR comprising the amino acid sequence shown in SEQ ID NO: 3 (DGWFAY) [CDR-H3] or a variant thereof; and
ii) a light chain comprising at least one complementarity determining region (CDR) selected from:
a CDR comprising the amino acid sequence shown in SEQ ID NO: 4 (RSSQSLLHSNGNTYVQ) [CDR-L1] or a variant thereof;
a CDR comprising the amino acid sequence shown in SEQ ID NO: 5 (KVSNRFP) [CDR-L2] or a variant thereof; and
a CDR comprising the amino acid sequence shown in SEQ ID NO: 6 (AQSTHVPRT) [CDR-L3] or a variant thereof.

In a particular embodiment, the antibody of the invention comprises within the heavy chain two of said CDRs selected from the CDRs comprising the amino acid sequences shown in SEQ ID NOs: 1 to 3 or variants thereof.

In another particular embodiment, the antibody of the invention comprises within the heavy chain a CDR comprising the amino acid sequence shown in SEQ ID NO: 1 [CDR-H1] or a variant thereof, a CDR comprising the amino acid sequence shown in SEQ ID NO: 2 [CDR-H2] or a variant thereof, and a CDR comprising the amino acid sequence shown in SEQ ID NO: 3 [CDR-H3] or a variant thereof.

In a preferred embodiment, the antibody of the invention comprises within the heavy chain a CDR consisting of the amino acid sequence shown in SEQ ID NO: 1 [CDR-H1], a CDR consisting of the amino acid sequence shown in SEQ ID NO: 2 [CDR-H2], and a CDR consisting of the amino acid sequence shown in SEQ ID NO: 3 [CDR-H3].

In another particular embodiment, the antibody of the invention comprises within the light chain two of said CDRs selected from the CDRs comprising the amino acid sequences shown in SEQ ID NOs: 4 to 6 or variants thereof.

In another particular embodiment, the antibody of the invention comprises within the light chain a CDR comprising the amino acid sequence shown in SEQ ID NO: 4 [CDR-L1] or a variant thereof, a CDR comprising the amino acid sequence shown in SEQ ID NO: 5 [CDR-L2] or a variant thereof, and a CDR comprising the amino acid sequence shown in SEQ ID NO: 6 [CDR-L3] or a variant thereof.

In another particular embodiment, the antibody of the invention comprises within the light chain a CDR consisting of the amino acid sequence shown in SEQ ID NO: 4 [CDR-L1], a CDR consisting of the amino acid sequence shown in SEQ ID NO: 5 [CDR-L2], and a CDR consisting of the amino acid sequence shown in SEQ ID NO: 6 [CDR-L3].

The antibody of the invention can contain any combination of CDR sequences, the characteristics of which have been mentioned previously; nevertheless, in a preferred embodiment, the antibody of the invention comprises within the heavy chain a CDR-H1 comprising the amino acid sequence shown in SEQ ID NO: 1, a CDR-H2 comprising the amino acid sequence shown in SEQ ID NO: 2, and a CDR-H3 comprising the amino acid sequence shown in SEQ ID NO: 3, and comprises within the light chain a CDR-L1 comprising the amino acid sequence shown in SEQ ID NO: 4, a CDR-L2 comprising the amino acid sequence shown in SEQ ID NO: 5, and a CDR-L3 comprising the amino acid sequence shown in SEQ ID NO: 6.

In a more preferred embodiment, the antibody of the invention comprises within the heavy chain a CDR-H1 consisting of the amino acid sequence shown in SEQ ID NO: 1, a CDR-H2 consisting of the amino acid sequence shown in SEQ ID NO: 2, and a CDR-H3 consisting of the amino acid sequence shown in SEQ ID NO: 3, and comprises within the light chain a CDR-L1 consisting of the amino acid sequence shown in SEQ ID NO: 4, a CDR-L2 consisting of the amino acid sequence shown in SEQ ID NO: 5, and a CDR-L3 consisting of the amino acid sequence shown in SEQ ID NO: 6, which corresponds to the antibody identified as 91R mAb in the examples.

In another particular embodiment, the antibody of the invention comprises within the heavy chain two of said CDRs selected from the CDRs comprising the amino acid sequences shown in SEQ ID NOs: 7, 2 and 3 or variants thereof.

In another particular embodiment, the antibody of the invention comprises within the heavy chain a CDR comprising the amino acid sequence shown in SEQ ID NO: 7 (KFWMN) [CDR-H1] or a variant thereof, a CDR comprising the amino acid sequence shown in SEQ ID NO: 2 [CDR-H2] or a variant thereof, and a CDR comprising the amino acid sequence shown in SEQ ID NO: 3 [CDR-H3] or a variant thereof.

In another preferred embodiment, the antibody of the invention comprises within the heavy chain a CDR consisting of the amino acid sequence shown in SEQ ID NO: 7 [CDR-H3], a CDR consisting of the amino acid sequence shown in SEQ ID NO: 2 [CDR-H2], and a CDR consisting of the amino acid sequence shown in SEQ ID NO: 3 [CDR-H3].

In another particular embodiment, the antibody of the invention comprises within the light chain two of said CDRs selected from the CDRs comprising the amino acid sequences shown in SEQ ID NOs: 8 to 10 or variants thereof.

In another particular embodiment, the antibody of the invention comprises within the light chain a CDR comprising the amino acid sequence shown in SEQ ID NO: 8 (RSSQSLVHSNGNTYLN) [CDR-L1] or a variant thereof, a CDR comprising the amino acid sequence shown in SEQ ID NO: 9 (KVSNRFS) [CDR-L2] or a variant thereof, and a CDR comprising the amino acid sequence shown in SEQ ID NO: 10 (SQSTHFPRT) [CDR-L3] or a variant thereof.

In another particular embodiment, the antibody of the invention comprises within the light chain a CDR consisting of the amino acid sequence shown in SEQ ID NO: 8 [CDR-L1], a CDR consisting of the amino acid sequence shown in SEQ ID NO: 9 [CDR-L2], and a CDR consisting of the amino acid sequence shown in SEQ ID NO: 10 [CDR-L3].

The antibody of the invention can contain any combination of CDR sequences, the characteristics of which have been mentioned previously; nevertheless, in a preferred embodiment, the antibody of the invention comprises within the heavy chain a CDR-H1 comprising the amino acid sequence shown in SEQ ID NO: 7, a CDR-H2 comprising the amino acid sequence shown in SEQ ID NO: 2, and a CDR-H3 comprising the amino acid sequence shown in SEQ ID NO: 3, and comprises within the light chain a CDR-L1 comprising the amino acid sequence shown in SEQ ID NO: 8, a CDR-L2 comprising the amino acid sequence shown in SEQ ID NO: 9, and a CDR-L3 comprising the amino acid sequence shown in SEQ ID NO: 10.

In a more preferred embodiment, the antibody of the invention comprises within the heavy chain a CDR-H1 consisting of the amino acid sequence shown in SEQ ID NO: 7, a CDR-H2 consisting of the amino acid sequence shown in SEQ ID NO: 2, and a CDR-H3 consisting of the amino acid sequence shown in SEQ ID NO: 3, and comprising within the light chain a CDR-L1 consisting of the amino acid sequence shown in SEQ ID NO: 8, a CDR-L2 consisting of the amino acid sequence shown in SEQ ID NO: 9, and a CDR-L3 consisting of the amino acid sequence shown in SEQ ID NO: 10, which corresponds to the antibody identified as 92R mAb in the examples.

The term "antibody", as used herein, refers to a glycoprotein that exhibits specific binding activity for a particular protein, which is referred to as "antigen". The term "antibody" comprises whole monoclonal antibodies or polyclonal antibodies, or fragments thereof, and includes human antibodies, humanised antibodies, chimeric antibodies and antibodies of a non-human origin. "Monoclonal antibodies" are homogenous, highly specific antibody populations directed against a single site or antigenic "determinant". "Polyclonal antibodies" include heterogeneous antibody populations directed against different antigenic determinants.

In a particular embodiment, the antibody of the invention is an antibody of non-human origin, preferably of murine origin. In another particular embodiment, the antibody of the invention is a monoclonal antibody. In another particular embodiment, the antibody of the invention is a polyclonal antibody.

The antibody of the invention can be of any isotype. The choice of isotype typically will be guided by the desired effector functions, such as ADCC induction. Exemplary isotypes are IgG1, IgG2, IgG3, and IgG4. Either of the human light chain constant regions, kappa or lambda, may be used. If desired, the class of a CCR9 antibody of the present invention may be switched by known methods.

In another particular embodiment, the antibody of the invention is an antibody of human origin or a humanised antibody.

The antibody of the invention binds specifically to CCR9. The term "CCR9" or "CCR9 chemokine receptor", as used herein, refers to the chemokine (C-C motif) receptor 9. Other terms to designate CCR9 include GPR28; CDw199; GPR-9-6; CC-CKR-9. The specific ligand of CCR9 is CCL25. The chemokine receptor CCR9 is expressed on most small intestinal lamina propria and intraepithelial lymphocytes and on a small subset of peripheral blood lymphocytes. This receptor is expressed on the majority of thymocytes, small intestinal lamina propria and intraepithelial lymphocytes, on a small subset of peripheral blood lymphocytes and in a subset of memory T cells $\alpha_4\beta_7$ present in the circulation. It is also expressed on IgA secreting B cells, macrophages and plasmacytoid dendritic cells. CCR9 expression has been reported in T cell acute lymphoblastic leukaemia cells, prostate cancer cells, breast cancer cells, ovarian cancer cells, pancreatic cancer cells and melanoma cells. CCR9 positive cells are crucial in the pathogenesis of acute liver inflammation, inflammatory bowel disease and Crohn's disease. Two alternatively spliced transcript variants have been described for the gene encoding CCR9, resulting in CCR9 isoform A and CCR9 isoform B, with Swiss-Prot accession numbers NP_112477.1 and NP_001243298.1 respectively, at 20 Sep. 2013.

CCR9 is organized into 15 domains, corresponding to an N-terminal extracellular domain (Nt), seven transmembrane domains, three intracellular domains, three extracellular domains and an intracellular C-terminal domain (Ct) (FIG. 2A). In a particular embodiment, the antibody of the invention binds specifically to an epitope containing amino acids 2-22 from the N-terminal extracellular domain (Nt) of CCR9 isoform A (SEQ ID NO: 11)

The antibody of the invention may be directed to CCR9 antigens from various mammalian species. Non-limitative examples of mammals suitable for this invention include mouse, rat, rabbit, goat, donkey, or non-human primate such as monkey (e.g., cynomologous or rhesus monkey) or ape (e.g., chimpanzee) and human. In a particular embodiment, the CCR9 is of human origin.

It is well known that the basic structural unit of an antibody comprises a tetramer. Each tetramer is constituted by two identical pairs of polypeptide chains, each of which is composed by a light chain (25 KDa) and by a heavy chain (50-75 KDa). The amino-terminal region of each chain includes a variable region of about 100-110 or more amino acids, which is involved in antigen recognition. The carboxy-terminal region of each chain comprises the constant region that mediates the effector function. The variable regions of each pair of light and heavy chains form the binding site of the antibody. Therefore, an intact antibody has two binding sites. Light chains are classified as κ or λ. Heavy chains are classified as γ, μ, α, δ and ε, and they define the isotype of the antibody as respectively IgG, IgM, IgA, IgD or IgE.

The variable regions of each pair of light and heavy chains form the binding site of the antibody. They are characterized by the same general structure constituted by relatively preserved regions called frameworks (FR) joined by three hyper-variable regions called complementarity determining regions (CDR) (Kabat et al., 1991, Sequences of Proteins of Immunological Interest, 5th ed., NIH Publication No. 91-3242, Bethesda, Md.; Chothia and Lesk, 1987, J Mol Biol 196:901-17). The term "complementarity determining region" or "CDR", as used herein, refers to the region within an antibody where this protein complements an antigen's shape. Thus, CDRs determine the protein's affinity (roughly, bonding strength) and specificity for specific antigens. The CDRs of the two chains of each pair are aligned by the framework regions, acquiring the function of binding a specific epitope. Consequently, both the heavy chain and the light chain are characterized by three CDRs, respectively CDRH1, CDRH2, CDRH3 and CDRL1, CDRL2, CDRL3.

The CDR sequences can be determined according to conventional criteria, for example by means of the criteria of IgBLAST: (Ye et al., 2013, Nucleic Acids Res 41 (available on the World Wide Web site of the National Center for Biotechnology Information of the United States, ncbi<<dot>>nlm<<dot>>nih<<dot>>gov<<slash>>igblast<<slash>>; Web Server issue:W34-40), by following the numbering provided by Kabat et al., Sequences of Proteins of Immunological Interest, 5th ed., Public Health Service, National Institutes of Health, Bethesda, Md. (1991), as is used in the present application, or by following the numbering provided by Chothia et al. (1989, Nature 342: 877-83).

As used herein, the antibody of the invention encompasses not only full length antibodies (e.g., IgG), but also antigen-binding fragments thereof, for example, Fab, Fab', F(ab')$_2$, Fv fragments, human antibodies, humanised antibodies, chimeric antibodies, antibodies of a non-human origin, recombinant antibodies, and polypeptides derived from immunoglobulins produced by means of genetic engineering techniques, for example, single chain Fv (scFv), diabodies, heavy chain or fragments thereof, light chain or fragment thereof, $V_H$ or dimers thereof, $V_L$ or dimers thereof, Fv fragments stabilized by means of disulfide bridges (dsFv), molecules with single chain variable region domains (Abs), minibodies, scFv-Fc, and fusion proteins comprising an antibody, or any other modified configuration of the immunoglobulin molecule that comprises an antigen recognition site of a desired specificity. The antibody of the invention may also be a bispecific antibody. An antibody fragment may refer to an antigen binding fragment. An antibody includes an antibody of any class, namely IgA, IgD, IgE, IgG (or sub-classes thereof), and IgM, and the antibody need not be of any particular class. In addition, the antibody of the invention may be also conjugated to a further compound, such as a therapeutic agent, a toxin and the like.

Numerous approaches make use of the molecular biology and genetic techniques such as the good knowledge of the genetics and structure of the immunoglobulins to construct different modifications of immunoglobulin molecule with the aim of improve its properties for clinical or other uses. Some of them tend to reduce the immunogenicity of the molecule in the species in which should be used and the resultant molecule has a sequence more homologous with this species. Various methods have been used to obtain mAbs of human origin avoiding the non-ethically admissible proceedings in healthy humans. In other approaches the molecular weight and size are reduced e.g. in order to improve the distribution of the molecule into solid tumours. Other possibilities are conjugation in a molecule of binding domains for more than one target molecule (bispecific antibody or also triespecific, etc.) or the conjugation of an antibody or a fragment with another molecule with the desired function e.g. a toxic agent, a hormone, growth factor, a immunomodulating agent (immunosuppressor or immunostimulator), an inhibitor of cell growth, etc. In general all the resultant molecules retain at least one variable domain of an antibody, which gives the high specificity and affinity characteristic of the antigen-antibody binding.

Such antibodies may be produced in a variety of ways, including hybridoma cultures, recombinant expression in bacteria or mammalian cell cultures, and recombinant expression in transgenic animals. There is abundant guidance in the literature for selecting a particular production methodology, e.g., Chadd and Chamow, Curr. Opin. Biotechnol., 12:188-194 (2001). The choice of manufacturing methodology depends on several factors including the antibody structure desired, the importance of carbohydrate moieties on the antibodies, ease of culturing and purification, and cost. Many different antibody structures may be generated using standard expression technology, including full-length antibodies, antibody fragments, such as Fab and Fv fragments, as well as chimeric antibodies comprising components from different species. Antibody fragments of small size, such as Fab and Fv fragments, having no effector functions and limited pharmokinetic activity may be generated in a bacterial expression system. Single chain Fv fragments show low immunogenicity and are cleared rapidly from the blood.

In a particular embodiment, the antibody of the invention is a monoclonal antibody or a fragment of said antibody which retains the capacity to bind to CCR9. Said antibodies are preferably human or humanised antibodies.

Thus, in a particular embodiment, the antibody of the invention is a human antibody. In another particular embodiment, the antibody of the invention is a humanised antibody. In another particular embodiment, the antibody of the invention is a chimeric antibody.

Humanised Antibodies:

By "humanised antibody" is meant an antibody derived from a non-human antibody, typically a murine antibody, that retains the antigen-binding properties of the parent antibody, but which is less immunogenic in humans. This may be achieved by various methods, including (a) grafting the entire non-human variable domains onto human constant regions to generate chimeric antibodies; (b) grafting only the non-human complementarity determining regions (CDRs) into human framework and constant regions with or without retention of critical framework residues; and (c) transplanting the entire non-human variable domains, but "cloaking" them with a human-like section by replacement of surface residues.

Methods for humanizing non-human antibodies have been described in the art. Preferably, a humanised antibody has one or more amino acid residues introduced into it from a source which is non-human. These non-human amino acid residues are often referred to as "import" residues, which are typically taken from an "import" variable domain.

Humanisation can be essentially performed following the method of Winter and co-workers (Jones et al., Nature, 321:522-525 (1986); Reichmann et al., Nature, 332:323-327 (1988); Verhoeyen et al., Science, 239:1534-1536 (1988)), by substituting hypervariable region sequences for the corresponding sequences of a human antibody. In practice, humanised antibodies are typically human antibodies in which some hypervariable region residues and possibly some framework region (FR) residues are substituted by residues from analogous sites in rodent antibodies. The choice of human variable domains, both light and heavy, to be used in making the humanised antibodies is very important to reduce immunogenicity retaining the specificity and affinity for the antigen. According to the so called "best-fit" method, the sequence of the variable domain of a rodent antibody is screened against the entire library of known human variable-domain sequences. The human sequence which is closest to that of the rodent is then accepted as the human framework region (FR) for the humanised antibody (Suns et al., J. Immunol., 151:2296 (1993); Chothia et al., J. Mol. Biol, 196:901 (1987)). Another method uses a particular framework region derived from the consensus sequence of all human antibodies of a particular subgroup of light or heavy chains. The same framework may be used for several different humanised antibodies (Carter et al., Proc. Natl. Acad. Sci. USA, 89:4285 (1992); Presta et al., J. Immunol., 151:2623 (1993)).

It is further important that antibodies are humanised, with retention of high affinity for the antigen and other favourable biological properties. To achieve this goal, according to a preferred method, humanised antibodies are prepared by a process of analysis of the parental sequences and various conceptual humanised products using three-dimensional models of the parental and humanised sequences.

A further step in this approach, to make an antibody more similar to humans, is to prepare the so called primatised antibodies, i.e. a recombinant antibody which has been engineered to contain the variable heavy and light domains of a monkey (or other primate) antibody, in particular, a cynomolgus monkey antibody, and which contains human constant domain sequences, preferably the human immunoglobulin gamma 1 or gamma 4 constant domain (or PE variant). The preparation of such antibodies is described in Newman et al., Biotechnology, 10: 1458-1460 (1992); U.S. Pat. No. 5,658,570 and U.S. Pat. No. 6,113,898. These antibodies have been reported to exhibit a high degree of homology to human antibodies, i.e., 85-98%, display human effector functions, have reduced immunogenicity, and may exhibit high affinity to human antigens. Another highly efficient means for generating recombinant antibodies is disclosed by Newman, Biotechnology, 10: 1455-1460 (1992).

Human Antibodies:

By "human antibody" is meant an antibody containing entirely human light and heavy chains as well as constant regions, produced by any of the known standard methods.

As an alternative to humanization, human antibodies can be generated. For example, it is now possible to produce transgenic animals (e.g., mice) that are capable, upon immunization, of producing a full repertoire of human antibodies in the absence of endogenous immunoglobulin production. For example, it has been described that the homozygous deletion of the antibody heavy-chain joining region PH gene in chimeric and germ-line mutant mice results in the complete inhibition of endogenous antibody production. Transfer of the human germ-line immunoglobulin gene array in such germ line mutant mice will result in the production of human antibodies after immunization. See, e.g., Jakobovits et al., Proc. Mad. Acad. Sci. USA, 90:255 1 (1993); Jakobovits et al., Nature, 362:255-258 (1993), Lonberg, 2005, Nature Biotech. 23:1117-25.

Human antibodies may also be generated by in vitro activated B cells or SCID mice with its immune system reconstituted with human cells.

Once a human antibody is obtained, its coding DNA sequences can be isolated, cloned and introduced into an appropriate expression system, i.e., a cell line, preferably from a mammal, which subsequently express and liberate it into a culture media from which the antibody can be isolated.

Antibody Fragments:

An antibody fragment is a fragment of an antibody such as, for example, Fab, F(ab')$_2$, Fab' and scFv. Various techniques have been developed for the production of antibody fragments. Traditionally, these fragments were derived via proteolytic digestion of intact antibodies but more recently these fragments can be produced directly by recombinant host cells. In other embodiments, the antibody of choice is a single chain Fv (scFv) fragment which additionally may be monospecific or bispecific.

Papain digestion of antibodies produces two identical antigen-binding fragments, called "Fab" fragments, each with a single antigen-binding site, and a residual "Fc" fragment, which name reflects its ability to crystallize readily. Pepsin treatment yields an F(ab')$_2$ fragment that has two antigen-binding sites and is still capable of cross-linking antigen.

"Fv" is the minimum antibody fragment which contains a complete antigen-recognition and antigen-binding site. This region consists of a dimer of one heavy chain and one light chain variable domain in tight, non-covalent association. It is in this configuration that the three hypervariable regions of each variable domain interact to define an antigen-binding site on the surface of the $V_H$-$V_L$ dimer. Collectively, the six hypervariable regions confer antigen-binding specificity to the antibody. However, even a single variable domain (or half of an Fv comprising only three hypervariable regions specific for an antigen) has the ability to recognize and bind the antigen, although with lower affinity than the entire binding site.

The Fab fragment also contains the constant domain of the light chain and the first constant domain (CHI) of the heavy chain. Fab' fragments differ from Fab fragments by the addition of a few residues at the carboxy terminus of the heavy chain CH1 domain including one or more cysteines from the antibody hinge region. Fab'-SH is the designation herein for Fab' in which the cysteine residue(s) of the constant domains bear at least one free thiol group. F(ab')Z antibody fragments originally were produced as pairs of Fab' fragments which have hinge cysteines between them. Other chemical couplings of antibody fragments are also known.

"Single-chain Fv" or "scFv" antibody fragments comprise the $V_H$ and $V_L$ domains of an antibody, wherein these domains are present in a single polypeptide chain. Preferably, the Fv polypeptide further comprises a polypeptide linker between the VH and VL domains which enables the scFv to form the desired structure for antigen binding. For a review of scFv see Pluckthun in The Pharmacology of Monoclonal Antibodies, vol. 113, Rosenburg and Moore eds., Springer-Verlag, N.Y., pp. 269-315 (1994).

The term "diabodies" refers to small antibody fragments with two antigen-binding sites, those fragments comprising a heavy-chain variable domain ($V_H$) connected to a light chain variable domain ($V_L$) in the same polypeptide chain ($V_H$-$V_L$). By using a linker that is too short to allow pairing between the two domains on the same chain, the domains are forced to pair with the complementary domains of another chain and create two antigen-binding sites. Diabodies are described more fully in, for example, EP 404,097; WO 93/11161; and Hollinger et al., Proc. Natl. Acad. Sci. USA, 90:6444-6448 (1993).

Functional fragments of antibodies which bind to CCR9 included within the present invention retain at least one binding function and/or modulation function of the full-length antibody from which they are derived. Preferred functional fragments retain an antigen-binding function of a corresponding full-length antibody (e.g., the ability to bind a mammalian CCR9).

Bispecific Antibodies:

Bispecific antibodies are antibodies that have binding specificities for at least two different epitopes. Exemplary bispecific antibodies may bind to two different epitopes of the CCR9. Other such antibodies may bind CCR9 and further bind a second cell surface marker. Bispecific antibodies may also be used to localize cytotoxic agents to the CCR9-expressing cells. These antibodies possess an anti-CCR9-binding arm and an arm which binds the cytotoxic agent (e.g. saporin, anti-interferon-α, vinca alkaloid, ricin A chain, methotrexate or a radioactive isotope). Bispecific antibodies can be prepared as full length antibodies or antibody fragments (e.g. F(ab)$_2$ bispecific antibodies, minibodies, diabodies).

According to a different approach, antibody variable domains with the desired binding specificities (antibody-antigen combining sites) are fused to immunoglobulin constant domain sequences. The fusion preferably is with an immunoglobulin heavy chain constant domain, comprising at least part of the hinge, CH2, and CH3 regions. It is preferred to have the first heavy-chain constant region (CHI) containing the site necessary for light chain binding, present in at least one of the fusions. DNAs encoding the immunoglobulin heavy chain fusions and, if desired, the immunoglobulin light chain, are inserted into separate expression vectors, and are co-transfected into a suitable host organism. This provides great flexibility in adjusting the mutual proportions of the three polypeptide fragments in embodiments when unequal ratios of the three polypeptide chains used in the construction provide the optimum yields. It is, however, possible to insert the coding sequences for two or all three polypeptide chains in one expression vector when the expression of at least two polypeptide chains in equal ratios results in high yields or when the ratios are of no particular significance.

Techniques for generating bispecific antibodies from antibody fragments have also been described in the literature. For example, bispecific antibodies can be prepared using chemical linkage.

The fragments with the capacity to bind to CCR9 can also be obtained by conventional methods known by persons having ordinary skill in the art. Said methods can involve isolating DNA that encodes the polypeptide chains (or a fragment thereof) of a monoclonal antibody of interest and manipulating DNA by means of recombinant DNA technology. DNA can be used to generate another DNA of interest, or an altered DNA, (for example by means of mutagenesis) for adding, removing or substituting one or more amino acids, for example, the DNA that encodes the polypeptide chains of an antibody (e.g., the heavy or light chains, the variable region or the whole antibody) can be isolated from murine B cells from immunized mice with CCR9. The DNA can be isolated and amplified by conventional methods, for example by means of PCR.

The single-chain antibodies can be obtained by conventional methods by binding the variable region of the heavy and light chains (Fv region) by means of an amino acid bridge. The scFvs can be prepared by fusing the DNA encoding a linker peptide between the DNAs encoding the polypeptides of the variable regions ($V_L$ and $V_H$). The production of scFvs is described in a number of documents, for example, in U.S. Pat. No. 4,946,778, Bird (Science 242: 423, 1988), Huston et al. (Proc. Natl. Acad Sci USA 85: 5879, 1988) and Ward et al. (Nature 334: 544, 1989).

The person skilled in the art will understand that the amino acid sequences of the antibodies of the invention can include one or more amino acid substitutions such that, even though the primary sequence of the polypeptide is altered, the capacity of the antibody to bind to CCR9 is maintained. Said substitution can be a conservative substitution and is generally applied to indicate that the substitution of one amino acid with another amino acid with similar properties (for example, the substitution of glutamic acid (negatively charged amino acid) with aspartic acid would be a conservative amino acid substitution).

The present invention also contemplates variants of the sequences of the CDRs of the heavy and light chains identified in this description, which fall within the scope of the present invention. As it is used herein, the term "variant" or "functional variant", as used herein, refers to a substantially similar sequence that substantially maintains its capacity to bind to its cognate antigen, i.e., its affinity/avidity and/or the specificity/selectivity. The variants generally have the same biological activity from the qualitative viewpoint as the native sequence. A variant of a CDR can be a polypeptide sequence derivative identified in this description comprising the addition, deletion or substitution of one or more amino acids. According to the invention, variants of a CDR comprising the amino acid sequence shown in one of SEQ ID NO: 1 to 10 include CDRs comprising amino acid sequences having at least approximately 70% sequence identity with the corresponding amino acid sequence shown in one of SEQ ID NOs: 1 to 10, preferably at least 75%, 80%, 85%, 90%, 91%, 92%, 93%, 94%, 95%, 96%, 97%, 98% or 99% sequence identity with the corresponding amino acid sequences shown in one of SEQ ID NOs: 1 to 10. It is also contemplated that variants comprise additions consisting of at least 1 amino acid, or at least 2 amino acids, or at least 3 amino acids, or at least 4 amino acids, or at least 5 amino acids, or at least 6 amino acids, or at least 7 amino acids, or at least 8 amino acids, or at least 9 amino acids, or at least 10 amino acids or more amino acids at the N-terminus, or the C-terminus, or both the N- and C-terminus of the CDR. Likewise, it is also contemplated that variants comprise deletions consisting of at least 1 amino acid, or at least 2 amino acids, or at least 3 amino acids, or at least 4 amino acids, or at least 5 amino acids, or at least 6 amino acids, or at least 7 amino acids, or at least 8 amino acids, or at least 9 amino acids, or at least 10 amino acids or more amino acids at the N-terminus, or the C-terminus, or both the N- and C-terminus of the CDR. Functional variants of an antibody according to the invention will preferably have a capacity to bind to its cognate target of at least 50%, at least 60%, at least 70%, at least 80%, at least 90%, at least 91%, at least 92%, at least 93%, at least 94%, at least 95%, at least 96%, at least 97%, at least 98%, or at least 99% the capacity to bind to its cognate target of said antibody.

The capacity of the antibody of the invention to bind to CCR9 can be determined by a number of assays that are available in the art. Preferably, the binding specificity of monoclonal antibodies produced by a clone of hybridoma cells is determined by immunoprecipitation or by an in vitro binding assay, such as radioimmunoassay (RIA), enzyme-linked immunoabsorbent assay (ELISA), surface plasmon resonance or by immunofluorescent techniques such as immunohistochemistry (IHC), fluorescence microscopy or flow cytometry.

Amino acid sequence modification(s) of the antibody described herein are contemplated. For example, it may be desirable to improve the binding affinity and/or other biological properties of the antibody. Amino acid sequence variants of the antibody are prepared by introducing appropriate nucleotide changes into the antibody encoding nucleic acid, or by peptide synthesis. Such modifications include, for example, deletions from, and/or insertions into and/or substitutions of, residues within the amino acid sequences of the antibody. Any combination of deletion, insertion, and substitution is made to achieve the final construct, provided that the final construct possesses the desired characteristics. The amino acid changes may also alter post-translational processes of the protein, such as changing the number or position of glycosylation sites.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include a peptide with an N-terminal methionyl residue or the antibody polypeptidic chain fused to a cytotoxic polypeptide. Other insertional variants of the molecule include the fusion to the N- or C-terminus of an enzyme, or a polypeptide which increases its serum half-life.

Another type of variant is an amino acid substitution variant. These variants have at least one amino acid residue in the molecule replaced by a different residue. The sites of greatest interest for substitution mutagenesis of antibodies s include the hypervariable regions, but FR alterations are also contemplated.

Another type of amino acid variant of the antibody alters the original glycosylation pattern of the antibody. By altering is meant deleting one or more carbohydrate moieties found in the molecule, and/or adding one or more glycosylation sites that are not present in it. Glycosylation of polypeptides is typically either N-linked or O-linked. N-linked refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of any of these tripeptide sequences in a polypeptide creates a potential glycosylation site. O-linked glycosylation refers to the attachment of one of the monosaccharides or monosaccharide dereivatives N-aceylgalactosamine, galactose, or xylose to a hydroxyamino acid, most commonly serine or threonine, although 5-hydroxyproline or 5-hydroxylysine may also be used. Addition of glycosylation sites to the antibody is conveniently accomplished by altering the amino acid sequence such that it contains one or more of the above-described tripeptide sequences (for N-linked glycosylation sites). The alteration may also be made by the addition of, or substitution by, one or more serine or threonine residues to the sequence of the original antibody (for O-linked glycosylation sites). Nucleic acid molecules encoding amino acid sequence variants of the antibody are prepared by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier prepared variant or a non-variant version of the antibody.

It may be desirable to modify the antibodies used in the invention to improve effector function, e.g. so as to enhance ADCC and/or CDC of the antibody. This may be achieved by introducing one or more amino acid substitutions in an Fc region of an antibody.

Glycosyl groups added to the aminoacid backbone of glycoproteins e.g. antibodies are formed by several monosaccharides or monosaccharide derivatives in resulting in a composition which can be different in the same antibody produced in cell from different mammals or tissues. In addition, it has been shown that different composition of glycosil groups can affect the potency in mediating antigen-dependent cell-mediated cyotoxicity (ADCC) and/or complement dependent cytotoxicity (CDC) of the antibody. Therefore it is possible to improve those properties by mean of studying the pattern of glycosilation of antibodies from different sources. An example of such approach is Niwa et al., Cancer Res. 2004 Mar. 15; 64(6):2127-33.

Thus, in another particular embodiment, the antibody of the invention is glyco-engineered to reduce fucose and thus enhance ADCC. Antibodies lacking fucosyl residues can be prepared according to U.S. Pat. No. 8,207,303.

In another particular embodiment, the antibody of the invention has been engineered to enhance complement activation.

Alternatively or additionally, cysteine residue(s) may be introduced in the Fc region, thereby allowing interchain disulfide bond formation in this region. The homodimeric antibody thus generated may have improved internalization capability and/or increased complement-mediated cell killing and antibody-dependent cellular cytotoxicity (ADCC). See Caron et al., J. Exp Med. 176:1191-1195 (1992) and Shopes, B. J. Immunol. 148:2918-2922 (1992). Homodimeric antibodies with enhanced anti-tumour activity may also be prepared using heterobifunctional cross-linkers as described in Wolff et al. Cancer Research 53:2560-2565 (1993). Alternatively, an antibody which has dual Fc regions can be engineered and may thereby have enhanced complement lysis and ADCC capabilities. See Stevenson et al. Anti-Cancer Drug Design 3:2 19-230 (1989), and Davis et al., Protein Eng Des Sel 23:195-202 (2010).

In order to increase the serum half-life of the antibody, one may incorporate a salvage receptor binding epitope into the antibody (especially an antibody fragment) as described in U.S. Pat. No. 5,739,277, for example. As used herein, the term "salvage receptor binding epitope" refers to an epitope of the Fc region of an IgG molecule (e.g., IgGI, IgG2, IgG3, or IgG4) that is responsible for increasing the in vivo serum half-life of the IgG molecule.

Preferably, the antibody of the invention, e.g., monoclonal antibodies, scFv fragments, Fab fragments, or other binding compositions derived from the monoclonal antibody of the invention, have a high affinity to CCR9 receptor. The affinity of monoclonal antibodies and related molecules to CCR9 receptor may be measured by conventional techniques.

The affinity of an antibody for an antigen can be defined as the effectiveness of the antibody for binding such antigen. Antigen-antibody binding is a reversible binding and so, when both molecules are in dilution in the same solution after sufficient time, this solution reaches an equilibrium in which the concentrations of antigen-antibody complex (AgAb), free antigen (Ag) and free antibody (Ab) are constant. Therefore the ratio [AgAb]/[Ag]*[Ab] is also a constant defined as association constant named Ka which can be used to compare the affinity of some antibodies for its respective epitope.

The common way to measure the affinity is to experimentally determine a binding curve. This involves measuring the amount of antibody-antigen complex as a function of the concentration of the free antigen. There are two common methods of performing this measurement: (i) the classical equilibrium dialysis using Scatchard analysis and (ii) the surface plasmon resonance method in which either antibody or antigen are bound to a conductive surface and binding of antigen or antibody respectively affects the electrical properties of this surface.

Often it is only necessary to determine relative affinities of two or more antibodies that join the same epitope, such as in the case of the antibody of the invention and a functional variant thereof. In this case a competitive assay can be performed in which a serial dilution of one of the antibodies is incubated with a constant quantity of a ligand, and the second antibody labelled with any suitable tracer is then added. After binding of this mAb and washing the non-bounded antibodies, the concentration of second antibody is measured and plotted in relation to concentrations of the first antibody and analysed with Scatchard method. An example is Tamura et al., J. Immunol. 163: 1432-1441 (2000). Alternatively, when the ligand is a membrane bound antigen as is the case of the present invention, the soluble ligand may be displayed to the antibodies on the surface of cells expressing said antigen. Therefore, varying quantities of antibodies are incubated with a constant quantity of a ligand.

The affinity of the antibody of the invention for CCR9 is at least $10^{-7}$ M, at least $10^{-8}$ M, at least $10^{-9}$ M, at least $10^{-10}$ M, at least $10^{-11}$ M or at least $10^{-12}$ M.

Nucleic Acids, Expression Cassettes, Vectors and Cells of the Invention

In another aspect, the present invention relates to a nucleic acid, hereinafter the "nucleic acid of the invention", selected from the group consisting of:
  i) a nucleic acid coding for the antibody of the invention, and
  ii) a complementary nucleic acid of a nucleic acid as defined in i).

The term "nucleic acid", as used herein, refers to polymers formed by the repetition of monomers called nucleotides linked by phosphodiester bonds. The term includes both DNA and RNA.

The particulars of the antibody of the invention have been previously mentioned and are incorporated herein by reference.

In a particular embodiment, the nucleic acid of the invention encodes an antibody comprising: a) within the heavy chain a CDR-H1 comprising the amino acid sequence shown in SEQ ID NO: 1, a CDR-H2 comprising the amino acid sequence shown in SEQ ID NO: 2, and a CDR-H3 comprising the amino acid sequence shown in SEQ ID NO: 3, and b) within the light chain a CDR-L1 comprising the amino acid sequence shown in SEQ ID NO: 4, a CDR-L2 comprising the amino acid sequence shown in SEQ ID NO: 5, and a CDR-L3 comprising the amino acid sequence shown in SEQ ID NO: 6.

In another particular embodiment, the nucleic acid of the invention encodes an antibody comprising: a) within the heavy chain a CDR-H1 consisting of the amino acid sequence shown in SEQ ID NO: 1, a CDR-H2 consisting of the amino acid sequence shown in SEQ ID NO: 2, and a CDR-H3 consisting of the amino acid sequence shown in SEQ ID NO: 3, and b) within the light chain a CDR-L1 consisting of the amino acid sequence shown in SEQ ID NO: 4, a CDR-L2 consisting of the amino acid sequence shown in SEQ ID NO: 5, and a CDR-L3 consisting of the amino acid sequence shown in SEQ ID NO: 6, which corresponds to the antibody identified as 91R mAb in the examples.

In another particular embodiment, the nucleic acid of the invention encodes an antibody comprising: a) within the heavy chain a CDR-H1 comprising the amino acid sequence shown in SEQ ID NO: 7, a CDR-H2 comprising the amino acid sequence shown in SEQ ID NO: 2, and a CDR-H3 comprising the amino acid sequence shown in SEQ ID NO: 3, and b) within the light chain a CDR-L1 comprising the amino acid sequence shown in SEQ ID NO: 8, a CDR-L2 comprising the amino acid sequence shown in SEQ ID NO: 9, and a CDR-L3 comprising the amino acid sequence shown in SEQ ID NO: 10.

In another particular embodiment, the nucleic acid of the invention encodes the antibody comprising: a) within the heavy chain a CDR-H1 consisting of the amino acid sequence shown in SEQ ID NO: 7, a CDR-H2 consisting of the amino acid sequence shown in SEQ ID NO: 2, and a CDR-H3 consisting of the amino acid sequence shown in SEQ ID NO: 3, and comprises b) within the light chain a CDR-L1 consisting of the amino acid sequence shown in SEQ ID NO: 8, a CDR-L2 consisting of the amino acid sequence shown in SEQ ID NO: 9, and a CDR-L3 consisting of the amino acid sequence shown in SEQ ID NO: 10, which corresponds to the antibody identified as 92R mAb in the examples.

Said nucleic acid of the invention can contain a regulatory sequence operatively linked for the expression of the nucleotide sequence encoding the antibody of the invention, thereby forming a gene construct, hereinafter the "gene construct of the invention". As used herein, the term "operatively linked" means that the antibody encoded by the nucleic acid sequence of the invention is expressed in the correct reading frame under control of the expression control or regulating sequences. Therefore, in another aspect, the invention provides an expression cassette, hereinafter the "expression cassette of the invention", comprising the gene construct of the invention operatively linked to an expression control sequence. The gene construct of the invention can be obtained through the use of techniques widely known in the prior art (Sambrook et al., 2001 "Molecular cloning: to Laboratory Manual", $3^a$ ed., Cold Spring Harbor Laboratory Press, N.Y., Vol. 1-3).

Control sequences are sequences that control and regulate transcription and, where appropriate, the translation of said antibody, and include promoter sequences, transcriptional regulators encoding sequences, ribosome binding sequences (RBS) and/or transcription terminating sequences. The expression cassette of the present invention may additionally include an enhancer, which may be adjacent to or distant from the promoter sequence and can function to increase transcription from the same. In a particular embodiment, said expression control sequence is functional in prokaryotic cells and organisms, such as bacteria, etc. Whereas in another particular embodiment, said expression control sequence is functional in eukaryotic cells and organisms, for example, insect cells, plant cells, mammalian cells, etc.

Any available promoter can be used in this methodology. In a preferred embodiment of the present invention, the promoter used in the nucleic acid construct of the present invention is active in the specific cell population to be transfected. Illustrative, non-limiting examples of ubiquitous promoters which can be present in the expression cassette of the invention include the human cytomegalovirus promoter (hCMV), SV40 promoter, the EF1-alpha promoter to, and the ubiquitin promoter C. Illustrative, non-limiting examples of cell-type specific promoters and/or tissue specific promoters such as albumin include which is specific for liver [Pinkert et al. (1987) Genes Dev 1:268-277], lymphoid-specific promoters [Calame et al.; (1988) Adv. Immunol. 43:235-275], in particular promoters of T cell receptors [Winoto et al. (1989) EMBO J. 8:729-733] and immunoglobulins [Banerji et al. (1983) Cell 33729-740], neuron-specific promoters such as neurofilament promoter [Byrne et al. (1989) Proc. Natl. Acad. Sci USA 86:5473-5477], pancreas-specific promoters [Edlunch et al. (1985) Science 230:912-916] or mammary gland-specific promoters such as the milk whey promoter (U.S. Pat. No. 4,873,316 and EP No. 264,166). The expression cassette CAG-GS is composed of a CMV enhancer element, the promoter of the chicken β-actin and the post-transcriptional regulatory element (WPRE) virus woodchuck hepatitis (Woodchuck Hepatitis Virus, WHP) [Niwa et al. (1991) Gene 108: 193-9]. The combination of promoter and this element favors high expression levels of the transgene in vivo.

Advantageously, the expression cassette of the invention further comprises a marker or gene encoding a motif or phenotype which allows selecting the transformed host cell with said expression cassette. Illustrative examples of said markers that could be present in the expression cassette of the invention include antibiotic resistance genes, genes for resistance to toxic compounds, and in general, all those that allow selecting the genetically transformed cells.

The gene constructs of the invention or the expression cassette of the invention can be inserted into appropriate vectors. Thus, in another aspect, the invention relates to a vector, such as an expression vector, hereinafter the "vector of the invention", comprising said gene constructs or said expression cassettes of the invention. The choice of vector depends on the host cell in which it will be subsequently introduced. As an example, the vector into which is inserted the said nucleic acid sequences may be a plasmid or a vector which, when introduced into a host cell, is integrated or not in the genome of said cell. Obtaining this vector can be performed by conventional methods known to those skilled in the art (Sambrook et al. 2001, cited supra). In a particular embodiment, said recombinant vector is a vector useful to transfect animal cells.

Said vector can be used to transform, transfect or infect cells susceptible of being transformed, transfected or infected by said vector. Such cells can be prokaryotic or eukaryotic. Therefore, in another aspect, the invention relates to a cell, hereinafter the "cell of the invention", transformed, transfected or infected with a vector of the invention. Said transformed cell, transfected or infected comprises, therefore, a nucleic acid of the invention, a gene construct of the invention or an expression cassette or vector of the invention.

Transformed cells, transfected or infected may be obtained by conventional methods known to those skilled in the art (Sambrook et al. 2001, cited supra). Cells suitable for performing the invention include, without limitation, mammalian, plant, insect, fungal and bacterial cells. Bacterial cells include, without limitation, cells from Gram positive bacteria such as species of the genus *Bacillus, Streptomyces* and *Staphylococcus* and Gram-negative bacterial cells such as cells of the genus *Escherichia* and *Pseudomonas*. Fungal cells preferably include yeast cells such as *Saccharomyces, Pichia pastoris* and *Hansenula* polymorphs. Insect cells include, without limitation, *Drosophila* cells and Sf9 cells. Plant cells include, among others, cells of crop plants such as cereals, medicinal, ornamental or bulbs. Mammalian cells suitable for the present invention include epithelial cell lines, osteosarcoma cell lines, neuroblastoma cell lines, epithelial carcinomas, glial cells, hepatic cell lines, CHO (Chinese Hamster Ovary) cells, COS cells, BHK cells, HeLa cells, 911 cells, AT1080 cells, A549 cells, 293 and 293T cells, PER.C6 cells, NTERA-2 human ECCs cells, D3 cells of the mESCs line, human embryonic stem cells such as HS293, hMSCs and BGV01, SHEF1, SHEF2 and HS181, NIH3T3 cells, REH and MCF-7 cells.

In a particular embodiment, said cell is an animal cell transformed, transfected or infected with a suitable vector, said transfected, transduced or infected animal cell being capable of expressing the antibody of the invention, therefore said vectors can be used for expressing the antibodies of the invention in animal cells. The term "antibody" and its particulars have been described in detail in the context of the antibody of the invention and are used with the same meaning in the context of the nucleic acids, expression cassettes, vectors and cells of the invention.

The nucleic acid, gene construct, expression cassette, vector or cell of the invention can be used to produce an antibody of the invention. In a particular embodiment, the antibody of the invention expressed or produced by the nucleic acid, gene construct, expression cassette, vector or cell of the invention is the antibody identified as 91R mAb in the examples. In another particular embodiment, the antibody of the invention is the antibody identified as 92R mAb in the examples.

As such, the term "cell of the invention", by extension, also includes hybridoma cells producing the antibody of the invention. The term "hybridoma", as used herein, refers to the hybrid cell line formed by by fusing a specific antibody-producing B cell with a myeloma (B cell cancer) cell that is selected for its ability to grow in tissue culture and for an absence of antibody chain synthesis. The antibodies produced by the hybridoma are usually of a single specificity and are therefore monoclonal antibodies (in contrast to polyclonal antibodies). The production of monoclonal antibodies was invented by Cesar Milstein and Georges J. F. Köhler in 1975 (Köhler and Milstein, 1975, Nature 256: 495-7).

Therefore, in another aspect, the invention relates to a method for producing said antibody of the invention, which comprises growing a cell of the invention under conditions permitting the production of said antibody. The conditions for optimising the culture of said cell will depend on the cell used. If desired, the method for producing the antibody of the invention further includes the isolation and purification of said antibody.

Methods of Diagnosis/Prognosis of the Invention

The antibody of the invention can be used for the in vitro diagnosis and/or prognosis of a disease or condition wherein cells expressing CCR9 participate. Thus, in another aspect, the invention relates to the use of an antibody of the invention for the in vitro diagnosis and/or prognosis of a disease or condition wherein cells expressing CCR9 participate.

Further, in another aspect, the invention relates to an in vitro method for diagnosis and/or prognosis of a disease or condition wherein cells expressing CCR9 participate in a subject, hereinafter "first method of the invention", comprising:

a) contacting the antibody of the invention with a sample comprising cells from said subject;
b) detecting and/or quantifying CCR9 in said sample from said subject;
c) comparing the presence and/or amount and/or distribution of said CCR9 detected in said sample from said subject with that of CCR9 detected in a control sample; and
d) correlating the result obtained with the presence of a disease or condition wherein cells expressing CCR9 participate.

The first method of the present invention is a highly sensitive and specific method, and it is based, for example, on the fact that subjects or individuals with a disease or condition wherein cells expressing CCR9 participate, or increased number of CCR9 positive cells on a given population or subpopulation of cells, in absolute terms or in comparison with the corresponding levels in control samples, from subjects who do not have a clinical history of these disease or condition wherein cells expressing CCR9 participate or from cultures of cells that do not express CCR9 (negative controls).

The terms "antibody" and "CCR9" have been described in detail in the context of the antibody of the invention, and their particulars have been described in detail in the context of the antibody of the invention and are used with the same meaning in the context of the first method of the invention.

The term "subject" or "individual" refers to members of mammalian species, and includes but is not limited to domestic animals, primates and humans; the subject is preferably a male or female human being of any age or race.

To put the first method of the invention into practice, a sample comprising cells, such as a biological sample, is obtained from the subject to be studied. The term "sample" or "biological sample", as used herein, includes different types of biological fluids, sections of tissues of the affected organs, etc. In a particular embodiment, the sample comprises cells from the subject under study. Illustrative, non-limiting examples of said samples include different types of biological fluids, such as peritoneal fluid, pleural fluid, synovial fluid, urine, saliva, blood, semen, serum, etc. These biological fluid samples can be obtained by any conventional method known by persons having ordinary skill in the art. Alternatively, said sample can also be a section of an affected organ tissue sample, for example from the lymphoid gland, breast, prostate, skin, small bowel, large, bowel, pancreas, ovary, lung, bladder, kidney, etc., which can be obtained by any conventional method, for example by means of biopsy, cystoscopy, surgical resection, etc., as well as frozen sections taken for histologic purposes.

The samples to be analysed can be obtained from subjects who have been previously diagnosed, or not diagnosed, with a disease or condition wherein cells expressing CCR9 participate, or also from a subject undergoing treatment, or who has been previously treated, for a disease or condition wherein cells expressing CCR9 participate.

According to step (a) of the first method of the invention, the antibody of the invention is contacted with a sample from the subject under study under suitable conditions known by the skilled person in the art.

The person skilled in the art can use a number of conventional methods to detect and/or quantify CCR9 in the sample, which are suitable for carrying out step (b) of the first method of the invention. Particularly useful are immunological methods. Thus, in a particular embodiment, the first method of the invention comprises contacting the antibody of the invention with a sample comprising tumour cells from said individual in order to detecti and/or quantify CCR9 in said sample.

The antibody of the invention to be used in these assays can be labelled or not labelled. The term "detectable label" or "labelling agent", as used herein, refers to a molecular label which allows the detection, localization and/or identification of the molecule to which it is attached, using suitable procedures and equipment for detection, for example by spectroscopic, photochemical, biochemical, immunochemical or chemical means. Labelling agents that are suitable for labelling the antibodies include radionuclides, enzymes, fluorophores, chemiluminescent reagents, enzyme substrates or cofactors, enzyme inhibitors, particles, dyes and derivatives, and the like. As the person skilled in the art will understand, antibodies that are not labelled need to be detected with an additional reagent, for example, a secondary antibody that is labelled, which will be labelled. This is particularly useful in order to increase the sensibility of the detection method, since it allows the signal to be amplified.

There is a wide range of conventional assays that can be used in the present invention which use an antibody of the invention that is not labelled (primary antibody) and an antibody of the invention that is labelled (secondary antibody); these techniques include Western blot or immunoblot, ELISA (Enzyme-Linked Immunosorbent Assay), RIA (Radioimmunoassay), competitive EIA (Competitive Enzyme Immunoassay), DAS-ELISA (Double Antibody Sandwich-ELISA), immunocytochemical and immunohistochemical techniques, flow cytometry or multiplex detection techniques based on using protein microspheres, biochips or microarrays which include the antibody of the invention. Other ways of detecting and quantifying CCR9 using the antibody of the invention include affinity chromatography techniques, ligand binding assays or lectin binding assays.

The first method of the invention also comprises, under step (c), the step of comparing the presence, and/or amount and/or distribution of said CCR9 detected or determined in the sample from the subject object of study, with that of CCR9 in the control sample (reference value).

The term "control sample" or "reference sample", as used herein, refers to a sample that does not comprise CCR9-expressing cells or comprises CCR9-expressing cells under normal physiological conditions, and, therefore it can be used for establishing a reference value. In a particular embodiment, the reference sample is taken from a healthy subject, although it may also be taken from other subjects, including subjects who do not have a clinical history of a disease or condition wherein cells expressing CCR9 participate, the same subject but from a tissue or part thereof which is under a normal physiological condition or healthy. In a particular embodiment, the control sample is a sample from a healthy subject. In another particular embodiment, the control sample is a sample from an individual who does not have a clinical history of a disease or condition wherein cells expressing CCR9 participate, in which case the results obtained could have a diagnostic or predictive value of the malignancy, invasiveness, stage and/or severity of said a disease or condition wherein cells expressing CCR9 participate in the subject. In another particular embodiment, the control sample is a sample from the same subject but from a tissue or part thereof which is healthy. A positive control, for example a cell line that expresses CCR9, and/or a negative control, for example a cell line that does not express CCR9, can additionally be used if desired.

The term "distribution", as used herein, refers to the population or type of cells where CCR9 is expressed in a sample. Thus, CCR9 may be expressed in one or more than one particular cell population or type. By cell population or cell type it is understood morphologically and phenotypically distinct cells, such as T cells, B cells, macrophages, epithelial cells, muscle cells, osteoclasts, osteoblasts, neurons, etc. Thus, by comparing the distribution of CCR9 between the sample to be analysed and the reference sample, one is comparing the presence of CCR9 in the different cell populations present in the said samples.

The first method of the invention additionally comprises, as step (d), the step of correlating the result obtained from the comparison of step (c) with the presence of a disease or condition wherein cells expressing CCR9 participate, the determination or prognosis of the malignancy, invasiveness, stage and/or severity of said disease or condition wherein cells expressing CCR9 participate in said subject.

In a particular embodiment, the presence of CCR9 in the sample being analysed when CCR9 is not present in the reference sample is indicative of the subject having a disease or condition wherein cells expressing CCR9 participate.

In another particular embodiment, an altered distribution of CCR9 in the sample being analysed in respect with that of CCR9 in the reference sample is indicative of the subject having a disease or condition wherein cells expressing CCR9 participate. It is considered that the distribution of CCR9 is "altered" when CCR9 is expressed in a different cell population with respect to the reference sample, or when CCR9 is expressed in at least one different additional cell population with respect to the reference sample.

In another particular embodiment, an increase in the amount said CCR9 in the sample from said subject with respect to the amount of CCR9 in said reference sample is indicative of a disease or condition wherein cells expressing CCR9 participate. It is considered that the amount of CCR9 in the sample being analysed is "increased" in respect to the amount of CCR9 in the reference sample when it increases in at least 1%, at least 2%, at least 3%, at least 4%, at least 5%, at least 10%, at least 15%, at least 20%, at least 25%, at least 30%, at least 40%, at least 50%, at least 60%, at least 70%, at least 80%, at least 90%, at least 100%, at least 110%, at least 120%, at least 150%, at least 200% or more in respect to the reference sample.

Said information can also be used for determining or evaluating or predicting the malignancy, invasiveness, stage and/or severity of said disease or condition wherein cells expressing CCR9 participate in said subject; in this sense, the person skilled in the art, in view of the experience that he/she has acquired, will be able to correlate the amount of CCR9 determined in the sample from the subject under study with the malignancy, invasiveness, stage and/or severity of said disease or condition wherein cells expressing CCR9 participate in said subject. Likewise, when the control sample is a sample from the subject himself/herself diagnosed with a disease or condition wherein cells expressing CCR9 participate, analysed before or during the administration of a therapy for treating said disease or condition wherein cells expressing CCR9 participate, the information relating to the detection or to the variation in the distribution and/or amount of said CCR9 in the sample from said subject at a given time after the administration of said therapy, can serve for monitoring or evaluating the effect or efficacy of the therapy administered to said subject who suffers from said disease or condition wherein cells expressing CCR9 participate, as it will be described below, and, if said therapy is not effective, evaluating the possibility of changing it.

As it will be understood by those skilled in the art, the prediction, although preferred to be, need not be correct for 100% of the subjects to be diagnosed or evaluated. The term, however, requires that a statistically significant portion of subjects can be identified as having an increased probability of having a given outcome. Whether the data obtained from a subject is statistically significant can be determined without further ado by the person skilled in the art using various well known statistic evaluation tools, e.g., determination of confidence intervals, p-value determination, cross-validated classification rates and the like etc. Details are found in Dowdy and Wearden, Statistics for Research, John Wiley & Sons, New York 1983. Preferred confidence intervals are at least 50%, at least 60%, at least 70%, at least 80%, at least 90% or at least 95%. The p-values are, preferably, 0.01, 0.005 or lower.

The term "disease or condition wherein cells expressing CCR9 participate", as used herein, refers to a disease or condition in which cells expressing CCR9 are directly or indirectly involved independently that CCR9 is, or not, the responsible of the disease or condition, including, for example, diseases or conditions in which CCR9 is expressed in an altered way, location or distribution, or in altered amount, for example a higher value, with respect to normal or reference physiological conditions or reference values. As such, the term "disease or condition wherein cells expressing CCR9 participate" is substantially equivalent to "disease or condition concomitant with cells expressing CCR9", or "disease or condition wherein cells expressing CCR9 are, directly or indirectly, implied" or similar.

In a particular embodiment, said disease or condition wherein cells expressing CCR9 participate is selected from the group consisting of a tumour disease and a non-tumour disease.

In a preferred embodiment, said disease or condition wherein cells expressing CCR9 participate is a tumour disease. In a more preferred embodiment, said tumour disease is selected from the group consisting of T-cell acute lymphoblastic leukaemia, prostate cancer, breast cancer, melanoma, ovarian cancer, colorectal cancer, lung cancer, and circulating cells from a solid tumour.

The term "T-cell acute lymphoblastic leukaemia" or "T-ALL", as used herein, refers to a type of malignant proliferative disorder of T-cell lymphoblasts in the blood and bone marrow and is a form of lymphoid leukaemia.

The term "prostate cancer", as used herein, refers to any malignant proliferative disorder of prostate cells.

The term "breast cancer", as used herein, refers to any malignant proliferative disorder of breast cells, most commonly from the inner lining of milk ducts or the lobules that supply the ducts with milk. Cancers originating from ducts are known as ductal carcinomas, while those originating from lobules are known as lobular carcinomas.

The term "melanoma", as used herein, refers to a malignant skin tumour of melanocytes.

The term "ovarian cancer", as used herein, refers to is a cancerous growth arising from the ovary.

The term "colorectal cancer", also known as "colon cancer", "rectal cancer", or "bowel cancer", as used herein refers to a cancer from uncontrolled cell growth in the colon or rectum, or in the appendix.

The term "lung cancer", as used herein, refers to a type of malignant proliferative disorder in tissues of the lung.

The term "circulating cells from a solid tumour" or CTCs (Circulating Tumour Cells), as used herein, refers to cells that have shed into the vasculature from a primary tumour and circulate in the bloodstream. CTCs can be responsible for subsequent growth of additional tumours (metastasis) in distant organs.

In another preferred embodiment, said disease or condition wherein cells expressing CCR9 participate is a non-tumour disease. In a particular embodiment, said non-tumour disease is an autoimmune disease. In another particular embodiment, said non-tumour disease or condition comprises an inflammatory disorder or is a disease wherein an inflammatory response or component is present. In a specific embodiment, said non-tumour disease is selected from the group consisting of Crohn's disease, inflammatory bowel disease, liver fibrosis, and acute liver inflammation.

The term "Crohn's disease", as used herein, refers to a type of inflammatory bowel disease that may affect any part of the gastrointestinal tract from mouth to anus, causing a wide variety of symptoms. It primarily causes abdominal pain, diarrhea (which may be bloody if inflammation is at its worst), vomiting (can be continuous), or weight loss, but may also cause complications outside the gastrointestinal tract such as anemia, skin rashes, arthritis, inflammation of the eye, tiredness, and lack of concentration. Crohn's disease is caused by interactions between environmental, immunological and bacterial factors in genetically susceptible individuals. This results in a chronic inflammatory disorder, in which the body's immune system attacks the gastrointestinal tract. While Crohn's is an immune related disease, it does not appear to be an autoimmune disease (in that the immune system is not being triggered by the body itself).

The term "inflammatory bowel disease", as used herein, refers to a group of inflammatory conditions of the colon and small intestine, which include ucerative colitis, collagenous colitis, lymphocytic colitis, ischaemic colitis, diversion colitis, Behçet's disease, and indeterminate colitis.

The term "liver fibrosis" is also known as "hepatic fibrosis" and, as used herein, it refers to a condition where the liver accumulates an excess of extracellular matrix proteins including collagen that occurs in most types of chronic liver diseases; it can be due to a congenital condition or by means of repeated liver damage. Advanced liver fibrosis results in cirrhosis, liver failure, and portal hypertension and often requires liver transplantation.

The term "acute liver inflammation", as used herein, refers to a condition characterized by the destruction of liver cells and the presence of inflammatory cells in the liver tissue.

In a preferred embodiment of the invention, the disease or condition wherein cells expressing CCR9 participate is T-cell acute lymphoblastic leukaemia.

In a preferred embodiment of the invention, the disease or condition concomitant with cells expressing CCR9 is prostate cancer.

In a preferred embodiment of the invention, the disease or condition wherein cells expressing CCR9 participate is breast cancer.

In a preferred embodiment of the invention, the disease or condition wherein cells expressing CCR9 participate is melanoma.

In a preferred embodiment of the invention, the disease or condition wherein cells expressing CCR9 participate is ovarian cancer.

In a preferred embodiment of the invention, the disease or condition wherein cells expressing CCR9 participate is colorectal cancer.

In a preferred embodiment of the invention, the disease or condition wherein cells expressing CCR9 participate is lung cancer.

In a preferred embodiment of the invention, the disease or condition wherein cells expressing CCR9 participate are circulating cells from a solid tumour.

In a preferred embodiment of the invention, the disease or condition wherein cells expressing CCR9 participate is Crohn's disease.

In a preferred embodiment of the invention, the disease or condition wherein cells expressing CCR9 participate is inflammatory bowel disease.

In a preferred embodiment of the invention, the disease or condition wherein cells expressing CCR9 participate is liver fibrosis.

In a preferred embodiment of the invention, the disease or condition wherein cells expressing CCR9 participate is acute liver inflammation.

In another particular embodiment, the cells in which the expression of CCR9 is altered comprise a subpopulation of lymphoid, myeloid, dendritic, plasmacytoid cells, which are defined by additional at least one of the markers including CD2, CD3, CD4, CD5, CD8, CD11, CD14, CD19, CD20, CD25, CD51, CD81, CD146, CD228, CD231, TCR and combinations thereof.

A preferred embodiment comprises a rapid test in tissue in a procedure where histological tissue sample is stained with antibodies of the invention fluorescently labelled. In a further preferred process the antibody of the invention, preferably an IgG isotype antibody, is combined with an additional antibody, which specifically recognizes CD2, CD3, CD4, CD5, CD8, CD11, CD14, CD19, CD20, CD25, CD51, CD81, CD146, CD228, CD231, TCR. In a further preferred embodiment the antibodies are directly labelled with different fluorescent dyes, such as Cy3 and Cy5 or Cy3 and FITC.

In an embodiment, in which a signal enhancement is advantageous, antibodies and/or recognition molecules are increased by labelled secondary antibodies or biotin-streptavidin detection systems. It is therefore advantageous to use isotypes and/or sequences of different species in the constant region of the antibody. The technologies and methods used in this document, for example immunohistology, and the choice of the appropriate format of the recognition molecules are known to the skilled artisan.

Additionally, the antibody of the invention, in view of its ability to specifically bind target cells (i.e., cells expressing CCR9, or $CCR9^+$ cells), can also be used for in vivo diagnosis and/or prognosis of a disease or condition wherein cells expressing CCR9 participate; by illustrative, said antibodies can be used in medical imaging, i.e., a set of techniques and processes used to create images of a body (or parts and function thereof), e.g., a human body, for clinical purposes, such as medical procedures seeking to reveal, diagnose or examine a disease, or for medical science, including the study of normal anatomy and physiology.

Therefore, in another aspect, the invention relates to the use of the antibody of the invention for in vivo diagnosis and/or prognosis of a disease or condition wherein cells expressing CCR9 participate, or to the use of the antibody of the invention in a method for in vivo diagnosis and/or prognosis of a disease or condition wherein cells expressing CCR9 participate; alternatively, this aspect can be expressed as the use of the antibody of the invention in the manufacture of a composition for in vivo diagnosis and/or prognosis of a disease or condition wherein cells expressing CCR9 participate. In another alternative wording, this aspect can be expressed as the antibody of the invention for use in an in vivo diagnosis and/or prognosis of a disease or condition wherein cells expressing CCR9 participate, or as the antibody of the invention for use in a method for in vivo diagnosis and/or prognosis of a disease or condition wherein cells expressing CCR9 participate.

To this end, antibodies of the invention are labelled by suitable methods known in the art, and are provided as agents for diagnostic imaging methods, such as radioimmunodiagnostics, positron emission tomography (PET), endoscopy immunofluorescent methods, etc., for example by means of coupling and/or loading with appropriate molecules, for example radioactive isotopes or fluorescent dyes. In a preferred embodiment, the antibody of the invention is coupled to gamma-emitting istotopes, for example, $^{99m}$Tc, $^{123}$I, and $^{111}$In, and used in radioimmunoscintigraphy using gamma cameras or single-photon emission computed tomography. In another preferred embodiment, the antibody of the invention is coupled to positron emitters, for example, $^{18}$F, $^{64}$Cu, $^{68}$Ga, $^{86}$Y, and $^{124}$I, and used in PET. In another preferred embodiment, the antibody of the invention is coupled to fluorescent dyes, such as Cy3, Cy2, Cy5 or FITC, and used in endoscopy immunofluorescent methods. The antibodies modified as described are administered by any suitable route, for example, intravenously, at an appropriate dose for the individual and the location of CCR9 is detected, determined or measured by processes well known in the art. The methods and technologies used herein, including diagnostic imaging, are known to the skilled artisan, who can also provide suitable dose formulations.

In a further preferred embodiment, the antibody of the invention is radioactively labelled, for instance with $^{111}$In, and is provided as diagnostic agent which can be given locally in the tumour or in the blood vessels of the tumour afferent or efferent or systemically. This serves in one embodiment for the determination of tumour size and a further embodiment for the determination of the lymph nodes. The methods and technologies used herein, including diagnostic imaging, are known to the skilled artisan, who can also provide suitable dosage formulations.

The radiolabelled recognition molecules of the invention used in diagnostic assays or as diagnostic agents may also be administered by other routes of application. For this, preferred routes are intraperitoneal, intranodal, intratumoural and intravenous routes.

Further, the antibody of the invention will be formulated in a composition suitable for its administration to a subject. To that end, the composition will include the necessary pharmaceutically acceptable excipients or carriers. Illustrative, non-limiting, examples of said compositions will be described below and are incorporated herein by reference.

Method for Monitoring the Response to Treatment of a Disease or Condition Wherein Cells Expressing CCR9 Participate In another aspect, the invention relates to an in vitro method for monitoring the response to treatment of a disease or condition wherein cells expressing CCR9 participate in a subject under treatment, hereinafter referred to as "the second method of the invention", comprising:

a) contacting the antibody of the invention with a first sample comprising cells from said subject taken at a first time-point;
b) detecting and/or quantifying CCR9 in said first sample;
c) contacting the antibody of the invention with a second sample comprising cells from said subject taken at a second time-point;
d) detecting and/or quantifying CCR9 in said second sample;
e) comparing the presence and/or amount and/or distribution of CCR9 detected in said first sample and second sample; and
f) correlating the result obtained with the response to treatment of a disease or condition wherein cells expressing CCR9 participate.

The terms "antibody", "CCR9", "sample", "subject", "disease or condition wherein cells expressing CCR9 participate", "distribution" and their particulars have been described in detail in the context of the antibody and the first method of the invention and are used with the same meaning in the context of the second method of the invention.

The term "treatment", as used herein, refers to the therapy suitable for the remediation of the disease or condition wherein cells expressing CCR9 participate. Suitable treatments for a disease or condition wherein cells expressing CCR9 participate are conventional and well-known by the person skilled in the art.

The second method of the invention comprises a first step of contacting the antibody of the invention with a first sample comprising cells from said subject taken at a first time-point. As the person skilled in the art will appreciate, step (a) of the second method of the invention is identical to step (a) of the first method of the invention, which has been described in detail above. Thus the particulars of step (a) of the first method of the invention are incorporated herein by reference.

Step (b) of the second method of the invention comprises detecting and/or quantifying CCR9 in said first sample. Step (b) of the second method of the invention is identical to step (b) of the first method of the invention, which has been described in detail above. Thus the particulars of step (b) of the first method of the invention are incorporated herein by reference.

The second method of the invention further comprises steps (c) and (d) comprising contacting the antibody of the invention with a second sample and detecting and/or quantifying CCR9 in said second sample, wherein said second sample is taken at a second time-point.

The term "time point", as used herein, refers to a moment in time at which a sample is taken from the subject being monitored. In the context of the second method of the invention, there is a first or initial time point, at which the first sample is taken, and a second or later time point, at which the second sample is taken. The first and second time points are separated in time by at least 1 day, at least 2 days, at least 3 days, at least 4 days, at least 5 days, at least 10 days, at least 20 days, at least 30 days, at least 40 days, at least 50 days, at least 60 days, at least 70 days, at least 80 days, at least 90 days, at least 100 days, at least 6 months, at least 1 year, at least 2 years, at least 5 years, at least 10 years, or more. In a particular embodiment, the first time point happens before the second time point, so that the first sample is taken before the second sample.

As the person skilled in the art will realise, in a particular embodiment, it is particularly useful that the first sample is taken before the subject begins treatment for a disease or condition wherein cells expressing CCR9 participate in order to fully monitor the response to said treatment. Thus, in a particular embodiment, the first time point occurs before treatment for a disease or condition wherein cells expressing CCR9 participate has begun. In another particular embodiment, the first time point occurs when treatment for a disease or condition wherein cells expressing CCR9 participate has begun. Likewise, in a particular embodiment, the first sample is taken before treatment for a disease or condition wherein cells expressing CCR9 participate has begun, whereas in another particular embodiment, the first sample is taken when treatment for a disease or condition wherein cells expressing CCR9 participate has begun.

In order to monitor the response of said subject to said treatment, it will be necessary that the second sample is taken once the subject has begun said treatment. Thus, in another particular embodiment, the second time point occurs after treatment for a disease or condition wherein cells expressing CCR9 participate has begun. In a particular embodiment, the second time point occurs at least 1 day, at least 2 days, at least 3 days, at least 4 days, at least 5 days, at least 10 days, at least 20 days, at least 30 days, at least 40 days, at least 50 days, at least 60 days, at least 70 days, at least 80 days, at least 90 days, at least 100 days, at least 6 months, at least 1 year, at least 2 years, at least 5 years, at least 10 years, or more after treatment for a disease or condition wherein cells expressing CCR9 participate has begun. Likewise, the second sample is taken after treatment for a disease or condition wherein cells expressing CCR9 participate has begun. In a particular embodiment, the second sample is taken at least 1 day, at least 2 days, at least 3 days, at least 4 days, at least 5 days, at least 10 days, at least 20 days, at least 30 days, at least 40 days, at least 50 days, at least 60 days, at least 70 days, at least 80 days, at least 90 days, at least 100 days, at least 6 months, at least 1 year, at least 2 years, at least 5 years, at least 10 years, or more after treatment for a disease or condition wherein cells expressing CCR9 participate has begun.

The second method of the invention also comprises the step of comparing the presence and/or amount and/or distribution of CCR9 detected in said first and second samples [step (e)] prior to the correlation step [step (f)] wherein the result obtained from the comparison of step (e) is correlated with the response to treatment of a disease or condition wherein cells expressing CCR9 participate.

In a particular embodiment, the lack of presence of CCR9 in the second sample in respect to the first sample is indicative of a favourable response to said treatment. Alternatively, the presence of CCR9 in the second sample in respect to the first sample is, or maybe, indicative of an unfavourable response to said treatment.

In another particular embodiment, an altered distribution of CCR9 in the second sample in respect to that of the first sample, where CCR9 is expressed in fewer or less cell populations in the second sample with respect to the first sample, is indicative of a favourable response to said treatment. On the other hand, an unaltered distribution of CCR9 in the second sample in respect with that of the first sample, or an altered distribution of CCR9 in the second sample in respect to that of the first sample, where CCR9 is expressed in more cell populations in the second sample with respect to the first sample, is indicative of an unfavourable response to said treatment.

In another particular embodiment, a decrease in the amount of CCR9 in the second sample with respect to the amount of CCR9 in the first sample is indicative of a favourable response to said treatment. It is considered that the amount of CCR9 in the second sample is decreased in respect to the amount of CCR9 in the first sample when it decreases in at least 1%, at least 2%, at least 3%, at least 4%, at least 5%, at least 10%, at least 15%, at least 20%, at least 25%, at least 30%, at least 40%, at least 50%, at least 60%, at least 70%, at least 80%, at least 90%, at least 100%, at least 110%, at least 120%, at least 150%, at least 200% or more in respect to the first sample. Likewise, an increase in the amount of CCR9 in the second sample with respect to the amount of CCR9 in the first sample is indicative of an unfavourable response to said treatment. It is considered that the amount of CCR9 in the sample being analysed is increased in respect to the amount of CCR9 in the reference sample when it increases in at least 1%, at least 2%, at least 3%, at least 4%, at least 5%, at least 10%, at least 15%, at least 20%, at least 25%, at least 30%, at least 40%, at least 50%, at least 60%, at least 70%, at least 80%, at least 90%, at least 100%, at least 110%, at least 120%, at least 150%, at least 200% or more in respect to the reference sample.

The term "response to treatment", as used herein, refers to the evolution of a disease or condition wherein cells expressing CCR9 participate that is being treated, and it may be a favourable response or an unfavourable response. Generally, a favourable response to treatment involves a partial or complete amelioration or disappearance of the symptoms and/or lesions caused by said disease or condition, whereas an unfavourable response to treatment involves an aggravation or deterioration of the symptoms and/or lesions caused by said disease or condition. There are various ways of evaluating the response to treatment of a disease or condition wherein cells expressing CCR9 participate, which are conventional and well-known by the person skilled in the art. By way of illustrative, non-limiting example, when the disease or condition wherein cells expressing CCR9 participate is a type of cancer, in particular a solid tumour, the response to treatment may be evaluated as:

Complete Response (CR): Disappearance of all target lesions;

Partial Response (PR): At least a 30% decrease in the sum of the longest diameter (LD) of target lesions, taking as reference the baseline sum of the LD;

Stable Disease (SD): Neither sufficient shrinkage to qualify for PR nor sufficient increase to qualify for PD, taking as reference the smallest sum LD since the treatment started; or Progressive Disease (PD): At least a 20% increase in the sum of the LD of target lesions, taking as reference the smallest sum LD recorded since the treatment started or the appearance of one or more new lesions;

wherein CR and PR are favourable responses to treatment, and PD is an unfavourable response to treatment.

Uses of the Invention

The antibody of the invention, which specifically binds to an epitope of CCR9, can be used therapeutically, as well as in immunochemical assays, such as immunofluorescence assays, flow cytometry, Western blots, immunohistochemical assays, immunoprecipitations, or other immunochemical assays known in the art.

Thus, another aspect of the present invention is an antibody of the invention for use as a medicament, hereinafter "first use of the invention".

The present invention also relates to the use of the antibody of the invention in the manufacture of a medicament. Alternatively, this aspect may be reformulated as a method of treatment which comprises administering the antibody of the invention.

The authors of the present invention have shown that this antibody is particularly useful for the treatment of a disease or condition wherein cells expressing CCR9 participate, as the antibody is able to inhibit in vivo growth of a CCR9-expressing xenograft model of human acute lymphoblastic leukaemia, is able to promote necrosis and apoptosis as well as reduced angiogenesis and cell proliferation, and mediates complement-dependent cytotoxicity (CDC).

Thus, another aspect of the present invention is an antibody of the invention for use in the treatment of a disease or condition wherein cells expressing CCR9 participate, hereinafter "second use of the invention".

The present invention also relates to the use of the antibody according to the invention in the manufacture of a medicament for treatment of a disease or condition wherein cells expressing CCR9 participate. Alternatively, this aspect may be reformulated as a method of treatment of a disease or condition wherein cells expressing CCR9 participate, which comprises administering the antibody of the invention.

The terms "antibody", "CCR9", "disease or condition wherein cells expressing CCR9 participate", and their particulars have been described in detail in the context of the antibody of the invention and are used with the same meaning in the context of the first use of the invention.

In a particular embodiment of the first use of the invention, the disease or condition wherein cells expressing CCR9 participate is selected from the group consisting of T-cell acute lymphoblastic leukaemia, prostate cancer, breast cancer, melanoma, ovarian cancer, colorectal cancer, lung cancer, Crohn's disease, inflammatory bowel disease, liver fibrosis, acute liver inflammation, circulating cells from a solid tumour.

The term "treatment" or "therapy" can be used indistinctly and refer to clinical intervention in an attempt to prevent, cure, delay, reduce the severity of, or ameliorate one or more symptoms of the disease or disorder or recurring disease or disorder, or in order to prolong the survival of a patient beyond that expected in the absence of such treatment.

As the person skilled in the art will recognize, the antibody of the invention may be useful in therapeutic applications in various forms, which include without limitation, in the form of intact antibody, conjugated to another therapeutic agent, and in the form of a fusion protein with another therapeutic agent. These therapeutic applications will comprise the administration of a therapeutically effective amount of the antibody of the invention.

The term "therapeutically effective amount", as used herein, refers to the amount of the antibody of the invention which is required to achieve an appreciable prevention, cure, delay, reduction of the severity of, or amelioration of one or more symptoms of the disease or condition wherein cells expressing CCR9 participate.

In a particular embodiment of the first and second uses of the invention, the antibody of the invention is in the form of the intact antibody, i.e., in the form of immunoglobulin. The antibody of the invention, when is in the form of immunoglobulin, typically uses a combination of mechanisms in directing cytotoxic effects to a CCR9-expressing cell: (i) it interacts with components of the immune system through antibody-dependent cellular cytotoxicity (ADCC) or (ii) through complement-dependent cytotoxicity (CDC).

Antibody-dependent cellular cytotoxicity (ADCC) occurs when antibodies bind to antigens on cells and the antibody Fc domains engage Fc receptors (FcR) on the surface of immune effector cells. Several families of Fc receptors have been identified, and specific cell populations characteristically express defined Fc receptors. For example, neutrophils commonly express human FcγRI (CD64), FcγRII (CD32) and the B (lipid anchored) isoform of FcγRIII (CD16). In contrast, human natural killer (NK) cells express only the A (transmembrane) isoform of CD16. This structure facilitates recruitment of adaptor proteins and activation of NK cells by antibody engagement of CD16.

Complement-dependent cytotoxicity (CDC) is another cell-killing method that can be directed by antibodies. As with ADCC, the different subclasses of antibodies have varying abilities to elicit CDC responses. IgM is the most effective isotype for complement activation, and IgG1 and IgG3 are both very effective at directing CDC via the classical complement activation pathway. In this cascade, the formation of antigen-antibody complexes results in the uncloaking of multiple C1q binding sites in close proximity on the $C_H2$ domains of participating IgG molecules (C1q is one of three subcomponents of complement C1). These uncloaked C1q binding sites convert the previously low-affinity C1q-IgG interaction to one of high avidity, which triggers a cascade of events involving a series of other complement proteins and leads to the proteolytic release of the effector-cell chemotactic/activating agents C3a and C5a. The complement cascade ends in the formation of a membrane attack complex, which creates 100 Å pores in the cell membrane that facilitate free passage of water and solutes into and out of the cell.

In another particular embodiment of the first and second uses of the invention, the antibody of the invention is conjugated to or in the form of a fusion protein with another therapeutic agent.

Suitable therapeutic agents for forming immunoconjugates of the present invention include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, maytansine or an analog or derivative thereof, mitoxantrone, mithramycin, actinomycin D, 1-ehydrotestosterone, glucocorticoids, procaine, tetracaine, lidocaine, propranolol, and puromycin; calicheamicin or analogs or derivatives thereof; antimetabolites (such as methotrexate, 6-mercaptopurine, 6-thioguanine, cytarabine, fludarabin, 5-fluorouracil, decarbazine, hydroxyurea, asparaginase, gemcitabine, cladribine), alkylating agents (such as mechlorethamine, thioepa, chlorambucil, melphalan, carmustine (BSNU), lomustine (CCNU), cyclophosphamide, busulfan, dibromomannitol, streptozotocin, dacarbazine (DTIC), procarbazine, mitomycin C, cisplatin and other platinum derivatives, such as carboplatin; as well as duocarmycin A, duocarmycin SA, CC-1065 (a.k.a. rachelmycin), or analogs or derivatives of CC-1065), antibiotics (such as dactinomycin (formerly actinomycin), bleomycin, daunorubicin (formerly daunomycin), doxorubicin, idarubicin, mithramycin, mitomycin, mitoxantrone, plicamycin, anthramycin (AMC)), anti-mitotic agents (e.g., tubulin-inhibitors) such as monomethyl auristatin E, monomethyl auristatin F, or other analogs or derivatives of dolastatin 10; diphtheria toxin and related molecules (such as diphtheria A chain and active fragments thereof and hybrid molecules); ricin toxin (such as ricin A or a deglycosylated ricin A chain toxin), cholera toxin, a Shiga-like toxin (SLT-I, SLT-II, SLT-IIV), LT toxin, C3 toxin, Shiga toxin, pertussis toxin, tetanus toxin, soybean Bowman-Birk protease inhibitor, *Pseudomonas* exotoxin, alorin, saporin, modeccin, gelanin, abrin A chain, modeccin A chain, alpha-sarcin, *Aleurites fordii* proteins, dianthin proteins, *Phytolacca americana* proteins (PAPI, PAPII, and PAP-S), *momordica charantia* inhibitor, curcin, crotin, *sapaonaria officinalis* inhibitor, gelonin, mitogellin, restrictocin, phenomycin, and enomycin toxins. Other suitable conjugated molecules include antimicrobial/lytic peptides such as CLIP, Magainin 2, mellitin, Cecropin, and P18; ribonuclease (RNase), DNase I, Staphylococcal enterotoxin-A, pokeweed antiviral protein, diphtherin toxin, and *Pseudomonas* endotoxin. See, for example, Pastan et al., Cell 47, 641 (1986) and Goldenberg, Calif. A Cancer Journal for Clinicians 44, 43 (1994).

In a preferred embodiment of the first and second uses of the invention, the antibody of the invention is conjugated to or in the form of a fusion protein with another therapeutic agent, selected from the group consisting in a cytotoxin, a radionuclide, an immunosuppressant, a chemotherapeutic drug, or a cytokine.

Cytotoxic chemotherapy or radiotherapy of cancer is limited by serious, sometimes life threatening, side effects that arise from toxicities to sensitive normal cells because the therapies are not selective for malignant cells. One strategy to avoid these problems is to couple the therapeutic agent to antibodies or other ligands that recognize tumour-associated antigens. This increases the exposure of the malignant cells, and reduces the exposure of normal cells, to the ligand-targeted therapeutics.

The therapeutic agent can be a radionuclide that acts releasing a cytotoxic radiation to the cell expressing CCR9. When conjugated to an antibody of the invention, the resulting molecule is useful as a radioimmunotherapeutic agent.

In one preferred embodiment of the first and second uses of the invention, the antibody of the invention is conjugated to a radionuclide. Illustrative examples that are useful in the context of the present invention include, without limitation, beta emitters, such as $^{131}$I, $^{90}$Y, $^{99m}$Tc, $^{177}$Lu, and $^{67}$Cu, and alpha emitters, such as $^{213}$Bi and $^{211}$At.

The therapeutic agent can be an immunosuppressive agent, i.e., a substance that acts to suppress or mask the immune system of the mammal being treated herein. This would include substances that suppress cytokine production, down-regulate or suppress self-antigen expression, or mask the MHC antigens.

The therapeutic agent can also be a cytotoxic agent, i.e., a substance that inhibits or prevents the function of cells and/or causes destruction of cells. The term is intended to include radioactive isotopes (as described above), chemotherapeutic agents, i.e., chemical compounds useful in the treatment of cancer, and toxins such as small molecule toxins or enzymatically active toxins of bacterial, fungal, plant or animal origin, or fragments thereof.

The therapeutic agent can also be a cytokine, an hormone, growth factor, necrosis factor, i.e., a protein or peptide released by one cell population which act on another cell as intercellular mediators or even in the same cell population. As used herein, the term cytokine includes proteins and peptides from natural sources or from recombinant cell culture and biologically active equivalents of the native sequence cytokines.

In one preferred embodiment of the first and second uses of the invention, the antibody of the invention is conjugated to one or more toxin molecules. Enzymatically active toxins and fragments thereof which can be used include diphtheria A chain, nonbinding active fragments of diphtheria toxin, exotoxin A chain (from *Pseudomonas aeruginosa*), ricin A chain, abrin A chain, modeccin A chain, alpha sarcin, *Aleurites fordii* proteins, dianthin proteins, *Phytolaca americana* proteins (PAPI, PAPII, and PAP-S), *momordica charantia* inhibitor, curcin, crotin, *sapaonaria officinalis* inhibitor, gelonin, mitogellin, restrictocin, phenomycin, enomycin and the tricothecenes.

The present invention further contemplates the antibody of the invention to be conjugated with a compound with nucleolytic activity (e.g. a ribonuclease or a DNA endonuclease such as a deoxyribonuclease; DNase) or other compound capable of damaging a cellular structure or organelle and therefore killing or diminishing the vitality of the cell.

Conjugates of the antibody and cytotoxic agent may be made using a variety of bifunctional protein coupling agents or linkers. The linker may be a "cleavable linker" facilitating release of the cytotoxic drug in the cell. For example, an acid-labile linker, peptidase-sensitive linker, dimethyl linker or disulfide-containing linker may be used.

Alternatively, a fusion protein comprising the antibody and cytotoxic agent may be made, e.g. by recombinant techniques or peptide synthesis.

The therapeutic agent can also be a prodrug which refers to a precursor or derivative form of a pharmaceutically active substance that is less cytotoxic to tumour cells compared to the parent drug and is capable of being enzymatically activated or converted into the more active parent form.

In one preferred embodiment of the first and second uses of the invention, the antibody of the invention may also be conjugated with a prodrug activating agent which converts a prodrug to an active anti-cancer drug. The agent component of such conjugates includes any agent capable of acting on a prodrug in such a way so as to convert it into its more active, cytotoxic form. This is particularly useful in antibody-directed enzyme prodrug therapy approaches (AD-EPT).

Enzymes useful in the present invention include any enzyme that can convert a prodrug into an active therapeutic agent (drug). In a specific embodiment, the enzyme is an enzyme from a mammal, for example, a human enzyme. In another specific embodiment, the enzyme is an enzyme from an organism other than a mammal; in this last embodiment, the immunogenicity of the enzyme is optionally reduced, for example, by conjugation to polyethylene glycol (PEG) and the like. In accordance with a particular embodiment, neither the enzyme nor an enzyme with similar substrate specificity is endogenous to the subject along the route of administration or biodistribution of the prodrug.

Proteases, glycosidases, esterases and the like are general types of enzymes that can be used in accordance with the present invention. Specific examples of suitable enzymes include, but are not limited to, glycosidases (beta-glucuronidase, beta-glucosidase, beta-galactosidase), beta-lactamase, cellulase, dextranase, fructase, aminopeptidase, lysozyme, cytosine deaminase, carboxypeptidase, penicillin amidase, methionine γ liase, and carboxyesterase. The enzyme is selected for its ability to convert the selected prodrug into its active drug form. For example, if the prodrug comprises a conjugate of dextran and a therapeutic agent, an appropriate enzyme would be dextranase. Similarly, cellulase could be used with a prodrug comprising a cellulose substrate, and glucuronidase could be used with a prodrug comprising a glucuronide.

In a preferred embodiment, the enzyme is selected from the group consisting of glycosidases (glucuronidase, beta-glucosidase, beta-galactosidase), beta-lactamase, cellulase, dextranase, fructase, aminopeptidase, lysozyme, cytosine deaminase, carboxypeptidase, penicillin amidase, methionine γ liase, and carboxyesterase, or a functional variant or fragment thereof having catalytic activity. More preferably, the enzyme is a glycosidase (e.g. beta-galactosidase) or a cytosine deaminase.

Drugs useful in the context of this invention include toxins, antibiotic or chemotherapeutic drugs, radioisotopes, paramagnetic ions, boron addends, cytokines, photosensitizers, radiosensitizers, vasodilators, immunomodulator agents, immune-suppressive agents, (gluco)corticoids, etc.

In a particular embodiment, the drug is a chemotherapeutic drug, such as a drug having a cytotoxic activity. The cytotoxic activity of a drug or a prodrug can be performed by means of assays that are well known in the art. For example, assessing cell membrane integrity is one of the most common ways to measure cell viability and cytotoxic effects, since compounds that have cytotoxic effects often compromise cell membrane integrity. Vital dyes, such as trypan blue or propidium iodide are normally excluded from the inside of healthy cells; however, if the cell membrane has been compromised, they freely cross the membrane and stain intracellular components. Alternatively, membrane integrity can be assessed by monitoring the passage of substances that are normally sequestered inside cells to the outside. One commonly measured molecule is lactate dehydrogenase (LDH).

Cytotoxicity can also be monitored using the MTT assay. This assay measures the reducing potential of the cell using a colorimetric reaction. Viable cells will reduce the dimethyl thiazolyl diphenyl tetrazolium salt (MTT) reagent to a coloured formazan product. A similar redox-based assay has also been developed using the fluorescent dye, resazurin. In addition to using dyes to indicate the redox potential of cells in order to monitor their viability, assays that use ATP content as a marker of viability can also be used. Such ATP-based assays include bioluminescent assays in which ATP is the limiting reagent for the luciferase reaction. Cytotoxicity can also be measured by the sulforhodamine B (SRB) assay, water soluble tetrazolium salt (WST) assay and clonogenic assay. A label-free approach to follow the cytotoxic response of adherent animal cells in real-time is based on electric impedance measurements when the cells are grown on gold-film electrodes. This technology is referred to as electric cell-substrate impedance sensing (ECIS).

In another particular embodiment, the drug is more cytotoxic than its corresponding prodrug from which the drug is released. The cytotoxicity of a compound is typically expressed as its $IC_{50}$ value. The $IC_{50}$ value, as used herein, refers to the half maximal inhibitory concentration and represents the concentration of a compound required for obtaining 50% of a maximum effect in vivo. In a particular preferred embodiment, the active drug is more cytotoxic than its corresponding prodrug. This can be estimated with the $QIC_{50}$ value, which is the ratio of the $IC_{50}$ of the prodrug/$IC_{50}$ of the drug. The $QIC_{50}$ value can be 5 or higher than 5, for example, 10 or higher than 10, $10^2$ or higher than $10^2$, $10^3$ or higher than $10^3$, $10^4$ or higher than $10^4$, or even higher. Preferably, the $QIC_{50}$ is higher than $10^2$, and more preferably, higher than $10^3$.

Illustrative, non-limitative, examples of prodrugs which can be used in the context of the present invention include glycosidic prodrugs, for example, duocarmycin-derived galactosyl prodrugs, N-(beta-D galactopyranosyloxycarbonyl)-doxorubicin and N-[4-(beta-D-galactopyranosyl)-3-nitrobenzyloxycarbonyl]daunomycin; 5-fluorocytosine; cephalosporin prodrugs, such as PROTAX (cephalosporin derivative of taxol), C-DOX (cephalosporin derivative of doxorubicin), CCM (cephalosporin mustard prodrug), etc.; palytoxin prodrug NHPAP, doxorubicin prodrug DPO, combretastatin prodrugs such as combretastatin A-4 prodrug (CA-4PD), bisphosphonate prodrugs like bisphosphonamidate clodronate etc. Prodrugs can usually be prepared using well-known methods, such as those described by Burger "Medicinal Chemistry and Drug Discovery 6th ed. (Donald J. Abraham ed., 2001, Wiley) and "Design and Applications of Prodrugs" (H. Bundgaard ed., 1985, Harwood Academic Publishers).

Alternatively, fusion proteins comprising at least the antibody of the invention linked to at least a functionally active portion of an enzyme of the invention can be constructed using recombinant DNA techniques well known in the art.

Although human, partially human, or humanised antibodies will be suitable for many applications, particularly those involving uses of the antibody in the preparation of a medicament for treatment in a human subject, other types of antibodies, i.e., of different origin, will be suitable for certain applications. The non-human antibodies of the invention can be, for example, derived from any antibody-producing animal, such as mouse, rat, rabbit, goat, donkey, or non-human primate such as monkey (e.g., cynomologous or rhesus monkey) or ape (e.g., chimpanzee). Non-human antibodies of the invention can be used, for example, in in vitro and cell-culture based applications, or any other application where an immune response to the antibody of the invention does not occur, is insignificant, can be prevented, is not a concern, or is desired.

In another aspect, the invention relates to an antibody of the invention for use in a method of treatment of a disease, wherein said method of treatment comprises killing the target cells, i.e., cells expressing CCR9 (CCR9$^+$); or, alternatively expressed, according to this aspect, the invention relates to the use of the antibody of the invention in the manufacture of a medicament for the treatment of a disease, wherein said treatment comprises killing the target cells, i.e., cells expressing CCR9 (CCR9$^+$). For this application, the antibody of the invention will be preferably administered in a pharmaceutical composition, whose particulars will be described below and which is incorporated herein by reference. In a particular embodiment, the antibody of the invention is a monoclonal antibody, such as, for example, the antibodies identified as 91R and 92R mAbs in the examples. In another particular embodiment, the target cells are tumour cells expressing CCR9 or non-tumour cells expressing CCR9, comprised in a disease or condition wherein the expression and/or amount and/or distribution of CCR9 in said cells is altered. In another particular embodiment, said disease or condition is selected from the group consisting of T-cell acute lymphoblastic leukaemia, prostate cancer, breast cancer, melanoma, ovarian cancer, colorectal cancer, lung cancer, circulating cells from a solid tumour, Crohn's disease, inflammatory bowel disease, liver fibrosis, and acute liver inflammation.

In another aspect, the invention relates to an antibody of the invention for use in tumour diagnosis by using imaging techniques wherein said tumour comprises cells expressing CCR9 (CCR9+); or, alternatively expressed, according to this aspect, the invention relates to the use of the antibody of the invention in the manufacture of a composition for in vivo tumour diagnosis by using imaging techniques wherein said tumour comprises cells expressing CCR9 (CCR9+). For this application, the antibody of the invention will be preferably administered in a pharmaceutical composition. In a particular embodiment, the antibody of the invention is a monoclonal antibody, such as, for example, the antibodies identified as 91R and 92R mAbs in the examples. In another particular embodiment, the imaging techniques are techniques used in nuclear medicine. These techniques include, without limitation, scintigraphy, SPECT, and PET. The person skilled in the art will understand that for performing these techniques it is necessary that the antibody of the invention is labelled with a suitable radionuclide. Suitable radionuclides that can be used in this aspect have been described elsewhere in the present specification and are incorporated herein by reference. In another particular embodiment, said tumour is selected from the group consisting of T-cell acute lymphoblastic leukaemia, prostate cancer, breast cancer, melanoma, ovarian cancer, colorectal cancer, lung cancer, and circulating cells from a solid tumour.

In another aspect, the invention relates to an antibody of the invention for use in targeting a drug to a tumour wherein said tumour comprises cells expressing CCR9 (CCR9+); or, alternatively expressed, according to this aspect, the invention relates to the use of the antibody of the invention in the manufacture of a composition for targeting a drug to a tumour wherein said tumour comprises cells expressing CCR9 (CCR9+). The antibody of the invention can be thus considered to be a vehicle, such as a nano-vehicle, to the tumour. For this application, the antibody of the invention will be preferably administered in a pharmaceutical composition, whose particulars will be described below and which is incorporated herein by reference. In a particular embodiment, the antibody of the invention is a monoclonal antibody, such as, for example, the antibodies identified as 91R and 92R mAbs in the examples. In another particular embodiment, the drug is selected from the group consisting of toxins, antibiotic or chemotherapeutic drugs, radioisotopes, paramagnetic ions, boron addends, cytokines, photosensitizers, radiosensitizers, vasodilators, immunomodulator agents, immune-suppressive agents, and (gluco) corticoids, whose particulars will be described below and which is incorporated herein by reference. In another particular embodiment, said tumour is selected from the group consisting of T-cell acute lymphoblastic leukaemia, prostate cancer, breast cancer, melanoma, ovarian cancer, colorectal cancer, lung cancer, and circulating cells from a solid tumour.

In another aspect, the invention relates to an antibody of the invention for use in the treatment of an inflammatory disease by depleting cells expressing CCR9 in said inflammatory disease; or, alternatively expressed, according to this aspect, the invention relates to the use of the antibody of the invention in the manufacture of a pharmaceutical composition for treating an inflammatory disease by depleting cells expressing CCR9. The antibody of the invention can be thus considered to be a vehicle, such as a nano-vehicle, to the inflammatory diseases. In an embodiment, the inflammatory disease is an inflammatory disease wherein cells expressing CCR9 participate and the antibody of the invention depletes cells expressing CCR9 that participate in said inflammatory disease. For this application, the antibody of the invention will be preferably administered in a pharmaceutical composition, whose particulars will be described below and which is incorporated herein by reference. In a particular embodiment, the antibody of the invention is a monoclonal antibody, such as, for example, the antibodies identified as 91R and 92R mAbs in the examples. In another particular embodiment, the drug is selected from the group consisting of toxins, antibiotic or chemotherapeutic drugs, radioisotopes, paramagnetic ions, boron addends, cytokines, photosensitizers, radiosensitizers, vasodilators, immunomodulator agents, immune-suppressive agents, and (gluco) corticoids, whose particulars will be described below and which is incorporated herein by reference. In another particular embodiment, said inflammatory disease is selected from the group consisting of Crohn's disease, inflammatory bowel disease, liver fibrosis, and acute liver inflammation.

Another aspect of the invention relates to the use of the antibody of the invention as a tool in biotechnology techniques for detection, localization and/or quantification of CCR9 protein in a sample, hereinafter "third use of the invention".

Thus, the antibody of the invention can also be labelled with a detectable label or labelling agent that allows its location and/or identification by spectroscopic, photochemical, biochemical, immunochemical or chemical means. Thus, in a particular embodiment, the antibody of the invention comprises a labelling agent.

The term "detectable label" or "labelling agent", as used herein, refers to a molecular label which allows the detection, localization and/or identification of the molecule to which it is attached, using suitable procedures and equipment for detection, either by spectroscopic, photochemical, biochemical, immunochemical or chemical means.

Thus, in a particular embodiment, the antibody of the invention is modified so that subsequent detection possible. Thus, the invention contemplates the possibility of modifying the antibody of the invention with a detectable agent that permits detection of the antibody. Non-limitative examples of detectable agents include radioisotopes and fluorescent groups.

In a particular embodiment, the antibody of the invention is modified with a radioisotope. Non-limitative examples of radioisotopes suitable for the invention include $^{3}H$, $^{11}C$, $^{14}C$, $^{18}F$, $^{32}P$, $^{35}S$, $^{64}Cu$, $^{68}Ga$, $^{86}Y$, $^{99}Tc$, $^{111}In$, $^{123}I$, $^{124}I$, $^{125}I$, $^{131}I$, $^{133}Xe$, $^{177}Lu$, $^{211}At$ and $^{213}B$. Radioisotope labelling is performed typically by using chelating ligands that are capable of complexing metal ions such as DOTA, DOTP, DOTMA, DTPA and TETA. Methods for conjugating radioisotopes to proteins are well known in the prior art.

In another particular embodiment, the antibody of the invention is labelled with a fluorescent group. The fluorescent group can be attached to the side chains of the amino acids directly or through a linking group. Methods for conjugating polypeptides fluorescent reagents are well known in the prior art.

Suitable reagents for labelling polypeptides, such as antibodies, with fluorescent groups include chemical groups which show ability to react with the various groups listed in the side chains of the proteins, including amino groups and thiol groups. Thus, chemical groups that can be used to modify the antibodies according to the present invention include, without limitation, maleimide, haloacetyl, iodoacetamide succinimidyl ester (e.g. NHS, N-hydroxysuccinimide), isothiocyanate, sulfonyl chloride, 2,6-dichlorotriazinyl, pentafluorophenyl ester, phosphoramidite and the like. An example of suitable reactive functional group is N-hydroxysuccinimide ester (NHS) of a detectable group modified with a carboxyl group. Typically, the carboxyl group modifying the fluorescent compound is activated by the contacting of said compound with a carbodiimide reagent (for example, dicyclohexylcarbodiimide, diisopropylcarbodiimide, uronium or a reagent such as TSTU (O—(N-Succinimidyl)-N,N,N',N'-tetramethyluronium tetrafluoroborate), HBTU ((O-benzotriazol-1-yl)-N,N,N',N'-tetramethyluronium hexafluorophosphate), or HATU (O-(7-azabenzotriazol-1-yl)-N,N,N',N'-tetramethyluronium hexafluorophosphate), an activator of the type of 1-hydroxybenzotriazole (HOBt) and N-hydroxysuccinimide to give the NHS ester of the label.

Fluorescent compounds suitable for use in the third use of the invention include, without limitation, ethidium bromide, SYBR® Green brand fluorescent dye, fluorescein isothiocyanate (FITC), rhodamine tetramethyl isotiol (TRIT), 5-carboxyfluorescein, 6-carboxyfl uorescein, fluorescein, HEX (6-carboxy-2',4,4',5',7,7'-hexachlorofluorescein), Oregon Green 488, Oregon Green 500, Oregon Green 514, Joe (6-carboxy-4',5'-dichloro-2', 7'-dimethoxyfluorescei n), 5-carboxy-2',4',5',7'-tetrachlorofluorescein,5-carboxyrhodamine, rhodamine, tetramethylrhodamine (Tamra), Rox (carboxy-X-rhodamine), R6G (rhodamine 6G), phthalocyanines, azometazinas, cyanines (Cy2, Cy3 and Cy5), TEXAS RED® brand fluorescent dye, Princeton Red, BODIPY FL-Br2, BODIPY 530/550, BODIPY® brand fluorescent dye TMR, BODIPY® brand fluorescent dye 558/568, BODIPY® brand fluorescent dye 564/570, BODIPY® brand fluorescent dye 576/589, BODIPY® brand fluorescent dye 581/591, BODIPY® brand fluorescent dye TR, BODIPY® brand fluorescent dye 630/650, BODIPY® brand fluorescent dye 650/665, DABCYL, eosin, erythrosin, ethidium bromide, green fluorescent protein (GFP) and its analogues, inorganic-based fluorescent semiconductor nanocrystals (Quantum Dot), fluorescent labels based on lanthanide such as $Eu^{3+}$ and $Sm^{3+}$ and the like.

In another particular embodiment, the antibody of the invention is labelled by conjugation to a first member of a binding pair. In a preferred embodiment, this modification is covalent biotinylation. The term "biotinylation", as used herein, refers to the covalent attachment of biotin to a molecule (typically a protein). Biotinylation is performed using biotin reagents capable of conjugating to the side chain of the proteins, wherein said conjugation occurs primarily on the primary amino groups and thiol groups contained in the side chains of proteins. Suitable reagents for biotinylation of amino groups include molecules containing biotin and a group capable of reacting with amino groups such as succinimide esters, pentafluorophenyl ester or alkyl halides, wherein the biotin moiety and the reactive group separated by a spacer of any length (for example, 8-40 A in length). Some examples of these agents include agents biotinylation NHS-biotin (containing an ester bond of five carbon atoms between biotin and NHS group), sulfo-NHS-biotin, NHS-LC-biotin, sulfo-NHS-LC-biotin, NHS-LC-LC-biotin, sulfo-NHS-LC-LC-biotin, sulfo-NHS-SS-biotin, NHS-PEO$_4$-biotin, PFP-biotin, TFP-PEO-biotin and the like, where "NHS" indicates an N-hydroxysuccinimide, "LC" refers to an amide bond of 6 carbon atoms located between NHS and biotin group, "PEO" refers to a etileneoxyde group, where the subscript indicates the number of units PEO, "PFP" refers to a pentafluorophenyl group "TFP" refers to a tetrafluorophenyl group, "sulfo" refers to a sulfonate group ($SO_3$) and "SS" refers to a disulfide group. Examples of biotinylation reagents with thiol groups include molecules comprising a group of biotin and maleimide or alkyl halide type, separated by a spacer of any length. Examples of biotinylation reagents include maleimide-PEG-biotin, biotin-BMCC (containing a maleimido group N-terminal and a cyclohexyl group, 2 amide and 9 carbon atom linkers), PEO-iodoacetil biotin, iodoacetil-LC-biotin, biotin-HPDP (containing a pyridyl disulfide) and the like.

In another particular embodiment, the antibody of the invention is labelled with metal ions such as gold (Au), including colloidal gold nanoparticles can be attached directly to the antibody via electrostatic interactions. In another particular embodiment, the colloidal gold nanoparticles are pre-coupled to biotin and can be covalently attached to the antibody.

It is another aspect of the invention the use of the antibody of the invention in the detection and/or quantification of CCR9, or cells expressing CCR9, present in a sample. The detection and/or quantification of CCR9, or cells expressing CCR9, present in a sample, by the antibody of the invention, can be carried out in vitro. Using the antibody of the invention can be carried with any immunochemical or immunofluorescent assay for the detection, identification and/or quantification of the presence of CCR9, or cells expressing CCR9, in a sample. Examples of immunochemical or immunofluorescent assays include, without limitation, immunosensors, immunoprecipitation, Western blot, dot blot, radioimmunoassay, immunofluorescence, immunocytochemistry, immunohistochemistry and flow cytometry.

Using the antibody of the invention for the detection, identification and/or quantification of the presence of CCR9, or cells expressing CCR9, in a sample requires to put into practice an in vitro method for detecting and/or quantifying the presence of CCR9, or cells expressing CCR9, in a sample, comprising:
  i) contacting the test sample with the antibody of the invention,
  ii) detecting and/or quantifying the formation of immune complexes with said antibody.

Said method constitutes an additional aspect of the present invention.

One can use any of a wide variety of formats of immunochemical analysis using the method of the present invention. Analysis such immunochemical techniques include, without limitation, ELISA, immunoassay strip or LFIA, immunosensors, immunoaffinity extraction systems, immunoprecipitation, Western blot, dot blot, radioimmunoassay, immunofluorescence, flow cytometry, immunocytochemistry and immunohistochemistry.

As the person skilled in the art will realise, the detection, identification and/or quantification of the presence of CCR9 in a sample enables the use of the antibody of the invention in a number of applications including the detection of $CCR9^+$ circulating tumour cells, the phenotypic analysis of $CCR9^+$ cellular subpopulations, in particular, of $CCR9^+$ stem cells.

The detection of $CCR9^+$ circulating tumour cells usually involves a step of circulating tumour cell enrichment, which includes a large panel of technologies based on the different properties of circulating tumour cells that distinguish them from the surrounding normal blood cells, including physical properties (size, density, electric charges, deformability) and biological properties (surface protein expression, mostly EpCAM expression, as well as CCR9 expression). After enrichment, the circulating tumour cells fraction usually still contains a substantial number of leukocytes, and circulating tumour cells need to be, therefore, identified by a method that can distinguish tumor cells from normal blood cells at the single cell level. Among the protein-based strategies, cells are fluorescently stained for cytokeratins (CK; positive marker), the common leukocyte antigen CD45 (negative marker), and a nuclear dye (DAPI); circulating tumour cells are identified as CK+/CD45−/DAPI+ cells. The sample enriched in circulating tumour cells can be then tested for the presence of CCR9+ cells through a number of different assays, e.g. by direct detection with the anti-CCR9 antibody of the invention, or with a circulating tumour cell-chip consisting of an array of microposts coated with the anti-CCR9 antibody of the invention The antibody of the invention can also be used in the phenotypic analysis of CCR9+ cellular subpopulations, in particular, of CCR9+ stem cells. e.g. as part of a microarray for phenotyping mammalian cells.

The antibody of the invention may also be used in the isolation or purification of cells expressing CCR9, for example mesenchymal stem cells. Thus, it is another aspect of the present invention the use of the antibody of the invention in the isolation and/or purification of cells expressing CCR9, for example mesenchymal stem cells. The person skilled in the art will realise that the mesenchymal stem cells isolated using this application are useful in regenerative cell therapies.

One can use a wide variety of formats, either in solid or soluble phase, for the isolation and/or purification of cells expressing CCR9.

A particular application of the antibody of the invention is in techniques such as leukopheresis. As used herein, the term "leukopheresis" refers to the procedure in which white blood cells are separated from the blood, and the remaining components are returned to the blood circulation. It is thus an extracorporeal therapy (a medical procedure performed outside the body). One way to carry out the leukopheresis is by using a selective leukopheresis column coupled with the antibody of the invention. The person skilled in the art will realise that this application will be useful, for example, in the treatment of inflammatory bowel disease (Eberhardson et al., 2013, Clin Immunol. 149:73-82).

Kits of the Invention

The present invention also provides kits for carrying out the above-described methods and uses.

Thus, in another aspect, the invention relates to a kit, hereinafter the "kit of the invention", comprising at least an antibody of the invention.

In a particular embodiment, the kit of the invention comprises, in addition to the antibody of the invention, a further therapeutic agent. The particulars of said therapeutic agent have been previously described in connection with the therapeutic uses of the antibody of the invention (see, for example, first and second use of the invention) and are incorporated herein by reference. In a particular embodiment, said therapeutic agent can be conjugated to, or forming a fusion protein with, the antibody of the invention.

In the context of the present invention, "kit" is understood as a product containing the different reagents necessary for carrying out the methods of the invention packed so as to allow their transport and storage. Materials suitable for packing the components of the kit include crystal, plastic (polyethylene, polypropylene, polycarbonate and the like), bottles, vials, paper, envelopes and the like. Additionally, the kits of the invention can contain instructions for the simultaneous, sequential or separate use of the different components which are in the kit. Said instructions can be in the form of printed material or in the form of an electronic support capable of storing instructions such that they can be read by a subject, such as electronic storage media (magnetic disks, tapes and the like), optical media (CD-ROM, DVD) and the like. Additionally or alternatively, the media can contain Internet addresses that provide said instructions.

The kit of the invention can be used for diagnosing and/or prognosing a disease or condition wherein cells expressing CCR9 participate, including, among others, CCR9+ tumour diagnosis by using imaging techniques, or for monitoring the response to treatment of a disease or condition wherein cells expressing CCR9 participate in a subject under treatment, or for treatment a disease or condition wherein cells expressing CCR9 participate, including, among others, treatment methods comprising killing the target cells (CCR9+) as well as treatment methods of inflammatory diseases by depleting cells expressing CCR9, or for targeting a drug to a tumour wherein said tumour comprises CCR9+ cells, or as a tool in biotechnology techniques, such as for example, biotechnology techniques for detection, localization and/or quantification of CCR9 protein in a sample, or for the detection and/or quantification of CCR9, or cells expressing CCR9, present in a sample.

Therefore, in another aspect, the invention relates to the use of the kit of the invention:

for diagnosing and/or prognosing a disease or condition wherein cells expressing CCR9 participate;

for monitoring the response to treatment of a disease or condition wherein cells expressing CCR9 participate in a subject under treatment;

for treatment a disease or condition wherein cells expressing CCR9 participate;

for targeting a drug to a tumour wherein said tumour comprises CCR9+ cells;

as a tool in biotechnology techniques for detection, localization and/or quantification of CCR9 protein in a sample; or for detecting and/or quantifying CCR9, or cells expressing CCR9, present in a sample.

The terms "antibody" and "disease or condition wherein cells expressing CCR9 participate" have been described in detail in the context of the antibody invention and the methods of diagnosis/prognosis of the invention, and the terms and their particulars are equally applied to the first kit of the invention.

In a preferred embodiment of the kit of the invention, the antibody of the invention comprises within the heavy chain a CDR-H1 consisting of the amino acid sequence shown in SEQ ID NO: 1, a CDR-H2 consisting of the amino acid sequence shown in SEQ ID NO: 2, and a CDR-H3 consisting of the amino acid sequence shown in SEQ ID NO: 3, and comprising within the light chain a CDR-L1 consisting of the amino acid sequence shown in SEQ ID NO: 4, a CDR-L2 consisting of the amino acid sequence shown in SEQ ID NO: 5, and a CDR-L3 consisting of the amino acid sequence shown in SEQ ID NO: 6.

In another preferred embodiment of the kit of the invention, the antibody of the invention comprises within the heavy chain a CDR-H1 consisting of the amino acid sequence shown in SEQ ID NO: 7, a CDR-H2 consisting of the amino acid sequence shown in SEQ ID NO: 2, and a CDR-H3 consisting of the amino acid sequence shown in SEQ ID NO: 3, and comprising within the light chain a CDR-L1 consisting of the amino acid sequence shown in SEQ ID NO: 8, a CDR-L2 consisting of the amino acid sequence shown in SEQ ID NO: 9, and a CDR-L3 consisting of the amino acid sequence shown in SEQ ID NO: 10.

Pharmaceutical Compositions

In another aspect, the invention relates to a pharmaceutical composition, hereinafter "pharmaceutical composition of the invention", comprising a therapeutically effective amount of an antibody of the invention, or a pharmaceutically derivative or prodrug thereof, together with a pharmaceutically acceptable excipient, carrier, adjuvant, or vehicle, for administration to a subject. Said pharmaceutical composition can be used for killing or for inducing apoptosis of cells expressing CCR9 upon administration to a subject having a disease or condition wherein cells expressing CCR9 participate.

The term "pharmaceutically acceptable carrier", as used herein, is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as TWEEN® brand non-ionic detergent, PLURONIC® brand non-ionic surfactant or polyethylene glycol (PEG).

The antibodies of the invention may be in the same formulation or may be administered in different formulations. Administration can be concurrent or sequential, and may be effective in either order.

Supplementary active compounds can also be incorporated into the pharmaceutical composition of the invention. Thus, in a particular embodiment, the pharmaceutical composition of the invention may also contain more than one active compound as necessary for the particular indication being treated, preferably those with complementary activities that do not adversely affect each other. For example, it may be desirable to further provide a chemotherapeutic agent, a cytokine, an analgesic agent, or an immunosuppressive agent. The effective amount of such other active agents depends, among other things, on the amount of antibody of the invention present in the pharmaceutical composition, the type of disease or disorder or treatment, etc.

In an embodiment, the antibody of the invention is prepared with carriers that will protect said compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. These can be prepared according to methods known to those skilled in the art, for example, as described in U.S. Pat. No. 4,522,811.

The administration route of the antibody (or fragment thereof) of the invention may be intratumoural or parenteral.

The term "parenteral" as used herein includes intravenous, intraperitoneal, intramuscular, subcutaneous, rectal or vaginal administration. The intravenous form of parenteral administration is generally preferred. The amount of an antibody required for therapeutic or prophylactic effect will, of course, vary with the antibody chosen, the nature and severity of the condition being treated and the patient.

In addition, the antibody may suitably be administered by pulse infusion, e.g., with declining doses of the antibody. Preferably the dosing is given by injections, most preferably intravenous or subcutaneous injections, depending in part on whether the administration is brief or chronic.

In another embodiment, the pharmaceutical compositions of the invention may be adapted for parenteral administration, such as sterile solutions, suspensions or lyophilized products in the appropriate unit dosage form. Pharmaceutical compositions suitable for injectable use include sterile aqueous solutions (where water soluble) or dispersions and sterile powders for the extemporaneous preparation of sterile injectable solutions or dispersions. For intravenous administration, suitable carriers include physiological saline, bacteriostatic water, CremophorEM (BASF, Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, a pharmaceutically acceptable polyol like glycerol, propylene glycol, liquid polyetheylene glycol, and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, and sodium chloride in the composition. Prolonged absorption of the injectable compositions can be brought about by including in the composition an agent which delays absorption, for example, aluminum monostearate and/or gelatin.

Sterile injectable solutions can be prepared by incorporating the active compound (e.g., a polypeptide or antibody) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

In a particular embodiment, said pharmaceutical composition is administered via intravenous or intratumoural. Adequate excipients can be used, such as bulking agents, buffering agents or surfactants. The mentioned formulations will be prepared using standard methods such as those described or referred to in the Spanish and US Pharmacopoeias and similar reference texts.

It is especially advantageous to formulate the pharmaceutical compositions, namely, oral or parenteral compositions, in dosage unit form for ease administration and uniformity of dosage. Dosage unit form as used herein refers to physically discrete units suited as unitary dosages for the subject to be treated; each unit containing a predetermined quantity of active compound (antibody of the invention) calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

Generally an effective administered amount of an antibody of the invention will depend on the relative efficacy of the compound chosen, the severity of the disorder being treated and the weight of the sufferer. However, active compounds will typically be administered once or more times a day for example 1, 2, 3 or 4 times daily, with typical total daily doses in the range of from 0.001 to 1,000 mg/kg body weight/day, preferably about 0.01 to about 100 mg/kg body weight/day, most preferably from about 0.05 to 10 mg/kg body weight/day.

Aside from administration of antibodies to the patient, the present application contemplates administration of antibodies by gene therapy. WO96/07321 relates the use of gene therapy to generate intracellular antibodies.

The pharmaceutical compositions can be included in a container, pack, or dispenser together with instructions for administration.

The antibodies and pharmaceutical compositions of this invention may be used with other drugs to provide a combination therapy. The other drugs may form part of the same composition, or be provided as a separate composition for administration at the same time or at different time. Non-limitative examples of drugs suitable in combination therapy are antagonists of CCR9 such as those described in US2005/0049286, the CCL25-PE38 fusion protein (Hu et al., 2011, cited supra).

The antibodies and pharmaceutical compositions of the present invention will be useful in the treatment of medical conditions, such as diseases and conditions wherein cells expressing CCR9 participate, specially, for treating T-cell acute lymphoblastic leukaemia, prostate cancer, breast cancer, melanoma, Crohn's disease, inflammatory bowel disease.

In another particular embodiment, the antibody of the invention is coupled to a nanocontainer loaded with at least one therapeutic agent. Upon administration, the nanocontainer coupled to the antibody of the invention is thus directed to the target cells, i.e., cells expressing CCR9. Liposomes and nanoparticles are exemplary forms of nanocontainers that are commonly used. The liposomes preferably have diameters of less than 200 nanometers. Liposomes having diameters of between 50 and 150 nanometers are preferred. Especially preferred are liposomes or other nanocontainers having external diameters of about 80 nanometers. Suitable types of liposomes are made with neutral phospho lipids such as 1-palmitoyl-2-oleoyl-sn-glycerol-3-phosphocholine (POPC), diphosphatidyl phosphocholine, distearoylphosphatidylethanolamine (DSPE), or cholesterol, along with a small amount (1%) of cationic lipid, such as didodecyldimethylammonium bromide (DDAB) to stabilize the DNA within the liposome.

Other suitable containers for the use of the antibodies of the invention include dendrimers. The term "dendrimer" refers to a macromolecule having a core and having multiple shells of branching structures emanating from the core. The shape and size of a dendritic carrier can vary. In some instances, the dendritic carrier can be approximately spherical or globular in shape. Furthermore, the dendritic carrier can have a diameter in the range of about 15 angstroms (A) to about 250 A, with a corresponding range of molecular weights, e.g., from about 500 Daltons to about 2 million Daltons. Dendrimers can be obtained commercially from various sources (e.g., Dendritech, Midland, Mich.) or synthesized by methods known to those skilled in the art. Dendritic molecules can roughly be divided into the low-molecular weight and the high-molecular weight species. The first category includes dendrimers and dendrons whereas the second encompasses dendronized polymers, hyperbranched polymers, and brush-polymers (also called bottle-brushes). Dendrimers and dendrons are repeatedly branched, monodisperse, and usually highly symmetric compounds. There is no apparent difference in defining dendrimer and dendron. A dendron usually contains a single chemically addressable group that is called the focal point. Because of the lack of the molar mass distribution high-molar-mass dendrimers and dendrons are macromolecules but not polymers. The properties of dendrimers are dominated by the functional groups on the molecular surface. Dendritic encapsulation of functional molecules allows for the isolation of the active site, a structure that mimics the structure of active sites in biomaterials because dendritic scaffolds separate internal and external functions. For example, a dendrimer can be water-soluble when its end-group is a hydrophilic group, like a carboxyl group.

Dendrimers may be generally characterised by the following features: (i) an initiator core (I) which may have one or more reactive sites and be point-like or of significant size so as to effect the final topology of the dendrimer; (ii) one or more layers of branched repeating units attached to the initiator core; (iii) functional terminal groups, such as anionic or cationic groups, attached, optionally through linking groups, to the surface of the dendrimer.

Dendrimers contemplated herein may comprise lysine, or lysine analogue building units. The term "lysine analogue" refers to a molecule which has a single apex carboxyl group for attachment to the previous layer of building units, and two or three primary amine groups to which can be attached further building units, blocking groups, linkers or aryl acid groups. Examples of "lysine analogues" contemplated herein are described in PCT/AU2007/000352, for example glycyl-lys. In some particular examples, the dendrimer comprises only lysine or one type of lysine analogue as the building unit.

Other dendrimers contemplated herein include those comprising polyamidoamine (PAMAM), poly(etherhydroxylamine) (PEHAM) or polypropyleneimine building units. In particular examples thereof, the dendrimer has only polyamidoamine (PAMAM), poly(etherhydroxylamine) (PEHAM) or polypropyleneimine as the building unit.

The core moiety may contain only 1 point of attachment for a building unit or may contain 2, 3 or more points, which may or may not be further utilized for the attachment of building units. Typically, the point of attachment is a free amino group. Core moieties may consist of, comprise or be derived from a building unit or may be a molecule different to the building units. Exemplary core moieties are illustrated herein and described in PCT/AU2007/000352.

The liposomes and dendrimers may be combined with any suitable pharmaceutical carrier for intravenous administration. Intravenous administration of the composition is the preferred route since it is the least invasive. Other routes of administration are possible, if desired. Suitable pharmaceutically acceptable carriers include saline, Tris buffer, phosphate buffer, or any other aqueous solution. An appropriate dosage can be established by procedures well known to those of ordinary skill in the art.

The liposomes and dendrimers coupled to the antibody according to the invention may encapsulate any of the therapeutic agents mentioned above which are capable of killing the target cells.

The following examples illustrate the invention and must not be considered in a limiting sense thereof.

EXAMPLES

Materials and Methods
Cells and Reagents

Human embryonic kidney 293 (HEK293) cells and HEK293 cells stably transfected with chemokine receptors hCCR6 and hCCR8 were cultured as described (Zaballos et al., 1999, J Immunol 162:5671-5; Carramolino et al., 1999, J Leukocyte Biol 66:837-44; Goya et al., 1998, 160:1975-81). hCCR4, hCCR5 and hCCR9 transfectants were a kind gift of A. Zaballos (Instituto de Salud Carlos III, Madrid, Spain). MOLT-4 (CRL-182) and Jurkat (TIB-152) human T-cell acute lymphoblastic leukaemia cell lines were from the ATCC (Manassas, Va.). Bioluminescent MOLT-4 cells (MOLT-4-luc) were generated by infection with a recombinant lentivirus encoding EGFP and red luciferase (Promega, Palo Alto, Calif.). Infected cells expressing high EGFP levels were isolated by FACS, cloned, expanded, and used for in vivo bioluminescence assays. MOLT-4-luc cell growth was similar to parental MOLT-4 cells and they retained surface CCR9 expression. Cells were cultured in DMEM supplemented with 10% fetal bovine serum (FBS, Lonza, Switzerland), 2 mM L-glutamine, 50 U/ml penicillin, and 50 µg/ml streptomycin (complete medium). Human peripheral blood lymphocytes and thymocytes from thymic fragments removed during corrective cardiac surgery were obtained after receiving informed patient consent in accordance with the Declaration of Helsinki.

Recombinant human CCL25 and CXCL12 were from Peprotech (London, UK). The following antibodies were used: anti-hCCR9 (112509, mouse mAb IgG2a; R&D, Abingdon, UK), mCCR9 (K629; rabbit Ab; Carramolino et al., 2001, Blood 97:850-7), hCD3-FITC (UCHT1), hCD4-PcyS (13B8.2), hCD8-PE (B9.11) (all three from Beckman Coulter, Miami, Fla.), hCD31 (MEC 13.3; rat mAb; BD Biosciences, San Jose, Calif.), hCD71 transferrin receptor (H300; rabbit Ab), PCNA (PC10; mouse mAb) (both from Santa Cruz Biotech) and control antibodies P-020 (mouse mAb IgG2b; inventor's laboratory) and MPC-11 (mouse mAb IgG2a; BD Biosciences). The 3C3 anti-hCCR9 mAb was produced from the LS123-3C3-E3-1 hybridoma (ATCC Accession No. HB12653).

Generation of Human CCR9-Specific mAb

Murine mAb to human CCR9 were raised by gene gun (Bio-Rad, Hercules, Calif.) particle-mediated DNA administration of the pClneo plasmid bearing the human CCR9 sequence to-BALB/c mice. DNA was coated onto 1.6 nm gold particles and the DNA/gold complex (2 µg/day) was delivered to each mouse; mice were boosted on days 30 and 60 with the same amount of plasmid. Sera were collected 7-10 days after the last boost and tested for specific antibodies by flow cytometry using stably transfected hCCR9-HEK293 and pClneo-HEK293 cells as negative control. Selected mice were boosted intravenously with $10^7$ hCCR9-HEK293 cells on days −3 and −2, followed by splenocyte fusion with the P3X63Ag8.653 plasmacytoma (Kremer et al., 2004, Methods Mol Biol 239:243:60). Two weeks post-fusion, culture supernatants were screened by flow cytometry for CCR9-specific antibodies using hCCR9-HEK293 cells. Positive hybridomas were cloned, mAb purified from tissue culture supernatants and antibody isotype determined by ELISA (Kremer et al., 2004, cited supra).

Generation of Chimeric CCR9 pClneo expression vectors bearing human or mouse CCR9 cDNA inserted in NheI-EcoRI sites were used to generate chimeric CCR9. Both vectors were digested with NheI and BspLI, and the fragment containing 62 N-terminal amino acids of the murine CCR9 sequence was cloned into the digested human CCR9 plasmid to generate the mNt/hCCR9 expression vector, which was transiently transfected in HEK293 cells. Chimeric CCR9 expression was evaluated by flow cytometry.

Flow Cytometry

For staining, $2\times10^5$ cells/well were centrifuged in V-bottom 96-well plates and washed with PBS containing 0.5% bovine serum albumin (BSA), 1% FBS and 0.1% sodium azide (PBSst). Non-specific binding was blocked by preincubation of cells with 40 µg/ml rat IgG (Sigma, St Louis, Mo.; 20 min, 4° C.). Cells were incubated with primary Ab (30 min, 4° C.), washed, and incubated with FITC- or PE-goat F(ab')₂ anti-mouse IgG (H+L) (Beckman Coulter; 30 min, 4° C.). Samples were analyzed with an EPICS® XL™ brand cytometer or a Cytomics cytometer (Beckman Coulter).

For competition studies using specific chemokines, cells were incubated with 50µ 1 hCCL25 or hCXCL12 (10 µg/ml, 40 min, 4° C.), followed by addition of 50 µl 91R or isotype-matched mAb (0.5 µg/ml, 30 min, 4° C.). After washing, the FITC-goat anti-mouse IgG antibody was added (30 min, 4° C.). CCR9 expression was evaluated by flow cytometry.

For competition studies with 91R, 92R mAbs and the 3C3 anti-hCCR9 mAb, MOLT4 cells ($2\times10^5$ cells/well) were pre-incubated with 50 µl of PBSst (filled histograms) or with 3C3, 91R, 92R or isotype control mAbs (20 µg/ml, open histograms). After 30 min at 4° C., another 50 µl of biotin-labeled 3C3, 91R or 92R mAbs (5 µg/ml) were added and the incubation continued for 20 additional min. After a washing step, antibody binding to MOLT4 cells was evaluated by flow cytometry.

Western Blot Assays

To extract the membrane fraction, cell pellets ($5\times10^6$ cells) were resuspended in hypotonic buffer (5 mM Tris/HCl pH 7.4, 50 mM NaCl, 1 mM MgCl₂, 2 mM EGTA), subjected to four freeze-thaw cycles and centrifuged (750×g, 2 min, 4° C.). Supernatants were centrifuged (18,000×g, 30 min, 4° C.). Membrane pellets were resuspended in PBS with HALT™ Protease Inhibitor Cocktail brand protease inhibitor reagent (THERMO SCIENTIFIC™, Rockford, Ill.), solubilized in 20% SDS, 100 mM dithiothreitol (30 min, room temperature (RT)) and resolved by SDS-PAGE. Proteins were transferred to IMMOBILON® brand PVDF membranes (Millipore, Billerica, Mass.), blocked (5% BSA, 5% non-fat dry milk and 0.05% TWEEN® 20 brand non-ionic detergent in PBS), then immunoblotted with 91R mAb (1 µg/ml, 2 h, RT) and incubated with a peroxidase-coupled goat anti-mouse IgG antibody. Membranes were reprobed with anti-hCD71 Ab (0.4 µg/ml, 2 h, RT) as loading control. Blots were developed using ECL (GE, Pittsburgh, Pa.). Where indicated, samples were N-deglycosylated using peptide-N-glycosidase F (PNGase F, New England Biolabs, Ipswich, Mass.; 1 h, 37° C.).

ELISA

Microtiter plates were coated with synthetic peptides [hCCR9 amino acids 2-22 (SEQ ID NO: 11) or 13-30 (SEQ ID NO: 12), or BOT, a non-related control peptide], goat anti mouse kappa light chain antibody (GaM kappa LC; Bethyl Laboratories, Montgomery, Tex., USA) or BSA. Plates were blocked with BSA, and 3C3, 91R, BOT or isotype control mAbs were added. After washing, a horseradish peroxidase-conjugated goat anti mouse immunoglobulin (Dako, Denmark) was used. After incubation, plates were washed and developed with OPD and $H_2O_2$. Results were quantified by measuring absorbance at 490 nm.

Sequencing of CDRs of 3C3 mAb

Total hybridoma 3C3 (LS129-303-E3-1; ATCC Accession No. HB12653) RNA was extracted from frozen hybridoma cell lysates in TRIZOL® brand RNA isolation reagent (Ambion). Total RNA was reverse transcribed into cDNA using isotype-specific anti-sense primers or universal primers following the technical manual of PRIMESCRIPT™ brand 1st Strand cDNA Synthesis Kit (Takara). The antibody fragments of VH and VL were amplified according to the standard operating procedure of RACE of GenScript, which were then cloned separately into a standard cloning vector and sequenced (GenScript). The CDRs were matched following Kabat numbering.

Migration Assays

Transwell plates with 5 µm pore size (Corning-Costar) were used. The lower chambers were filled with 500 µl of migration medium (DMEM, 0.1% BSA, 10 mM HEPES) supplemented with 200 nM recombinant hCCL25 (Pepro-tech). $3 \times 10^5$ MOLT-4 cells were pre-incubated in 100 µl migration medium with the corresponding mAb (100 µg/ml) for 15 min at room temperature, placed in the upper chambers and allowed to migrate for 3 h at 37° C. Migrated cells in the lower chambers were counted using a flow cytometer.

Xenograft Assays

BALB/c $Rag2^{-/-}$ mice (Taconic Farms, Hudson, N.Y.) were bred in the CNB animal facility and used when 8 to 22 weeks old. Maintenance and treatment protocols followed EU and national guidelines for animal experimentation and were approved by the CNB/CSIC Ethics Committee.

For in vivo experiments, MOLT-4 cells ($2 \times 10^6$) were inoculated subcutaneously (s.c.) on day 0 in each flank of $Rag2^{-/-}$ mice; two groups of 6 mice each were then inoculated intraperitoneally (i.p.) with anti-hCCR9 91R or $IgG_{2b}$ control mAb on days 1, 7, 14 and 21 (4 mg/kg on d1 and 6; 2 mg/kg on d13 and 21). In a second experiment, MOLT-4 cells ($2 \times 10^6$) were inoculated s.c. into one flank of female $Rag2^{-/-}$ mice; two groups of 10 mice each were inoculated i.p. with anti-hCCR9 91R or $IgG_{2b}$ control mAb on days 7, 14, 21 and 28 (4 mg/kg on d7 and 14; 2 mg/kg on d28 and 35). Tumour size was measured with a vernier caliper (Mitutoyo, Kanawaga, Japan) and tumour volume ($mm^3$) calculated as V=[axial diameter length, mm]×[(rotational diameter, mm)$^2$/2]. Tumour burden is expressed as percent tumour volume relative to that of IgG2b-treated mice. Mice were sacrificed on day 56 or 69, depending on the experiment; mice and tumours were weighed and processed for histology.

For bioluminescence xenograft assays, female Rag2 mice were inoculated s.c. in each flank with $2 \times 10^6$ MOLT-4-luc cells on d0. After 24 h, mice were anesthetized and D-luciferin (150 mg/kg) was administered to allow imaging and luminescence quantification for balanced assignment to experimental groups. Mice (7/group) were inoculated i.p. with 91R or isotype control P-020 mAb on d1 (4 mg/kg) and d6 (2 mg/kg). Luminescence imaging was repeated at six time points until mice were sacrificed on d62. Mice were anesthetized with Imalgene 500 (2 ml/Kg; Merial Laboratories, France) and Xilagesic 2% (0.6 ml/Kg; Calier Laboratories, Spain) 10 min before analysis. Imaging was done with a 1394 ORCA II ERG camera (Hamamatsu, Japan) in a lightproof chamber for 100 sec; Wasabi software (Hamamatsu) was used to quantify the data and produce pseudo-color images.

Histology and Quantification of Necrotic Area

Dissected tumours were divided in half; one half was fixed in 4% paraformaldehyde (pH 7.4) overnight, washed in PBS, paraffin-embedded and sectioned (5 µm). The other half was embedded in OCT (Leica Microsystems, Wetzlar, Germany), snap-frozen in dry ice-chilled isopentane, stored at −80° C., and later sectioned (8 µm).

Paraffin-embedded sections were hematoxylin/eosin-stained by standard procedures and mounted in Micromount media (Leica Microsystems). Images were captured on a Zeiss Axiophot microscope (Carl Zeiss, Germany) with a Digital Sight camera (Nikon, Japan). Total tumour section and necrotic areas were quantified with NIH ImageJ software.

Deoxynucleotidyl Transferase-Mediated dNTP-Biotin Nick End Labeling (TUNEL)

To measure cell death by TUNEL, paraffin-embedded sections were dewaxed and rehydrated, then permeabilized (PBS, 0.5% Triton X-100; RT, 10 min). Slides were pre-incubated (RT, 15 min in the dark, humidified chambers) with TdT buffer pH 6.6 (Sigma) and 1 mM $CoCl_2$. Sections were incubated with reaction mix (recombinant terminal transferase and biotin-16-dUTP; Roche, UK) and washed in preincubation buffer (RT, 10 min). The reaction was terminated with PBS and 0.01% Tween 20, slides were incubated with streptavidin-Cy5 (Jackson Immunoresearch; Zymed, USA; 1 h, RT).

Immunohistochemistry (IHC)

Cell proliferation was quantified by labeling proliferating cell nuclear antigen (PCNA) in dewaxed and rehydrated paraffin-embedded sections. Antigens were exposed by steaming in sodium citrate buffer (15 min), stained with the MAXFLUOR™ brand Mouse on Mouse Fluorescence Detection Kit (Max Vision Biosciences, USA), using anti-PCNA (2 µg/ml, PC10 mouse mAb, Santa Cruz Biotechnology), followed by ALEXA FLUOR® brand fluorescent dye 488-labelled goat anti-mouse IgG. Tumour blood vessels were stained with anti-hCD31 mAb. OCT-embedded sections were fixed in 100% acetone (−20° C., 10 min), air-dried and washed with TBS. Samples were blocked with 2.5% goat serum and 0.5% BSA in TBS (2 h, RT) and stained with anti-CD31 (overnight, 4° C., 80 ng/ml). After incubation and washing, ALEXA FLUOR® brand fluorescent dye 647-labelled goat anti-mouse IgG was added. Nuclei were stained with 4,6-diamidino-2-phenylindole (DAPI; Sigma) and slides mounted with FLUOROMOUNT-G® brand mounting medium (Southern Biotech, Birmingham, Al) for all microscopy preparations.

Tissue Imaging and Analysis

Digital images were acquired on a Leica laser scanning multispectral confocal microscope (TCS SP5, Leica Microsystems). Image stacks consisted of five image planes acquired through a 20× lens (calculated optimal zoom factor 2, z-step 1.39 µm). At least three sections and 12 to 30 random, noncontiguous, non-overlapping fields per section were acquired and examined for each tumour. Density per optical field of TUNEL- and PCNA-positive nuclei and of CD31-positive vessel fragments was quantified and the estimated mean number of positive structures calculated using data from all optical fields. Quantification was performed with zoomed images using the Adobe Photoshop Count Tool.

Complement-Dependent Cytotoxicity (CDC)

MOLT-4 cells ($10^5$ target cells/100 µl) were plated in a 96-well V-bottom plate, incubated with indicated concentrations of anti-hCCR9 or an isotype-matched control mAb (30 min, 37° C.), centrifuged and washed. Active or 56° C.-heat-inactivated baby rabbit complement (25%; AbD Serotec, UK) was added to cells in serum-free DMEM with 1% BSA (1 h, 37° C.). Cells were stained with the viability exclusion marker 7-AAD (BD Biosciences; 10 min, 4° C.) and the number of non-viable cells evaluated by flow cytometry; each condition was analyzed in triplicate. Specific lysis was calculated as 100×(% dead cells with active complement−% dead cells with inactive complement)/(100%−% dead cells with inactive complement).

Statistical Analyses

Statistical analyses were performed using GraphPad Prism 4 software (San Diego, Calif.). Statistical significance was established at $p<0.05$, as evaluated by Student's t-test, unless otherwise indicated. Results are shown as mean±SEM.

Example 1

91R mAb Specifically Recognizes the Human Chemokine Receptor CCR9

The mouse anti-hCCR9 mAb was generated after immunization with the full-length coding sequence of hCCR9 inserted in a eukaryotic expression vector. Specificity was first assessed by flow cytometry on HEK293 cells stably expressing hCCR9 or the empty vector. Although human and mouse CCR9 share 86% sequence identity, the 91R mAb only recognized cells expressing human CCR9 (FIG. 1A). 91R did not crossreact with stable HEK293 transfectants expressing hCCR4, hCCR5, hCCR6 or hCCR8 chemokine receptors (FIG. 1A), which show 30-36% identity with hCCR9, demonstrating 91R specificity.

91R recognized endogenous human CCR9 on the T-cell acute lymphoblastic leukaemia MOLT-4 cell line but did not stain negative control Jurkat cells (FIG. 1B) (Zabel et al., 1999, J Exp Med 190:1241-56). A commercial anti-hCCR9 (112509 mAb) was compared in parallel (FIG. 1B); at the same mAb concentrations (10 µg/ml), 91R showed 13-fold higher mean fluorescence intensity on MOLT-4 cells than the 112509 mAb (MFI; 49.7 vs. 3.8). At a suboptimal concentration (0.12 µg/ml), 91R still stained 100% of MOLT-4 cells, with a MFI of 10.9, higher than the signal at saturating concentrations of 112509 (FIG. 1C); this indicated higher 91R mAb affinity for CCR9 and/or recognition of a more accessible epitope. 91R also recognized endogenous human CCR9 on normal cells. 91R stained thymocytes at all stages of T cell maturation, with maximum binding to $CD4^+CD8^+$ DP cells (FIG. 1D). In addition, 2-3% of peripheral blood lymphocytes, mainly the $CD3^+$ population, were stained by 91R (FIG. 1E).

91R specificity was further assessed in Western blots using membrane extracts of hCCR9- and pClneo-HEK293 transfectants (mock transfected- and hCCR9-HEK293; FIG. 1G). In samples from hCCR9 transfectants, 91R specifically recognized a 43 kDa band, in accordance with the estimated molecular weight of hCCR9 (369 amino acids; estimated MW 42,016 Da). Similarly, a 47 kDa band was detected in MOLT-4 but not in Jurkat cell samples. Differences in apparent molecular weight between hCCR9 bands in HEK293 and MOLT-4 cells might be due to glycosylation differences (FIG. 1G).

Example 2

The hCCR9 N-Terminal Domain is Necessary for 91R mAb Epitope Recognition

CCR9 is organized in seven transmembrane domains, with an extracellular N-terminal (Nt), three intracellular, three extracellular and an intracellular C-terminal domain (FIG. 2A). Human and murine CCR9 show 86% amino acid sequence identity differing in 31 residues. To map the hCCR9 domain recognized by 91R, an expression vector in which the hCCR9 Nt was replaced by the murine sequence (mNt/hCCR9) (FIG. 2A) was generated and expressed in HEK293 cells. Flow cytometry analyses showed that whereas the K629 anti-mouse CCR9 Ab recognized the chimeric receptor, 91R did not (FIG. 2A), indicating that the hCCR9 Nt domain was needed for 91R epitope recognition.

Since the hCCR9 Nt domain has a putative N-glycosylation site at Asn32, the recognition site of 91R was tested to confirm whether it recognised a glycosidic epitope or the peptide backbone. MOLT-4 and hCCR9-KEK293 cell lysates were treated with PNGase, followed by electrophoresis and Western blot with 91R. Untreated MOLT-4 cell extracts showed a predominant protein band of 47 kDa and a minor band of 43 kDa, whereas a single 39 kDa band appeared in PNGase-treated lysates (FIG. 2C). In CCR9-transfected HEK293 cell extracts; 91R detected 43 and 39 kDa bands in untreated and PNGase-treated lysates, respectively. The results confirm that hCCR9 is an N-glycosylated protein, and that the glycosyl moiety is neither a part of nor masks the epitope recognized by 91R, suggesting that this mAb specifically recognizes the hCCR9 peptide backbone.

Example 3

The CCR9 Ligand CCL25 Partially Blocks 91R Binding to MOLT-4 Cells

Figure 3:
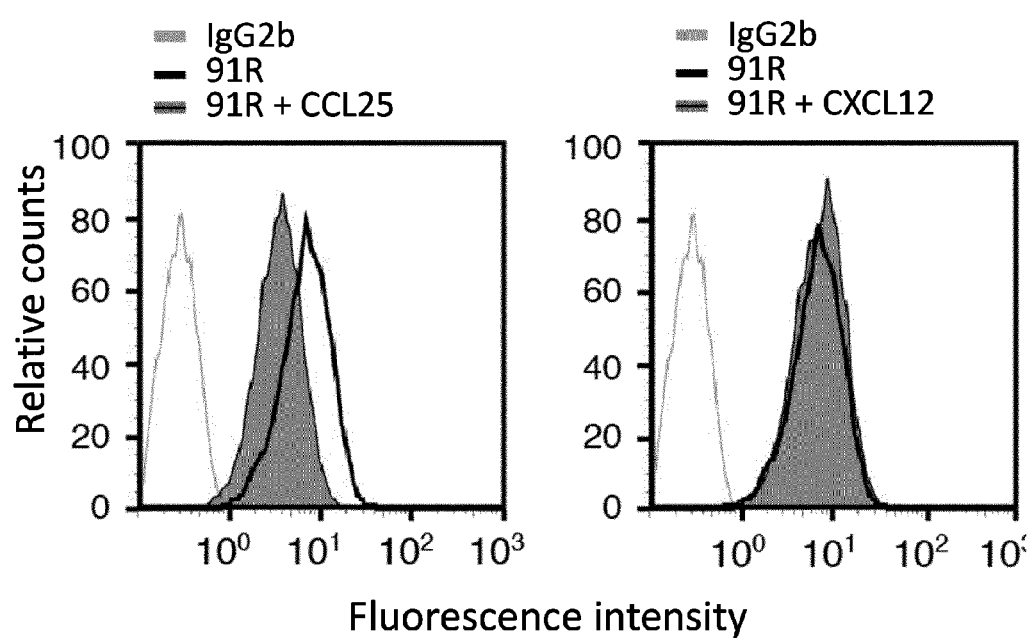
FIG. 3. Human CCL25 partially competes with 91R mAb for binding to MOLT-4 cells. Representative flow cytometry analysis of human MOLT-4 cells, preincubated alone or with 10 μg/ml hCCL25 or hCXCL12 (40 min, 4° C.), stained with 91R or isotype-matched mAb (n=3).

To study whether CCL25 affects CCR9 recognition by 91R, MOLT-4 cells were preincubated alone or with hCCL25, in the presence of sodium azide to inhibit receptor internalization (40 min, 4° C.), followed by incubation with 91R and flow cytometry analysis. CCL25 partially inhibited 91R binding (FIG. 3A). This effect was specific, since the control chemokine CXCL12 did not affect mAb binding (FIG. 3B), suggesting that CCL25 and 91R binding sites on CCR9 partially overlap or are in close proximity.

Example 4

91R mAb Inhibits In Vivo Growth of Human Tumours in Xenografts

Figure 4:
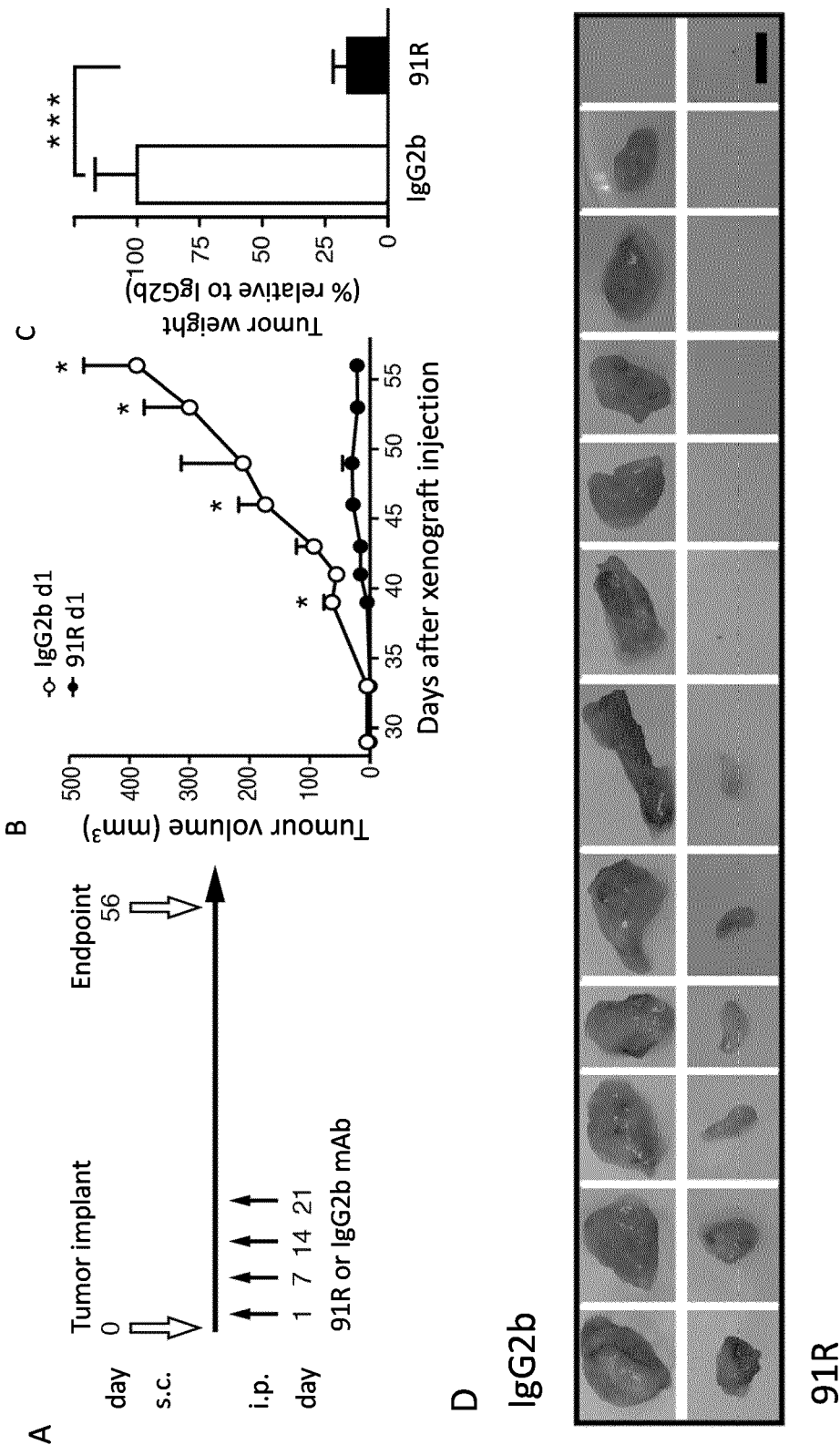
FIGS. 4A-4H. Leukemia xenograft growth is inhibited in mice treated with 91R mAb. For xenograft analyses, MOLT-4 cells were inoculated subcutaneously (s.c.) in Rag2−/− mice on day 0 (d0). Experimental groups received four intraperitoneal (i.p.) doses of 91R or irrelevant IgG2b mAb (first and second, 4 mg/kg; third and fourth, 2 mg/kg). Tumor growth was measured with a caliper every three days. After mice were sacrificed, tumors were removed and weighed.
Figure 4:
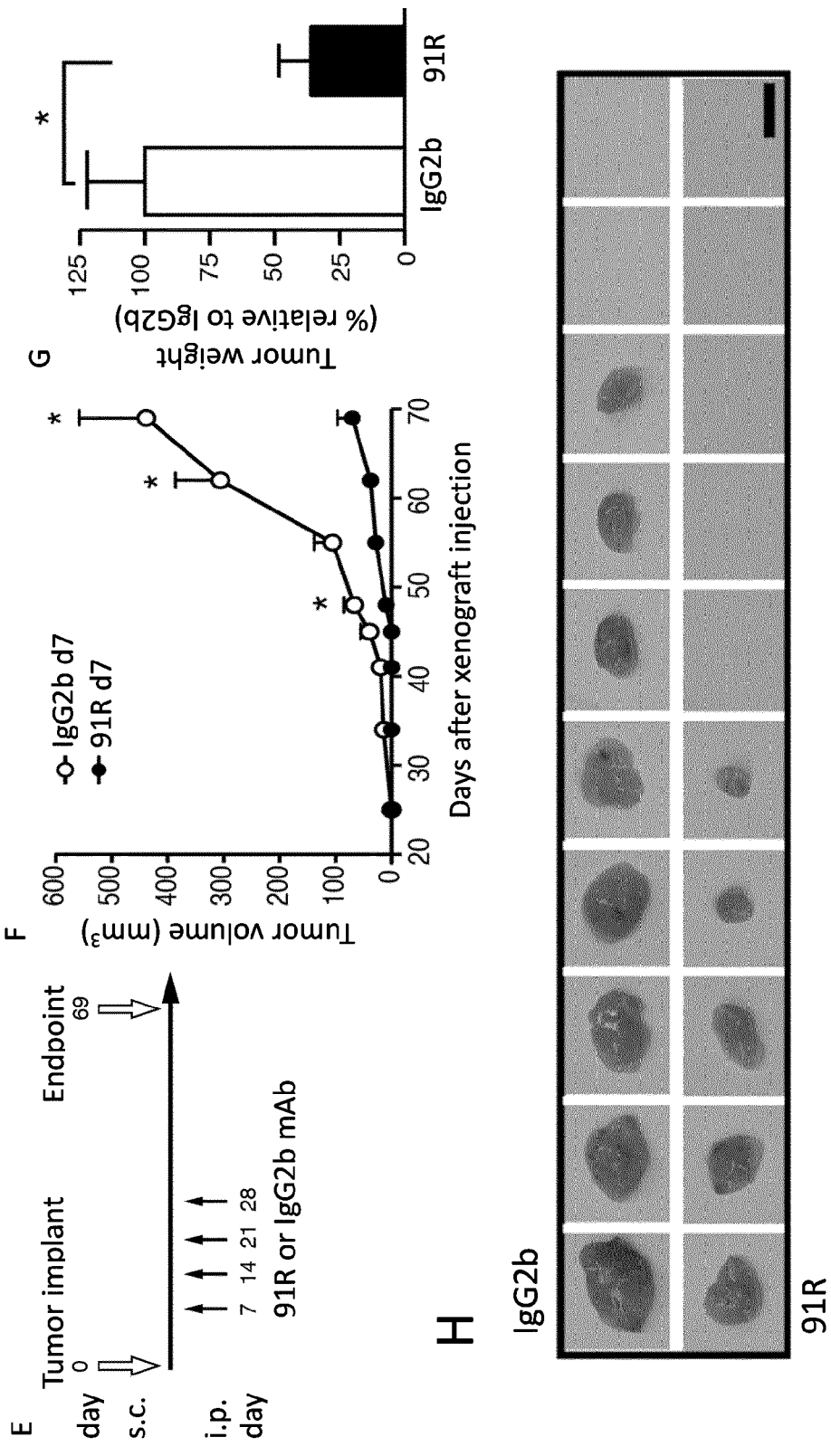

MOLT-4 cells implanted in immunodeficient mice grow as tumours. Two approaches were used to assess the anti-tumour potential of 91R in this model. In a first experimental design, two groups of mice were inoculated subcutaneously with MOLT-4 cells in both dorsal flanks (day 0); then they received four weekly intraperitoneal injections of 91R or an isotype-matched mAb (P-020, IgG2b), starting the day after MOLT-4 cell implant (FIG. 4A). Tumours developed and their size was measured regularly until day 56, when the mice were sacrificed. Significantly smaller tumours were already apparent in 91R-treated mice at day 39 (p=; FIG. 4B). At day 56, tumours for each mouse group were removed and weighed; calculation of total tumour burden, measured as the sum of tumour weights for each group, was reduced by 84±18% in the 91R-treated group compared to controls (tumour burden per mouse 63.3±30.3 mg vs 397±65 mg; p=0.0009; FIG. 4C). The largest individual tumour from 91R-treated mice was smaller than any tumour from control mice (FIG. 4D); all control mice developed tumours, whereas two 91R-treated mice were tumour-free (n=6 mice/group).

To test the ability of the 91R mAb to inhibit tumour growth in more restrictive conditions, treatment was initiated at 7 days post-MOLT-4 cell implant. Four mAb doses were administered at weekly intervals as above (FIG. 4E) and tumour size measured until day 69, when mice were sacrificed. Difference in tumour size between the two mouse groups was apparent by day 48 (p=0.012; FIG. 4F), and tumour burden data showed a 64±29% reduction in 91R— compared to control-treated mice (163±56 mg vs 451±117 mg; p=0.039; FIG. 4G). For these experiments, MOLT-4 cells were injected into only one flank; two control mice and four 91R-treated mice were tumour-free, and the size of the largest tumour from a 91R-treated mouse was similar to the smallest tumour from a control mouse (FIG. 4H).

Figure 5:
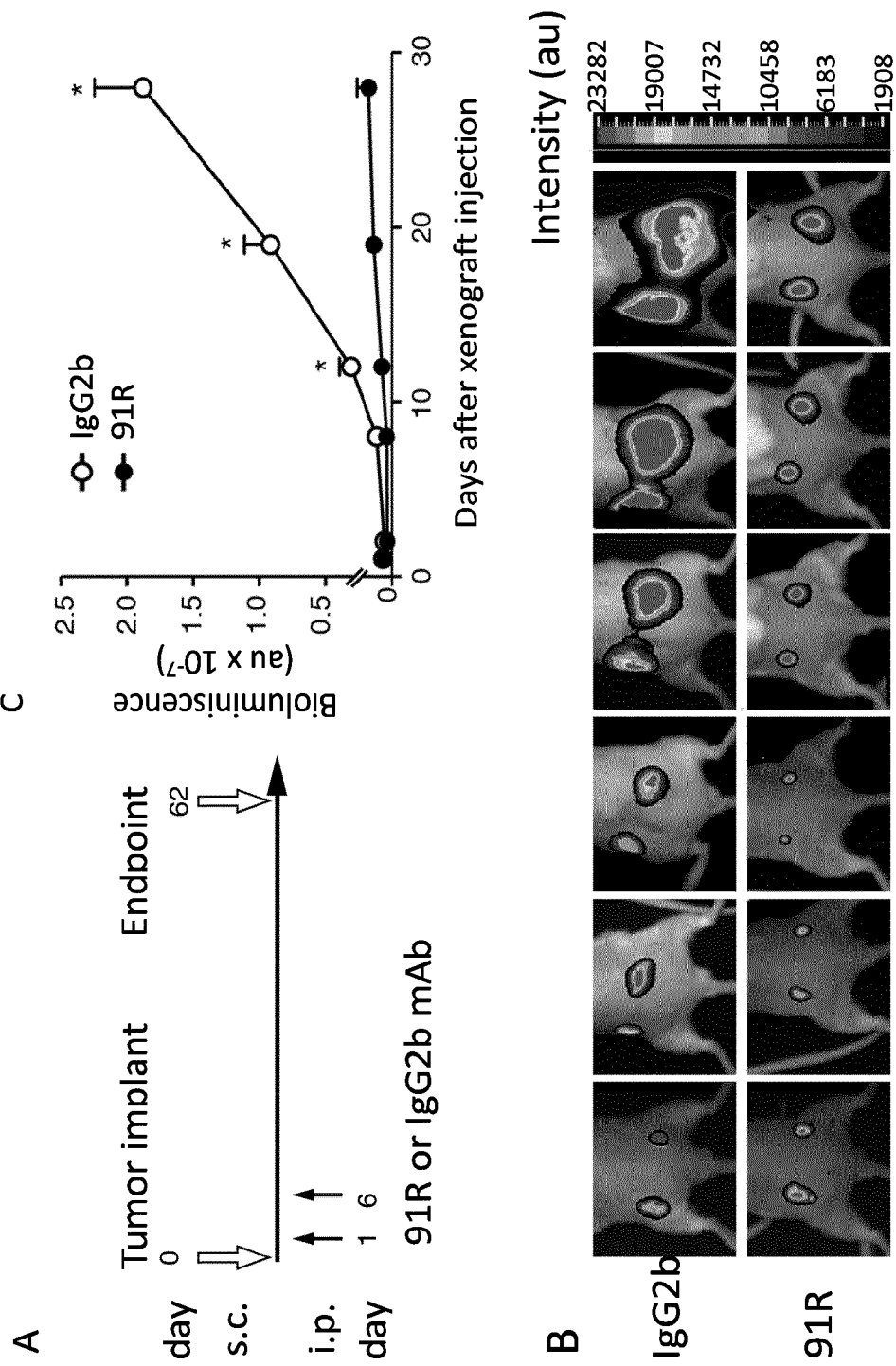
FIGS. 5A-5E. Short-term kinetics of 91R mAb-induced reduction of leukemia xenograft growth.

To evaluate tumour growth at early stages when a direct caliper measurement was not possible, a MOLT-4 cells expressing luciferase (MOLT-4-luc) were injected into the dorsal flanks of Rag2$^{-/-}$ mice. To determine the effect of reducing the number of antibody doses, 91R and control antibodies were also administered on days 1 (100 μg/mouse) and 6 (50 μg/mouse) (FIG. 5A). Implanted tumours were monitored by luminescence imaging (FIG. 5B), and mice were sacrificed on d62. Luminescence analyses indicated tumour growth from day 2, which was inhibited in 91R-treated mice from day 12 (p=0.032; FIG. 5B, C). 91R treatment resulted in a total reduction in tumour burden of 85±11% relative to controls (FIG. 5D). Three of the seven 91R-treated mice were tumour-free, and tumours from the remaining four mice were smaller than in controls, as determined by weight and relative luminescence (223±103 mg vs 1,478±262 mg; p<0.0001; FIG. 5 E).

These results indicate an anti-tumour effect of 91R in the MOLT-4 mouse model.

Example 5

Figure 6:
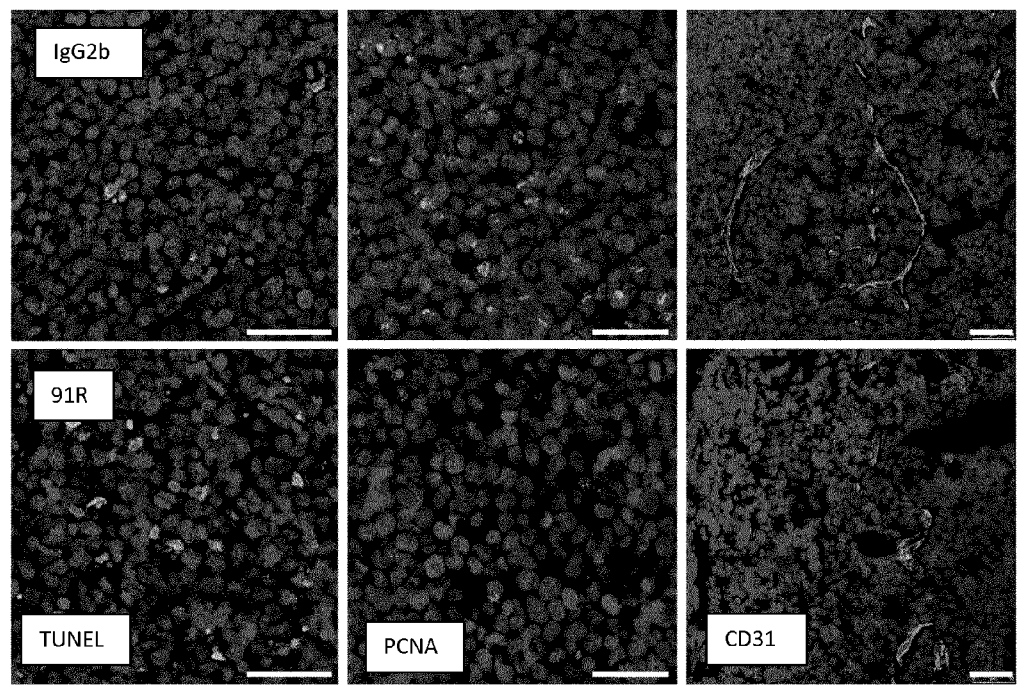
FIGS. 6A-6D. 91R mAb promotes apoptosis and necrosis and reduces cell proliferation and angiogenesis in tumor xenografts.
Figure 6:
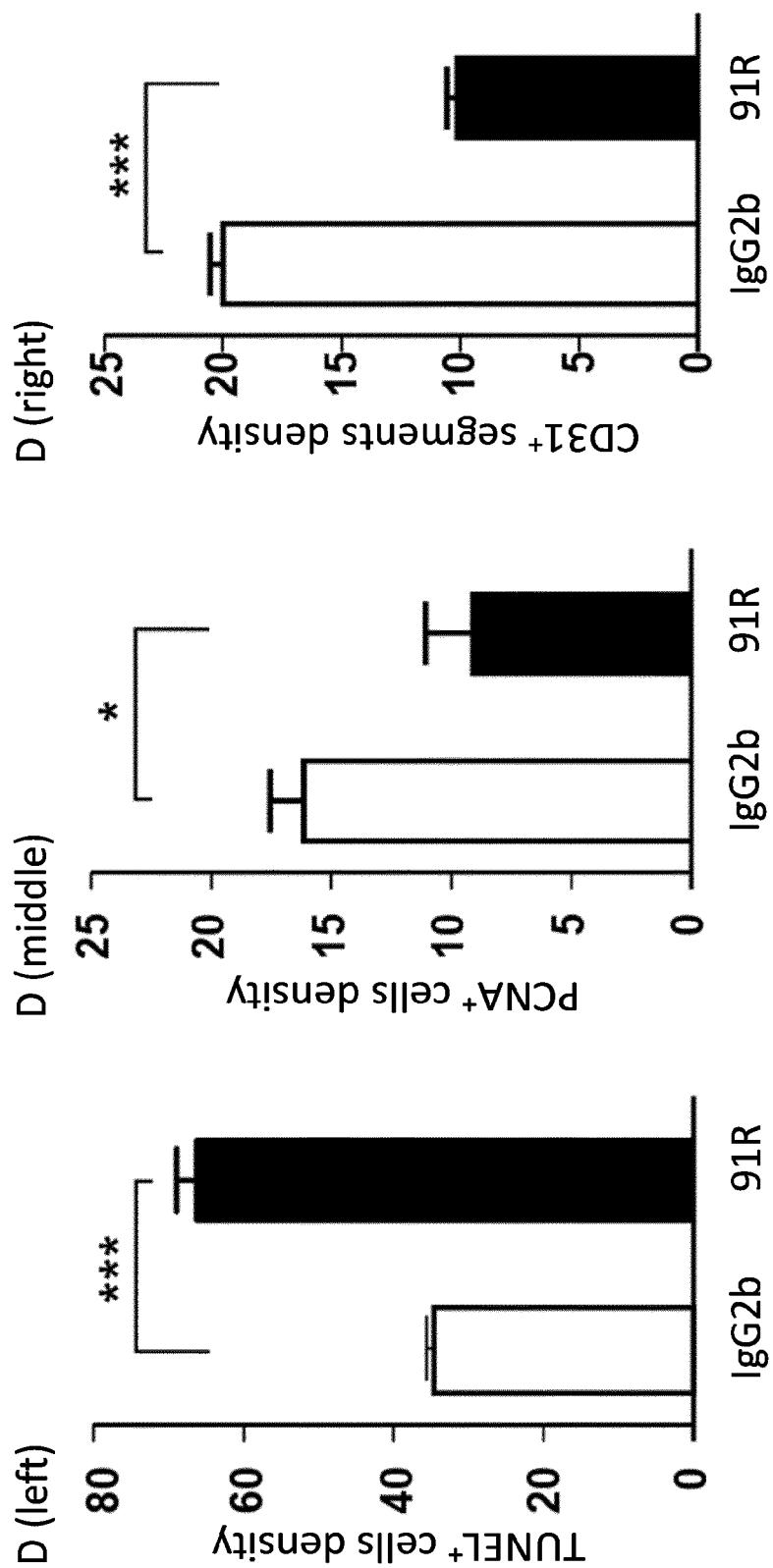

91R-Treated Tumours Show Increased Necrosis and Apoptosis as Well as Reduced Angiogenesis and Cell Proliferation The effect of 91R treatment on MOLT-4 tumours was examined by histochemical analysis. Sections from tumour xenografts collected at necropsy were hematoxylin/eosin-stained and the percentage of necrotic area relative to total area was calculated for each tumour section; the necrotic region was defined as that devoid of cells and surrounded by areas with dense accumulation of purple nuclei (FIG. 6A). Tumours were classified into three categories, based on the extent of necrotic area: low (<1%), medium (1-30%) and high (>30%) (FIG. 6B). High necrosis levels were detected only in 91R-treated mice (40% of tumours); the medium grade level was 20% for 91R-treated and 50% for control mice. Differences in the frequency distribution for each antibody treatment were statistically significant (p<0.0001; FIG. 6B).

TUNEL assays were used to determine degree of apoptosis, which precedes cell clearance and could lead to necrotic acellular areas. Compared to controls, 91R-treated tumours showed a significant increase in apoptotic cell density (1.93-fold; p<0.0001; FIG. 6C, D left).

Cell proliferation was quantified by labelling proliferating cell nuclear antigen (PCNA) in paraffin-embedded tumour sections; 91R-treated tumours showed a significant decrease in the fraction of proliferating cells compared to control tumours (40%; p<0.0001; FIG. 6C, D centre).

Tumour growth is also associated with the extent of intratumour neovascularization. Evaluation of tumour angiogenesis by immunohistochemical detection of the endothelial marker CD31 showed a reduction in microvessel density in 91R-treated compared to control tumours (50.7%; p<0.0001; FIG. 6C, D right).

These data indicate that 91R interferes with tumour growth by increasing apoptotic cell death and necrosis levels and reducing cell proliferation and intratumour microvessel density.

Example 6

91R mAb Mediates Complement-Dependent Cytotoxicity

Complement-dependent cytotoxicity (CDC) is one of the main in vivo mechanisms for tumour cell elimination by therapeutic antibodies, by which complement component C1q is recruited to antibody-opsonized cells (classical pathway) and promotes their specific lysis. The in vitro ability of 91R to induce lysis of MOLT-4 leukaemia cells was tested by complement fixation. MOLT-4 cells were preincubated with 91R, 112509 or appropriate isotype-matched mAb, after which baby rabbit complement was added (1 h, 37° C.). Specific cell death was evaluated by flow cytometry analyses of 7-AAD incorporation.

Figure 7:
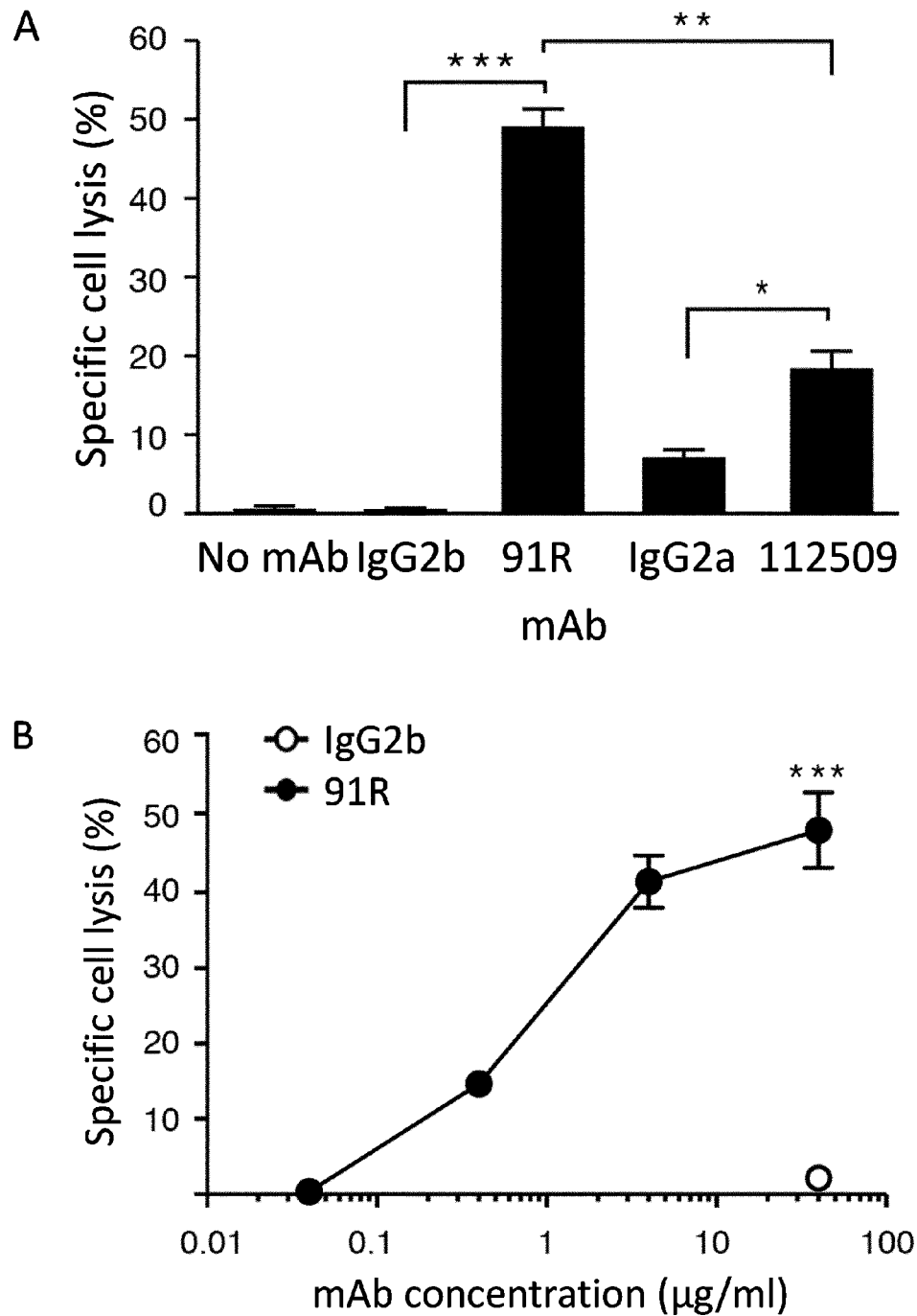
FIGS. 7A-7D. 91R mAb promotes in vitro complement-dependent cytotoxicity in human leukemic MOLT-4 cells. MOLT-4 cells were opsonized with 91R or isotype-matched mAb (40 μg/ml, 30 min, 37° C.), washed, and incubated (1 h) with 25% active (37° C.) or inactive (56° C.) baby rabbit complement (BRC); cell viability was evaluated in a flow cytometer by 7-AAD staining.
Figure 7:
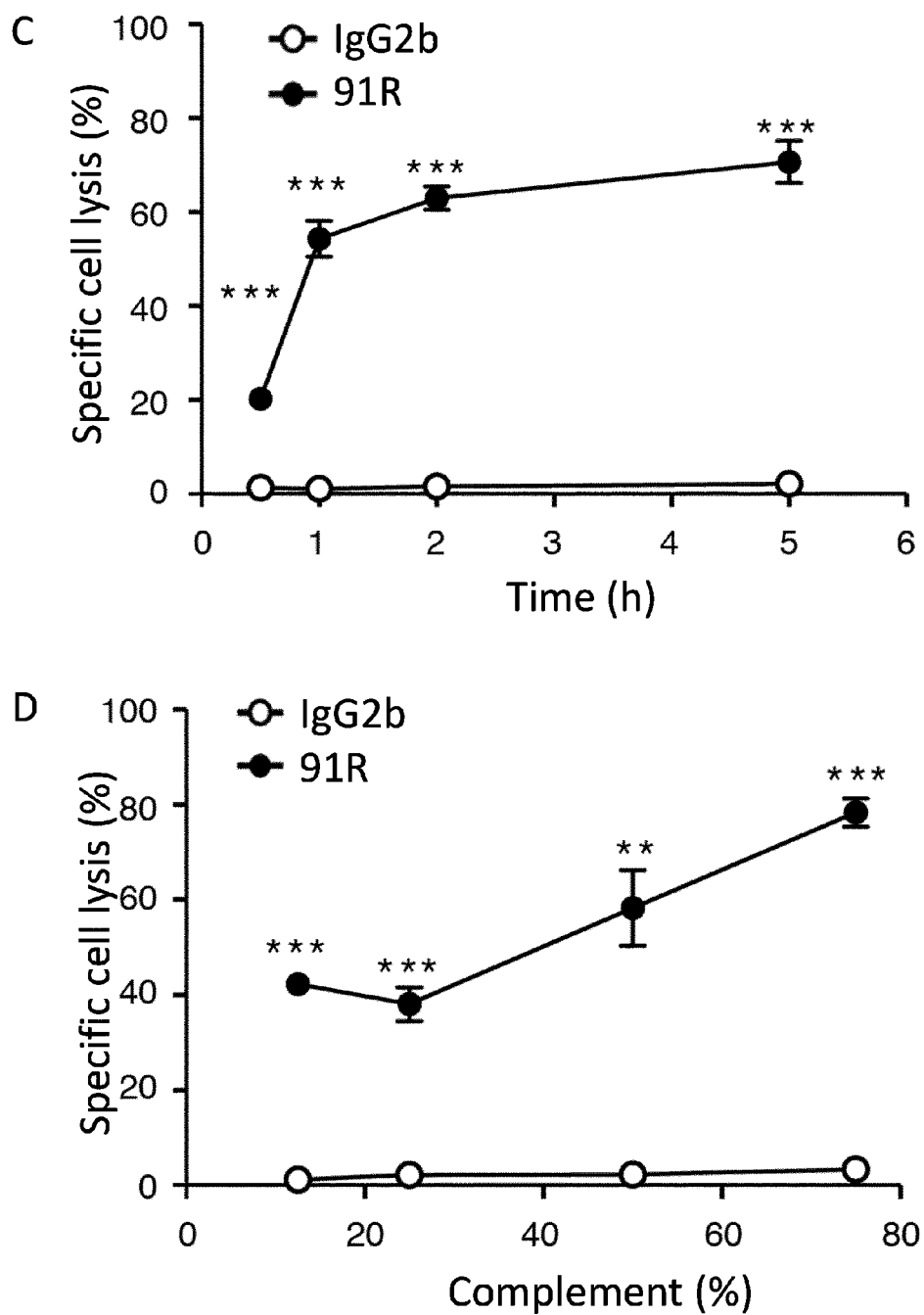

91R promoted complement-specific lysis of MOLT-4 cells (49±2%; p<0.0001; FIG. 7A) at a higher level than 112509 mAb (18±2%; p=0.03; FIG. 7A).

To optimize conditions for 91R use, mAb concentration, complement concentration and exposure time were evaluated. Dose-response experiments showed a sigmoidal response, which was detectable at concentrations from 0.4 µg/ml (18.4±3.2%) and exceeded 40% cell lysis at 4 µg/ml mAb for 30 min (FIG. 7B). Incubation with 40 µg/ml 91R for 1 h with 25% complement yielded about 50% MOLT-4 cell lysis; longer incubations (5 h) increased lysis to 71.7±4.4 (FIG. 7C). Higher complement concentrations enhanced lysis to maximum values of 77.3±2.3 (1 h, 75% complement) (FIG. 7D). These results suggest that CDC is one of the mechanisms used by 91R to reduce MOLT-4 tumour xenografts in mice.

Example 7

Figure 8:
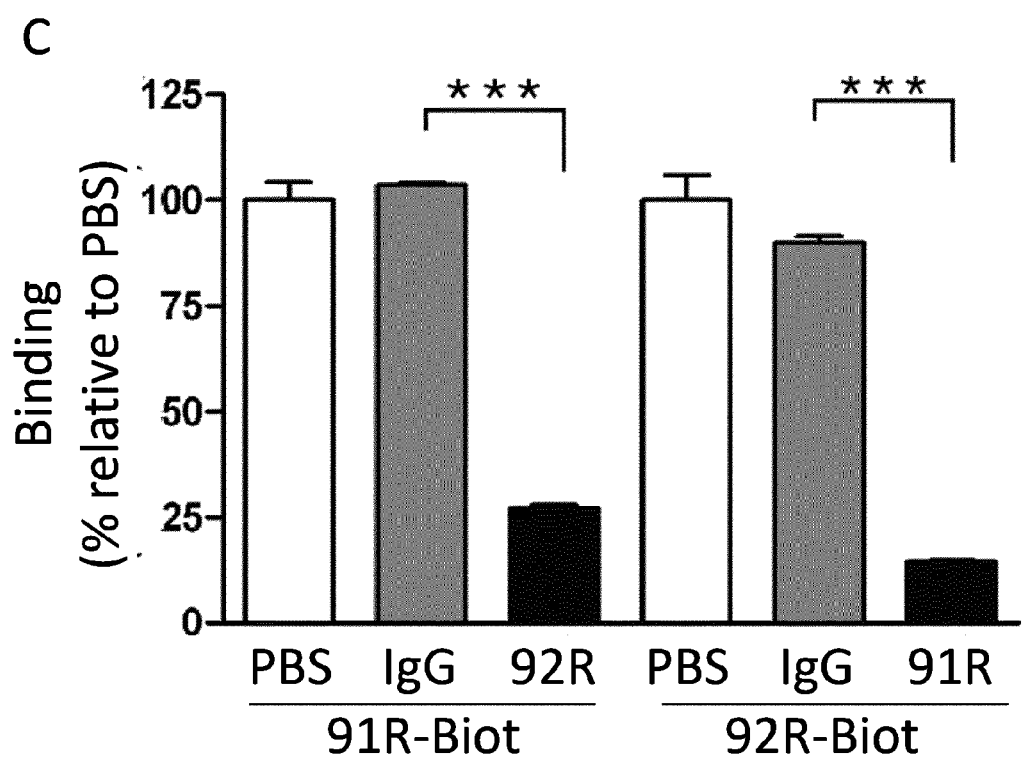
FIGS. 8A-8C. 92R mAb specifically recognizes human T cells expressing the endogenous chemokine receptor CCR9 and competes with 91R for CCR9 binding.

92R mAb Recognizes the Human Chemokine Receptor CCR9 and Competes the Binding of 91R mAb to this Receptor The mouse anti-hCCR9 mAb 92R was generated after immunization with the full-length coding sequence of hCCR9 inserted in a eukaryotic expression vector. Specificity was first assessed by flow cytometry on HEK293 cells stably expressing hCCR9 or the empty vector. Although human and mouse CCR9 share 86% sequence identity, the 92R mAb only recognised cells expressing human CCR9. 92R did not cross-react with stable HEK293 transfectants expressing hCCR4, hCCR5, hCCR6 or hCCR8 chemokine receptors, which show 30-36% identity with hCCR9, demonstrating 92R specificity. Furthermore, 92R recognised endogenous human CCR9 on the T-cell acute lymphoblastic leukemia MOLT-4 cell line but did not stain negative control Jurkat cells (FIG. 8A) (Zabel et al., 1999, J Exp Med 190:1241-56). In addition, flow cytometry analysis of MOLT-4 cells pre-incubated with the previously described mAb 91R shown that this antibody competes with mAb 92R for its binding to MOLT-4 cells (FIG. 8B).

CCR9 is organized in seven transmembrane domains, with an extracellular N-terminal (Nt), three intracellular, three extracellular and an intracellular C-terminal domain (FIG. 2A). Human and murine CCR9 show 86% amino acid sequence identity differing in 31 residues. Results from ELISA analyses using a synthetic peptide corresponding to amino acids 2-22 of hCCR9 (SEQ ID NO:11) as antigen shown that the CCR9 epitope recognized by 92R mAb is localized at the Nt domain. Using these assays it was also shown that both mAbs 91R and 92R compete with each other for binding to this synthetic peptide comprising hCCR9 amino acids 2-22 (FIG. 8C).

Example 8

91R, 92R mAbs are Structurally Different to 3C3 mAb

In order to evaluate whether the 91R and 92R mAbs differed structurally from the 3C3 anti-hCCR9 mAb described in the state of the art (WO 00/53635), their CDRs were sequenced. The sequences of the six CDRs of 3C3 mAb are identified as SEQ ID NO: 13 (CDR-H1), SEQ ID NO: 14 (CDR-H2), SEQ ID NO: 15 (CDR-H3), SEQ ID NO: 16 (CDR-L1), SEQ ID NO: 9 (CDR-L2), SEQ ID NO: 17 (CDR-L3). The alignment shown in FIG. 9 demonstrates that none of the heavy chain CDRs and CDR-L1 and CDR-L3 of 91R and 92R mAbs were identical to the corresponding CDRs of 3C3 mAb. In fact, only the CDR-L2 of 92R mAb and 3C3 mAb shared the same sequence (SEQ ID NO: 9). Additionally, the percentages of sequence identity between the CDRs of each of 91R or 92R mAbs and 3C3 mAb were calculated (Table 1).

TABLE 1

| | Percentages of sequence identity between antibodies 91R or 92R and antibody 3C3. | | | | | |
|---|---|---|---|---|---|---|
| Antibodies | % Identity CDR-H1 | % Identity CDR-H2 | % Identity CDR-H3 | % Identity CDR-L1 | % Identity CDR-L2 | % Identity CDR-L3 |
| 91R/3C3 | 0% | 26.3% | 12.5% | 75% | 85.7% | 44.4% |
| 92R/3C3 | 0% | 26.3% | 12.5% | 87.5% | 100% | 33.3% |

Example 9

Figure 11:
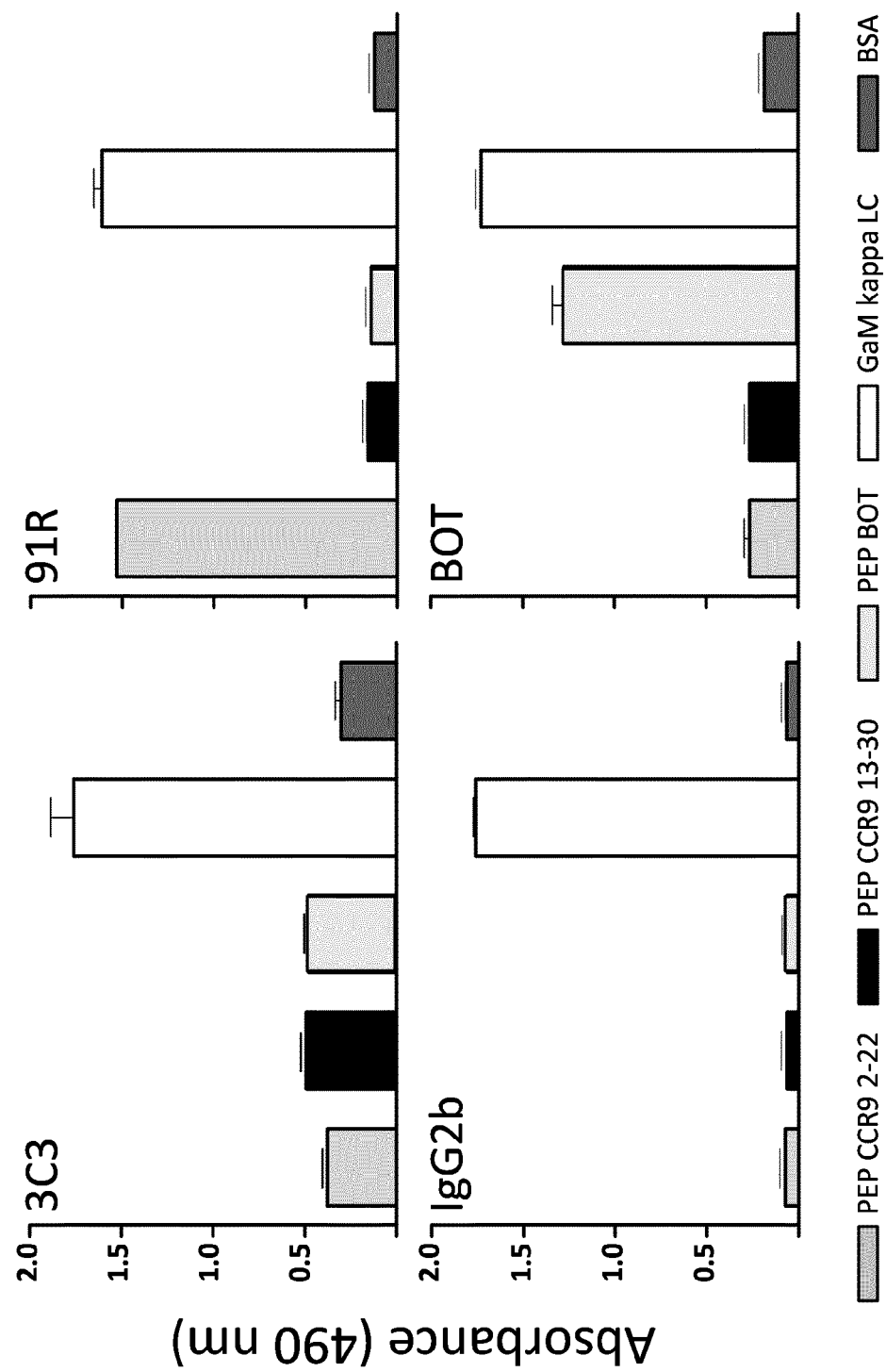
FIG. 11. Binding of 91R and 3C3 mAbs to hCCR9-derived peptides on ELISA plates. Plates were coated with synthetic peptides corresponding to amino acids 2-22 (SEQ ID NO: 11) and 13-30 (SEQ ID NO: 12) of hCCR9, peptide BOT (a non-related control synthetic peptide), goat anti mouse kappa light chain antibody (GaM kappa LC) or bovine serum albumin (BSA). After blocking with BSA, 3C3, 91R, BOT or isotype control mAbs were added. After washing, a horseradish peroxidase-conjugated goat anti mouse immunoglobulins was added and incubated. Finally, plates were washed and developed with OPD and $H_2O_2$. Results were quantified by measuring absorbance at 490 nm. No blanks were substracted. One representative experiment is shown (n=2).

91R and 92R mAbs Recognize a Different Epitope in hCCR9 than the One Recognized by 3C3 mAb The pattern of hCCR9 recognition by 91R mAb was compared to that of 3C3 mAb. While both antibodies recognised endogenous human CCR9 on the T-cell acute lymphoblastic leukemia MOLT-4 cell line and did not stain negative control Jurkat cells (FIG. 10A), 91R and 3C3 mAbs have different recognition patterns of hCCR9-transfected HEK-293 (FIG. 10B). In particular, 3C3 mAb has higher non-specific binding to mock-transfected cells than 91R mAb. This difference was further analysed by ELISA using synthetic peptides derived from hCCR9. Results shown in FIG. 11 revealed that 91R mAb recognized a peptide corresponding to amino acids 2-22 (SEQ ID NO: 11) of hCCR9 and exhibited negligible binding to a peptide corresponding to amino acids 13-30 (SEQ ID NO: 12) of hCCR9, whereas 3C3 mAb does not bind to any of these peptides.

Figure 12:
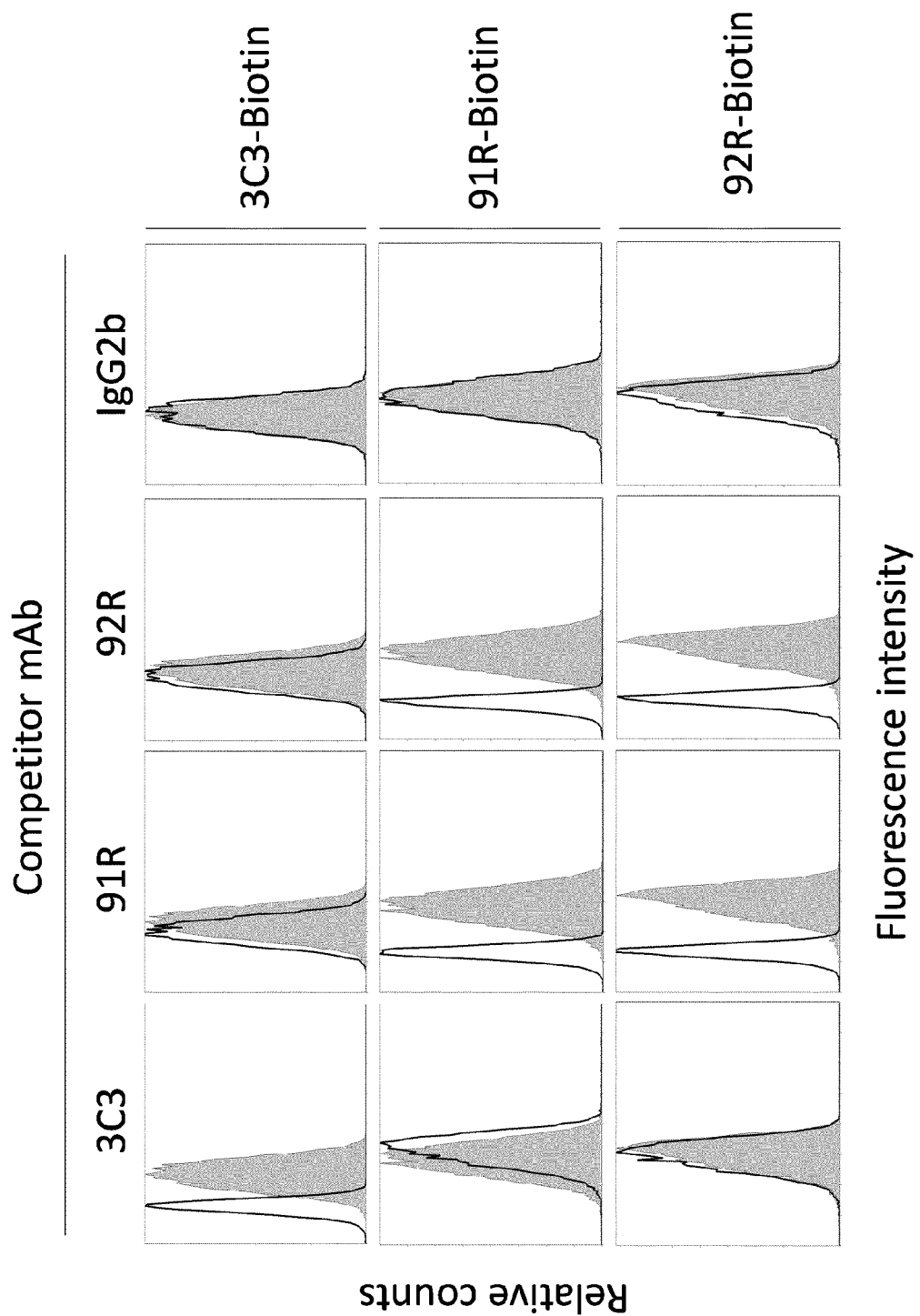
FIG. 12. Competitive binding assay using 91R, 92R and 3C3 mAbs and MOLT4 cells. MOLT4 cells (2×10$^5$ cells/well) were preincubated with 50 µl of PBSst (filled histograms) or with 3C3, 91R, 92R or isotype control mAbs (20 µg/ml, open histograms). After 30 minutes at 4° C., 50 µl of biotin-labelled 3C3, 91R or 92R mAbs (5 µg/ml) were added and the incubation continued for 20 additional min. After washing, cells were incubated with PE-labelled Avidin and analysed by flow cytometry. One representative experiment is shown (n=2).

Competitive binding assays using 91R, 92R and 3C3 mAbs on MOLT4 cells showed that 91R and 92R mAbs compete with each other for binding to MOLT-4 cells whereas 3C3 mAb only competes with itself (FIG. 12).

Example 10

91R and 3C3 mAbs Exhibit Different Functions on MOLT4 Cells

Figure 13:
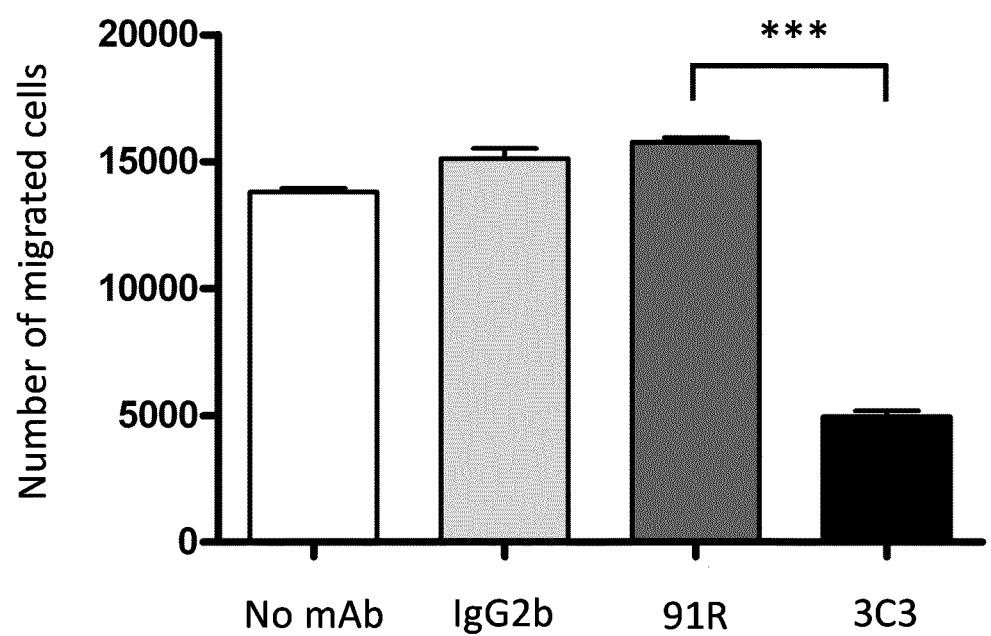
FIG. 13. Blocking MOLT-4 cells migration induced by the CCR9 ligand CCL25. Effects of anti-CCR9 antibodies on the migration of MOLT-4 cells were examined using 5 µm transwell inserts. 3×10$^5$ MOLT-4 cells previously pre-incubated alone or with isotype control, 91R or 3C3 mAbs (100 µg/ml) were plated in and allowed to migrate towards medium containing 200 nM CCL25. After 3 h, the number of migrated cells was evaluated using a flow cytometer. Data show mean±SEM of quadruplicates for one representative experiment (n=2). Student's t-test, *$p<0.001$, $p<0.01$, *$p<0.05$.

Document WO 00/53635 describes that 3C3 mAb blocks the migration of MOLT4 cells induced by the CCR9 ligand CCL25. This assay was reproduced in order to investigate the functional differences between 91R and 3C3 mAbs. Results shown in FIG. 13 revealed that 3C3 mAb blocks the CCL25-induced migration of MOLT-4 cells, whereas 91R mAb does not.

The invention claimed is:

1. An antibody or an antigen-binding fragment thereof that binds specifically to chemokine (C-C-motif) receptor 9 (CCR9), comprising:
   (i) a heavy chain that comprises a CDR-H1 comprising the amino acid sequence shown in SEQ ID NO: 1, a CDR-H2 comprising the amino acid sequence shown in SEQ ID NO: 2, and a CDR-H3 comprising the amino acid sequence shown in SEQ ID NO: 3, and the light chain comprises a CDR-L1 comprising the amino acid sequence shown in SEQ ID NO: 4, a CDR-L2 comprising the amino acid sequence shown in SEQ ID NO: 5, and a CDR-L3 comprising the amino acid sequence shown in SEQ ID NO: 6; or
   (ii) a heavy chain that comprises a CDR-H1 comprising the amino acid sequence shown in SEQ ID NO: 7, a CDR-H2 comprising the amino acid sequence shown in SEQ ID NO: 2, and a CDR-H3 comprising the amino acid sequence shown in SEQ ID NO: 3, and the light chain comprises a CDR-L1 comprising the amino acid sequence shown in SEQ ID NO: 8, a CDR-L2 comprising the amino acid sequence shown in SEQ ID NO: 9, and a CDR-L3 comprising the amino acid sequence shown in SEQ ID NO: 10.

2. The antibody or the antigen-binding fragment thereof of claim 1, wherein said fragment thereof is selected from the group consisting of an Fv fragment, a Fab fragment, an F(ab')$_2$ fragment, a Fab' fragment, an scFv, an scFv-Fc, a minibody, and a diabody.

3. A pharmaceutical composition comprising a therapeutically effective amount of at least one antibody or antigen-binding fragment thereof of claim 1, together with a pharmaceutically acceptable excipient or carrier.

4. A kit comprising at least one antibody or antigen-binding fragment thereof of claim 1.

5. The kit of claim 4, comprising a further therapeutic agent.

6. An in vitro method for detecting and/or quantifying the presence of CCR9, or cells expressing CCR9, in a sample, the method comprising:
   (a) contacting the test sample with an antibody or antigen-binding fragment thereof of claim 1; and
   (b) detecting and/or quantifying the formation of immune complexes with said antibody or antigen-binding fragment thereof.

* * * * *